US008877316B2

(12) United States Patent
Hasenoehrl et al.

(10) Patent No.: US 8,877,316 B2
(45) Date of Patent: *Nov. 4, 2014

(54) CLOTH-LIKE PERSONAL CARE ARTICLES

(75) Inventors: Erik John Hasenoehrl, Loveland, OH (US); Edward Dewey Smith, III, Mason, OH (US); Daniel Burton Sears, Hamilton, OH (US); Steven Kirk Hedges, Fairfield, OH (US); Robert Haines Turner, Cincinnati, OH (US); John Joseph Curro, Cincinnati, OH (US); Daniel Charles Peck, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 804 days.

This patent is subject to a terminal disclaimer.

(21) Appl. No.: 10/737,640

(22) Filed: Dec. 16, 2003

(65) Prior Publication Data

US 2004/0242097 A1      Dec. 2, 2004

Related U.S. Application Data

(63) Continuation-in-part of application No. 10/435,996, filed on May 12, 2003, now abandoned, which is a
(Continued)

(51) Int. Cl.
   *B32B 3/02*         (2006.01)
   *B32B 3/10*         (2006.01)
(Continued)

(52) U.S. Cl.
   CPC ....... *A61F 13/15707* (2013.01); *A44B 18/0011* (2013.01); *A61F 2013/1543* (2013.01); *A61F 13/62* (2013.01); *A61F 2013/51007* (2013.01); *A47K 2010/3266* (2013.01); *D04H 11/08* (2013.01); *A61F 13/15731* (2013.01); *A61F 2013/51366* (2013.01); *A61Q 5/02* (2013.01); *A61F 13/512* (2013.01); *A61F 13/53436* (2013.01); *A61F 13/2068* (2013.01); *A61Q 5/00* (2013.01); *B32B 5/26* (2013.01); *A61F 13/511* (2013.01); *A61F 2013/51344* (2013.01); *A61K 8/0208* (2013.01); *A61Q 19/00* (2013.01); *A61F 2013/51178* (2013.01); *A61Q 19/10* (2013.01); *A61F 13/51113* (2013.01); *A61F 13/8405* (2013.01); *A61F 13/538* (2013.01); *B32B 5/00* (2013.01)
   USPC ............... 428/88; 428/92; 428/134; 428/136; 428/137

(58) Field of Classification Search
   CPC ............ A61F 13/512; A61F 13/51305; A61F 2013/53782; A61F 13/511; B32B 3/266; B32B 3/10; B32B 3/30; B32B 5/022; B32B 2305/20; B32B 2432/00; B26F 1/20; D04H 13/002
   USPC ............ 428/85, 86, 90–93, 131–137; 442/97; 15/208, 209.1, 223–225
   See application file for complete search history.

(56) References Cited

U.S. PATENT DOCUMENTS 3,679,536 A    7/1972   Kalwaites
3,695,270 A   10/1972   Dostal
(Continued)

FOREIGN PATENT DOCUMENTS

EP       0 059506 B1    6/1987
EP       0 084963 B1   12/1989
(Continued)

OTHER PUBLICATIONS

International Search Report PCT/US 03/40232 mailed Jun. 22, 2004, six pages.

*Primary Examiner* — Jenna Johnson

(57) ABSTRACT

The article contains a fibrous, non-woven web and having a personal care composition associated with this web. The present invention relates to disposable, personal care articles useful for cleansing and/or treating the skin, hair or other similar keratin-containing surfaces. These articles are used by the consumer by either wetting the dry article with water and then rubbing the article against the skin, hair or other similar keratin-containing surfaces, or taking a wet, disposable, personal care article and rubbing against the skin, hair or other similar keratin-containing surfaces or taking a moist, disposable, personal care article and rubbing against the skin, hair or other similar keratin-containing surfaces.

21 Claims, 16 Drawing Sheets

Related U.S. Application Data continuation-in-part of application No. 10/324,661, filed on Dec. 20, 2002, now abandoned, said application No. 10/737,640 is a continuation-in-part of application No. 10/610,299, filed on Jun. 30, 2003, now abandoned.

(60) Provisional application No. 60/469,643, filed on May 12, 2003.

(51) Int. Cl.

| | | |
|---|---|---|
| *A44B 18/00* | (2006.01) | |
| *A61F 13/62* | (2006.01) | |
| *D04H 11/08* | (2006.01) | |
| *A61Q 5/02* | (2006.01) | |
| *A61F 13/512* | (2006.01) | |
| *A61F 13/20* | (2006.01) | |
| *A61Q 5/00* | (2006.01) | |
| *B32B 5/26* | (2006.01) | |
| *A61F 13/511* | (2006.01) | |
| *A61K 8/02* | (2006.01) | |
| *A61Q 19/00* | (2006.01) | |
| *A61Q 19/10* | (2006.01) | |
| *A61F 13/84* | (2006.01) | |
| *A61F 13/538* | (2006.01) | |
| *B32B 5/00* | (2006.01) | |
| *A61F 13/15* | (2006.01) | |
| *A61F 13/51* | (2006.01) | |
| *A47K 10/32* | (2006.01) | |
| *A61F 13/513* | (2006.01) | |
| *A61F 13/534* | (2006.01) | |

(56) References Cited

U.S. PATENT DOCUMENTS

| | | | |
|---|---|---|---|
| 4,035,881 A | | 7/1977 | Zocher |
| 4,042,453 A | | 8/1977 | Conway |
| 4,379,799 A | | 4/1983 | Holmes et al. |
| 4,465,726 A | | 8/1984 | Holmes et al. |
| 4,953,250 A | | 9/1990 | Brown |
| 5,062,418 A | | 11/1991 | Dyer |
| 5,080,951 A | | 1/1992 | Guthrie |
| 5,246,772 A | | 9/1993 | Manning |
| 5,382,245 A | | 1/1995 | Thompson |
| 5,397,625 A | | 3/1995 | Osteen et al. |
| 5,518,801 A | | 5/1996 | Chappell et al. |
| 5,554,145 A | | 9/1996 | Roe |
| 5,575,874 A | * | 11/1996 | Griesbach et al. ............ 156/167 |
| 5,599,420 A | | 2/1997 | Yoo et al. |
| 5,620,779 A | | 4/1997 | Levy et al. |
| 5,628,097 A | | 5/1997 | Benson |
| 5,635,290 A | | 6/1997 | Stopper et al. |
| 5,650,214 A | | 7/1997 | Anderson et al. |
| 5,658,639 A | | 8/1997 | Curro |
| 5,670,234 A | | 9/1997 | Suehr et al. |
| 5,691,035 A | | 11/1997 | Chappell et al. |
| 5,695,376 A | | 12/1997 | Datta et al. |
| 5,695,868 A | | 12/1997 | McCormack |
| 5,700,255 A | | 12/1997 | Curro |
| 5,723,087 A | | 3/1998 | Chappell et al. |
| 5,855,999 A | | 1/1999 | McCormack |
| 5,865,296 A | | 2/1999 | Angus |
| 5,916,661 A | | 6/1999 | Benson |
| 5,955,417 A | | 9/1999 | Taylor |
| 5,968,029 A | | 10/1999 | Chappell et al. |
| 5,990,377 A | | 11/1999 | Chen et al. |
| 5,993,432 A | | 11/1999 | Lodge |
| 6,028,018 A | | 2/2000 | Amundson et al. |
| 6,159,981 A | | 12/2000 | Steiner et al. |
| 6,176,952 B1 | | 1/2001 | Maugans et al. |
| 6,217,889 B1 | * | 4/2001 | Lorenzi et al. ............... 424/401 |
| 6,242,074 B1 | | 6/2001 | Thomas |
| 6,277,479 B1 | | 8/2001 | Campbell et al. |
| 6,287,407 B1 | | 9/2001 | Stein |
| 6,315,864 B2 | | 11/2001 | Anderson et al. |
| 6,328,811 B1 | | 12/2001 | Martin et al. |
| 6,342,285 B1 | | 1/2002 | Shepard et al. |
| 6,383,431 B1 | * | 5/2002 | Dobrin et al. ............... 264/154 |
| 6,395,957 B1 | | 5/2002 | Chen et al. |
| 6,458,447 B1 | | 10/2002 | Cabell |
| 2001/0018068 A1 | * | 8/2001 | Lorenzi et al. ............... 424/443 |
| 2003/0022572 A1 | | 1/2003 | Gott et al. |
| 2003/0211802 A1 | | 11/2003 | Keck et al. |

FOREIGN PATENT DOCUMENTS

| | | |
|---|---|---|
| EP | 0 162654 B1 | 10/1990 |
| EP | 0 130070 B1 | 10/1991 |
| EP | 1136050 A | 9/2001 |
| EP | 0 959845 81 | 7/2002 |
| EP | 1 236827 A1 | 9/2002 |
| EP | 1350456 A | 10/2003 |
| EP | 0 945251 81 | 12/2003 |
| GB | 2384789 A | 8/2003 |
| JP | 04240255 A2 | 8/1992 |
| WO | WO 90/04066 A2 | 4/1990 |
| WO | WO 91/12125 A1 | 8/1991 |
| WO | WO 94/02674 A1 | 2/1994 |
| WO | WO 94/23107 A2 | 10/1994 |
| WO | WO 95/16562 A1 | 6/1995 |
| WO | WO 97/45086 A1 | 12/1997 |
| WO | WO 98/42289 A1 | 10/1998 |
| WO | WO 99/14039 A1 | 3/1999 |
| WO | WO 99/16947 A1 | 4/1999 |
| WO | WO 99/25318 A1 | 5/1999 |
| WO | WO 99/32698 A1 | 7/1999 |
| WO | WO 99/54134 A1 | 10/1999 |
| WO | WO 99/62446 | 12/1999 |
| WO | WO 00/00680 A1 | 1/2000 |
| WO | WO 01/08640 A2 | 2/2001 |
| WO | WO 01/08657 A2 | 2/2001 |
| WO | WO 01/09424 A1 | 2/2001 |
| WO | WO 01/45616 A1 | 6/2001 |
| WO | WO 01/54661 A1 | 8/2001 |
| WO | WO 01/76523 A2 | 10/2001 |
| WO | WO 02/34511 A1 | 5/2002 |
| WO | WO 02/00819 A1 | 6/2002 |
| WO | WO 02/053365 A2 | 7/2002 |
| WO | WO 02/100632 | 12/2002 |
| WO | WO 03/022116 A1 | 3/2003 |

* cited by examiner

CLOTH-LIKE PERSONAL CARE ARTICLES

CROSS REFERENCE TO RELATED APPLICATIONS

This application claims the benefit of U.S. Provisional Application No. 60/469,643, filed May 12, 2003, and claims priority to U.S. application Ser. No. 10/435,996, filed May 12, 2003, which is a continuation-in-part of U.S. application Ser. No. 10/324,661, filed Dec. 20, 2002, and to U.S. application Ser. No. 10/610,299, filed Jun. 30, 2003.

TECHNICAL FIELD

The present invention relates to disposable personal care articles that are cloth-like and are useful for cleansing and/or treating the skin, hair, and similar keratin-containing tissues of the body surfaces in need of such treatment and more particularly to a disposable, cleansing article comprising a fibrous non-woven web, together with a treatment composition and/or a cleansing composition applied to said non-woven fibrous web.

BACKGROUND OF THE INVENTION

Personal care products have traditionally been marketed in a variety of forms such as bar soaps, creams, lotions, and gels. These personal care products have attempted to satisfy a number of criteria to be acceptable to consumers. These criteria include cleansing effectiveness, skin feel, mildness to skin, hair and ocular mucosae, and sufficient lather volume. Ideal personal care products should gently cleanse, treat or condition the skin or hair, cause little or no irritation, and not leave the skin or hair overly dry after frequent use. Personal care products are frequently used with, or marketed in the form of articles employing a fibrous, non-woven web or other implement (e.g., washcloth, loofah, scrubbing towel, reticulated mesh, etc.) that carries a cleansing formulation or is used to deliver a separate cleansing, treatment or conditioning formulation to the skin or hair.

Traditional forms of personal care cleansing products and articles may be very useful for providing efficacious cleansing and lathering. Such conventional products and articles, however do not simultaneously deliver other desirable agents that provide skin or hair benefit. One solution to this problem is to use separate cleansing and treatment products or articles. However, this is not always convenient or practical, and many consumers would prefer to use a single article that can both cleanse and treat the skin or hair. In a typical personal care article product, a treatment agent such as a skin conditioner is difficult to formulate because it is often incompatible with the cleansing surfactants, resulting in an undesirable non-homogenous mixture. To obtain a homogeneous mixture of surfactants with treatment products such as conditioners, formulator adds emulsifiers, thickeners, and gellants to suspend the conditioning ingredients within a surfactant mixture. While the resulting composition is in an aesthetically pleasing, homogenous mixture, the conditioner is not effectively deposited onto skin or hair because the conditioners are emulsified and not efficiently released during cleansing. Also, many treatment agents have the disadvantage of suppressing lather generation. Lather suppression is a problem because many consumers seek cleansing articles that provide a rich, creamy, and generous lather.

Therefore, it is seen that conventional personal care products and articles that attempt to combine surfactants and other skin and hair treatment agents suffer from disadvantages inherently resulting from the incompatibilities of surfactants and such treatment agents. A need clearly exists to develop personal care systems which provide effective cleansing, effective lathering and yet can also consistently provide sufficient hair and skin treatment in a single article. Additionally, a need exists for personal care articles that provide unit dosing, exfoliation, and softness that may be handled in such a manner to avoid cluttering one's personal washing area.

The personal care articles of the present invention are convenient to use because they are in the form of either a single, disposable personal care article or multiple disposable articles useful for cleansing as well as application of a therapeutic or aesthetic benefit agent. Disposable articles are convenient because they obviate the need to carry cumbersome bottles, bars, jars, tubes, and other forms of cleansing, treatment and conditioning articles. Disposable articles are also a more sanitary alternative to the use of a sponge, washcloth, or other cleansing implement intended for multiple reuse, because such implements develop bacterial growth, unpleasant odors, and other undesirable characteristics related to repeated use. Fibrous webs are well known in the art. For example, fibrous, non-woven webs such as webs formed from polymer fibers are well known as materials useful for disposable products such as facing layers on absorbent articles such as diapers, for example. In preferred embodiments of the present invention, the articles are suitable for personal care applications and are useful for cleansing and/or therapeutically treating the skin, hair, and similar keratin-containing surfaces in need of such treatment.

In many applications it is desirable that fibrous webs have a bulky texture and/or softness. For example, textile wovens known as terry cloth have a bulky texture and softness and are often used for bath towels, wiping cloths, bibs, clothing, and upholstery fabric. Terry cloth is woven on specially made weaving machines, such as rapier weaving machines. Terry cloth is characterized by tufted loops of thread, and the tufts can be varied in number and density of loops. However, terry cloth is relatively expensive due to the relatively complex and expensive weaving machines necessary for its manufacture. The expense of terry cloth makes it commercially unfeasible for many applications, particularly for articles intended for limited use, such as disposable absorbent articles.

Attempts have been made to produce a fibrous, non-woven web fabric having the appearance of terry cloth. For example, U.S. Pat. No. 4,465,726 and U.S. Pat. No. 4,379,799, both to Holmes et al., describe an apertured, ribbed terry cloth-like fibrous, non-woven web fabric produced by fluid entangling of fibers on a special forming belt. Even if apertures could be avoided in the method disclosed in Holmes et al., it is well known that fluid entangling is a relatively expensive process for manufacture of fibrous, non-woven web, particularly for webs intended for disposable article use. Furthermore, webs formed by fluid entangling typically have been subjected to forces of the fluid in all the regions of the web so that the entire web is subjected to the applied mechanical energy of the fluid forces.

SUMMARY OF THE INVENTION

The present invention relates to disposable, personal care articles especially useful for cleansing and, or treating the skin, hair, and similar keratin-containing tissues or other body surfaces in need of such treatment. Each such article comprises a fibrous nonwoven web having a first surface and a second surface and comprising a first region and a plurality of discrete integral second regions, the second regions having a discontinuity exhibiting a linear orientation and a deformation comprising a plurality of tufted fibers integral with but extending from the first region and a personal care composition associated with the web.

Moreover, these articles are suitable for use within or in conjunction with another personal care implement that is designed for more extensive use. In this instance, the articles of the present invention are disposed within or attached to a separate personal care implement that is not readily disposable, e.g., a bath towel or washcloth. In addition, the disposable articles of the present invention may be removeably attached to a handle or grip suitable for moving the article over the surface to be cleansed and/or treated. Although in preferred embodiments the articles of the present invention are suitable for personal care applications, they may also be useful in a variety of other industries such as the automotive care, marine vehicle care, household care, animal care, etc., where surfaces or areas are in need of cleansing and/or application of a benefit agent, e.g., wax, conditioner, UV protectant and other similarly applied products.

In preferred embodiments of the present invention, the articles are suitable for personal care applications and are useful for cleansing and/or treating the skin, hair, and similar keratin-containing surfaces of the body, primarily skin and hair, while producing adequate lather.

The present invention also relates to personal care articles useful for cleansing and/or treating the skin, hair, and similar keratin-containing surfaces of the body, primarily skin and hair, that produce low lather to non-lathering.

Additionally, the present invention also relates to personal care articles useful for therapeutically treating the skin, hair, and similar keratin-containing surfaces of the body, primarily skin and hair, by delivering the benefit agent to the keratin-containing surface.

The present invention also relates to methods for manufacturing personal care articles of the configuration described herein. Also, the present invention provides methods for cleansing, and treating the skin or hair and similar keratin—containing surfaces of the body, primarily skin and hair using the articles described herein.

The present invention also covers kits containing a plurality of the fibrous, non-woven web that has a personal care composition associated with the web. In addition, the present invention also covers kits containing a plurality of the fibrous, non-woven web that has no treatment and, or cleansing composition on it wherein the web is packaged with certain types of compositions that during use effectuate cleansing and, or treating the skin, hair, and similar keratin-containing surfaces of the body

DETAILED DESCRIPTION OF THE INVENTION

Figure 1:
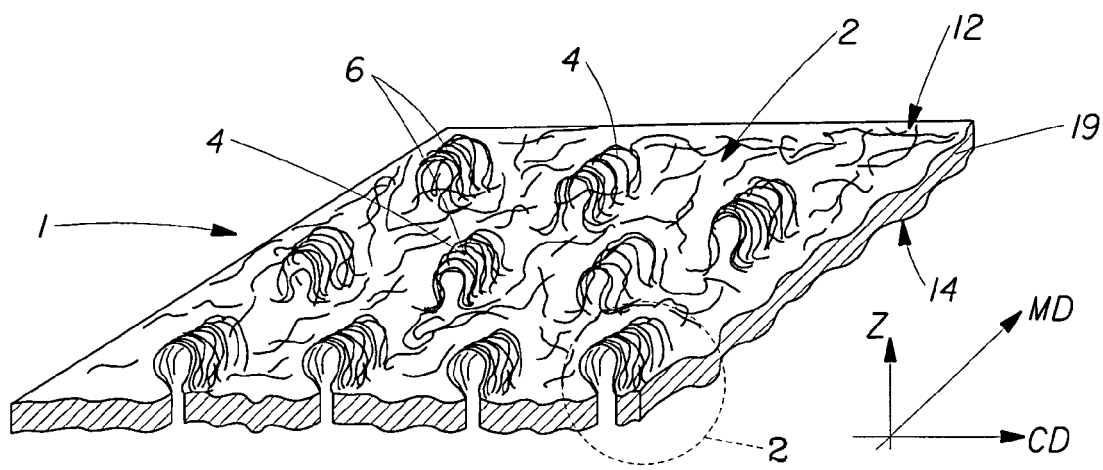
FIG. 1 is a perspective view of a web of the present invention.

The essential elements of personal care articles of the present invention, i.e., a fibrous nonwoven web formed by selective mechanical deformation of a precursor web having a first surface and a second surface, and a personal care composition are described in detail as follows. All percentages and ratios used herein, unless otherwise indicated, are by total weight of the composition unless otherwise indicated and all measurements made are at 25° C., unless otherwise designated. The invention hereof can comprise, consist of, or consist essentially of, the essential as well as optional ingredients and components described therein.

By "composition associated with the web", as used herein, means compositions that are applied to or inside of the individual fibers prior to forming the web, permeated into the web, coated onto, within or adjacent to the exposed surfaces of the web or releasably associated with the web. The presence of the "composition associated with the web" may interfere with the visibility of the tufts so that the "composition associated with the web" must either be removed mechanically or with a solvent (water, alcohol, isododecane), drying out the web, and then evaluating tufts with the "composition associated with the web" removed.

By the term "randomly" as used herein, means, e.g., exhibits a general lack of orientation within a plane such as fibers in carded webs as compared to the well defined orientation of fibers in threads and threads in a weave. Fibrous webs with modest asymmetry, such as the small amount of orientation leading to enhanced MD web strength as compared to CD wed strength, are still considered to be essentially random in that the fibers are not placed in a specific location in the web such as a thread is placed within a weave.

By "fluid" as used herein, means water, mono- and polyhydric alcohols (glycerin, propylene glycol, ethanol, isopropanol, etc.), hydrocarbon oils such as mineral oil, silicone oils having a viscosity, and can contain other components dissolved or dispersed within them, or in addition to them.

By a "lathering surfactant" is meant a surfactant, which when combined with a fluid and mechanically agitated generates a foam or lather.

The term "body cleansing composition," as used herein, means that the product or article contains enough of the surfactants described herein that it can generate at least 1400 ml of Steady Total Lather Volume, as described herein in the Steady Lather Volume Test.

The term "face cleansing composition", as used herein, means that the composition contains enough of the surfactant described herein that it can generate at least about 85 ml of Mechanical Lather Volume, as described in the Mechanical Lather Volume Test Test.

The term "low-lathering" or "non-lathering", as used herein, means that the composition generates from at the most 700 ml of Steady Flash Lather Volume, as described in the Steady Lather Volume Test.

The term "treatment agent or composition", as used herein, means a formulation to deliver cosmetic and therapeutic benefit to keratin-containing surfaces of the body, primarily skin and hair.

The term "disposable" is used herein in its ordinary sense to mean an article that is disposed or discarded after a limited number of usage events, preferably less than 5, more preferably less than about 3, and even more preferably less than about 2 entire usage events.

The term "skin conditioning composition," as used herein, means a combination of the conditioning agents which can comprise a water soluble conditioning agent; an oil soluble conditioning agent; a conditioning emulsion; or any combination or permutation of the three.

The term "water-activated," as used herein, means that some of the articles of the present invention are presented to the consumer in a form to be used when wetted with a fluid. It is found that these articles produce a lather or are "activated" by either contacting them with a fluid or producing them with a fluid and then further subjecting the article to mechanical forces, such as rubbing.

The term "substantially dry," as used herein, means that prior to use the article is substantially free of fluid and generally feels dry to the touch. As used herein, "substantially dry" means that the articles of the present invention exhibit a Moisture Retention of less than about 0.95 gms, preferably less than about 0.75 gms, even more preferably, less than about 0.5 gms, even more preferably less than about 0.25 gms, even still more preferably less than about 0.15 gms, and most preferably, less than about 0.1 gms. The determination of the Moisture Retention is discussed later. Thus, the "substantially dry" articles of the present invention will generally comprise less than about 20% by weight of fluid, preferably from 4% to about 20% by weight of fluid, and more preferably from about 4% to about 16% by weight of fluid.

The term "moist," as used herein, means that prior to use the article can feel relatively dry to the touch and still contain high fluid content. Thus, the "moist" articles of the present invention will generally comprise from about 20% to about 40% by weight of fluid.

The term "wet" means that prior to use the article can feel wet to the touch and contain high fluid content. The weight percent of fluid in the "wet" article is based on the total weight of the composition. The weight is expressed as a weight of the total composition. Thus, the "wet" articles of the present invention will generally comprise from about greater than 40% by weight of fluid, preferably from 40% to about 95% by weight of fluid, and more preferably from about 50% to about 80% by weight of fluid.

Tufted Fibrous Web

FIG. 1 shows a web 1 of the present invention. Web 1 is formed from a generally planar, two dimensional fibrous, non-woven precursor web 20, See FIG. 7, having a first surface 12 and a second surface 14, and having a machine direction (MD) and a cross machine direction (CD) as is commonly known in the art of fibrous, non-woven webs. First surface 12 corresponds to first "side" of web 1 and second surface 14 corresponds to the second "side" of web 1, the term "sides" being used in the common usage of generally two-dimensional webs, such as paper and films. Within all embodiments precursor web 20 is a fibrous, non-woven web and is comprised of randomly oriented fibers, that is, essentially randomly oriented at least with respect to the MD and CD.

Fibrous, non-woven web precursor webs 20 can be any known fibrous, non-woven webs comprising fibers having sufficient elongation or mobility of fibers properties to be formed into web 1 as described more fully below. Web 1 has a first region 2 defined on both sides of web 1 by the generally planar, two-dimensional configuration of the precursor web 20, and a plurality of discrete second regions 4 defined by spaced-apart deformations 6 and discontinuities 16 which are integral extensions of the fibers of the precursor web 20. The structure of second regions 4 is differentiated depending on which side of web 1 is considered. For the embodiment of web 1 shown in FIG. 1 and FIG. 2, on the side of web 1 associated with first surface 12 of web 1, second region 4 comprises deformations 6, each deformation 6 comprising a plurality of tufted, looped, aligned fibers 8 extending outwardly from first surface 12. Deformations 6 can be described as "tufts" of fibers, and each deformation 6 has a base 5 proximal to the first surface 12, and a distal portion 3 at a maximum distance from the first surface 12, as shown in FIG. 3. On the side of web 1 associated with second surface 14, second region 4 comprises discontinuities 16 corresponding to said deformations 6 of surface 12 that are defined by fiber orientation discontinuities on second surface 14 of web 1. As shown below, in other embodiments of web 1, the deformations 6 may be described as tufts, or tufted, but may not comprise looped or aligned fibers. Additionally, said deformations can be tufts that can comprise loop or non-looped areas.

As used herein, the term "fibrous, non-woven web" refers to a web having a structure of individual fibers or threads which are interlaid, but not in a repeating pattern as is the case with woven or knitted fabrics having oriented fibers. Fibrous, non-woven webs or fabrics have been formed from many processes including, but not necessarily limited to meltblowing processes, spunbonding processes, airlaying processes, hydroentangling processes, spunlacing processes, and bonded carded web processes. The basis weight of non-woven web fabrics is usually expressed in grams per square meter (gsm) and the fiber diameters are usually expressed in microns. Fiber size can also be expressed in denier. The basis weight of precursor web 20, See FIG. 7, can range from 10 gsm to 500 gsm., preferably from about 16 gsm to 150 gsm, more preferably from about 25 gsm to about 120 gsm, even more preferably from about 35 gsm. to about 100 gsm. For use as a bath towel a basis weight of between 125 gsm and 250 gsm may be appropriate. The constituent fibers of fibrous, non-woven web precursor web 20 can be comprised of polymer, and can be monocomponent, multicomponent, and/or multiconstituent, capillary channel fibers, hollow fibers, splittable fibers, shaped or lobed fibers and can have major cross-sectional dimensions (e.g., diameter for round fibers) ranging from 0.1-500 microns. For example, one type of fibers suitable for the nonwoven web include nanofibers.

Nanofibers are described as fibers having a mean diameter of less than 1 micron. Nanofibers can comprise all of the fibers in a nonwoven web or a portion of the fibers in a nonwoven web. The constituent fibers of the precursor web may also be a mixture of different fiber types, differing in such features as chemistry, components, diameter, shape, and the like. The constituent fibers can range from about 0.1 denier to about 100 denier. The creped nonwoven layer may comprise a variety of both natural and synthetic fibers or materials. As used herein, "natural" means that the materials are derived from plants, animals, insects or byproducts of plants, animals, and insects. The conventional base starting material is usually a fibrous web comprising any of the common synthetic or natural textile-length fibers, or combinations thereof. Nonlimiting examples of natural materials useful in the present invention include, but are not limited to, rayon fibers, silk fibers, keratin fibers and cellulosic fibers. Nonlimiting examples of keratin fibers include those selected from the group consisting of wool fibers, camel hair fibers and the like. Nonlimiting examples of cellulosic fibers include those selected from the group consisting of wood pulp fibers, cotton fibers, hemp fibers, jute fibers, flax fibers and combinations thereof. Cellulosic fiber materials are preferred in the present invention such as Tencile™. Nonlimiting examples of synthetic materials useful in the present invention include those selected from the group consisting of acetate fibers, acrylic fibers, cellulose ester fibers, modacrylic fibers, polyamide fibers, polyester fibers, polyolefin fibers, polyvinyl alcohol fibers, rayon fibers, polyethylene foam, polyurethane foam, and combinations thereof. Examples of suitable synthetic materials include acrylics such as Acrilan™, Creslan™, and the acrylonitrile-based fiber, Orlon™; cellulose ester fibers such as cellulose acetate, Amel™, and Acelem; polyamides such as nylons (e.g., nylon 6, nylon 66, nylon 610, and the like); polyesters such as Fortrel™, Kodel™, and the polyethylene terephthalate fiber, polybutylene terephthalate fiber, Dacron™; polyolefins such as polypropylene, polyethylene; polyvinyl acetate fibers; and combinations thereof. These and other suitable fibers and the nonwovens prepared therefrom are generally described in Riedel, "Nonwoven Bonding Methods and Materials," Nonwoven World (1987); The Encyclopedia Americana, vol. 11, pp. 147-153, and vol. 26, pp. 566-581 (1984).

As used herein, "spunbond fibers" refers to small diameter fibers which are formed by extruding molten thermoplastic material as filaments from a plurality of fine, usually circular capillaries of a spinneret with the diameter of the extruded filaments then being rapidly reduced. Spunbond fibers are generally not tacky when they are deposited on a collecting surface. Spunbond fibers are generally continuous and have average diameters (from a sample of at least 10) larger than 7 microns, and more particularly, between about 10 and 40 microns.

As used herein, the term "meltblowing" refers to a process in which fibers are formed by extruding a molten thermoplastic material through a plurality of fine, usually circular, die capillaries as molten threads or filaments into converging high velocity, usually heated, gas (for example air) streams which attenuate the filaments of molten thermoplastic material to reduce their diameter, which may be to microfiber diameter. Thereafter, the meltblown fibers are carried by the high velocity gas stream and are deposited on a collecting surface, often while still tacky, to form a web of randomly dispersed meltblown fibers. Meltblown fibers are microfibers which may be continuous or discontinuous and are generally smaller than 10 microns in average diameter.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries.

As used herein, the term "monocomponent" fiber refers to a fiber formed from one or more extruders using only one polymer. This is not meant to exclude fibers formed from one polymer to which small amounts of additives have been added for coloration, antistatic properties, lubrication, hydrophilicity, etc. These additives, for example titanium dioxide for coloration, are generally present in an amount less than about 5 weight percent and more typically less than about 2 weight percent.

As used herein, the term "bicomponent fibers" refers to fibers which have been formed from at least two different polymers extruded from separate extruders but spun together to form one fiber. The polymers are arranged in substantially constantly positioned distinct regions across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement. Bicomponent fibers can be splittable fibers, such fibers being capable of being split lengthwise before or during processing into multiple fibers each having a smaller cross-sectional dimension than the original bicomponent fiber. Splittable fibers have been shown to produce softer nonwoven webs due to their reduced cross-sectional dimensions. Representative splittable fibers useful in the present invention include type T-502 and T-512 16 segment PET/nylon 6 2.5 denier fibers; and type T-522 16 segment PET/PP splittable fibers, all available from Fiber Innovation Technology, Johnson City, Tenn.

As used herein, the term "conjugate fibers" refers to fibers which have been formed from at least two polymers extruded from separate extruders but spun together to form one fiber. Conjugate fibers are also sometimes referred to as multicomponent or bicomponent fibers. The polymers are usually different from each other though conjugate fibers may be nonocomponent fibers. The polymers are arranged in substantially constantly positioned distinct zones across the cross section of the conjugate fibers and extend continuously along the length of the conjugate fibers. The configuration of such a conjugate fiber may be, for example, a sheath/core arrangement wherein one polymer is surrounded by another or may be a side-by-side arrangement, a segmented configuration ration or an "islands-in-the-sea" arrangement. For two component fibers, the polymers may be present in ratios of 75/25, 50/50, 25/75 or any other desired ratios.

As used herein, the term "multiconstituent fibers," is used herein in accordance with its accepted meaning in the art, as is the term "domain". The multiconstituent fibers are understood as including those fibers comprising at least two polymers dispersed in domains, as at least one discontinuous phase, throughout another polymer, provided in the form of a continuous phase. The multiconstituent fibers are further understood as including those fibers comprising at least two or more polymers inter dispersed in domains; such dispersion may be random.

As used herein, the term "biconstituent fibers" refers to fibers which have been formed from two polymers extruded from the same extruder as a blend. Biconstituent fibers do not have the various polymer components arranged in relatively constantly positioned distinct regions across the cross sectional area of the fiber and the various polymers are usually not continuous along the entire length of the fiber, instead usually forming fibrils which start and end at random. Biconstituent fibers are sometimes also referred to as multiconstituent fibers.

As used herein, the term "capillary channel fibers" refers to fibers having capillary channels. Such fibers can be hollow fibers, for example, but are preferably fibers having capillary channels on their outer surfaces. The capillary channels can be of various cross-sectional shapes such as "U-shaped", "H-shaped", "C-shaped" and "V-shaped".

As used herein, the term "integral" as in "integral extension" when used of the second regions 4 refers to fibers of the second regions 4 having originated from the fibers of the precursor web 20 wherein the web comprises at least 4 discrete integral second regions per square centimeter. Therefore, the looped fibers 8 of deformations 6, for example, can be plastically deformed and extended fibers of the precursor web 20, and are, therefore, integral with first regions 2 of web 1. As used herein, "integral" is to be distinguished from fibers introduced to or added to a separate precursor web for the purpose of making tufts, as is commonly done in conventional carpet making, for example. It can be appreciated that a suitable nonwoven web 20 should comprise fibers capable of experiencing sufficient plastic deformation and tensile elongation, or are capable of sufficient fiber mobility such that looped fibers 8 are formed. However, it is recognized that a certain percentage of fibers urged out of the plan of the first surface 12 of the precursor web 20 will not form a loop, but instead will break and form loose ends. Such fibers are referred to herein as "loose" or "broken" fibers 18 as shown in FIG. 3. Loose fiber ends 18 can also be the result of forming deformations 6 from nonwoven webs consisting of or containing cut staple fibers. Loose fiber ends 18 are not necessarily undesirable for the present invention, but it is believed that web 1 can retain its bulky and soft character more readily when deformation 6 comprises primarily looped fibers 8 up to about 100 weight percent. In a preferred embodiment at least 5 weight percent, preferably at least 10 weight percent, more preferably at least 20 weight percent, more preferably at least 30 weight percent, more preferably at least 40 weight percent, more preferably at least 50 weight percent, more preferably 70 weight percent and even still more preferably 90 weight percent of the fibers urged in the Z-direction are looped fibers 8.

Figure 2:
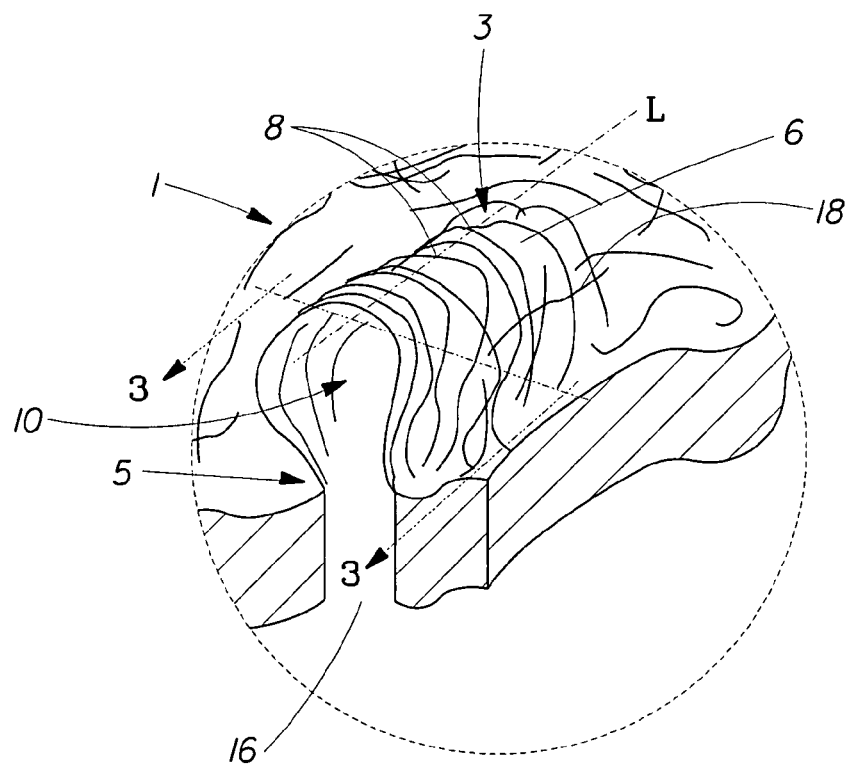
FIG. 2 is an enlarged view of a portion of the web shown in FIG. 1.
Figure 3:
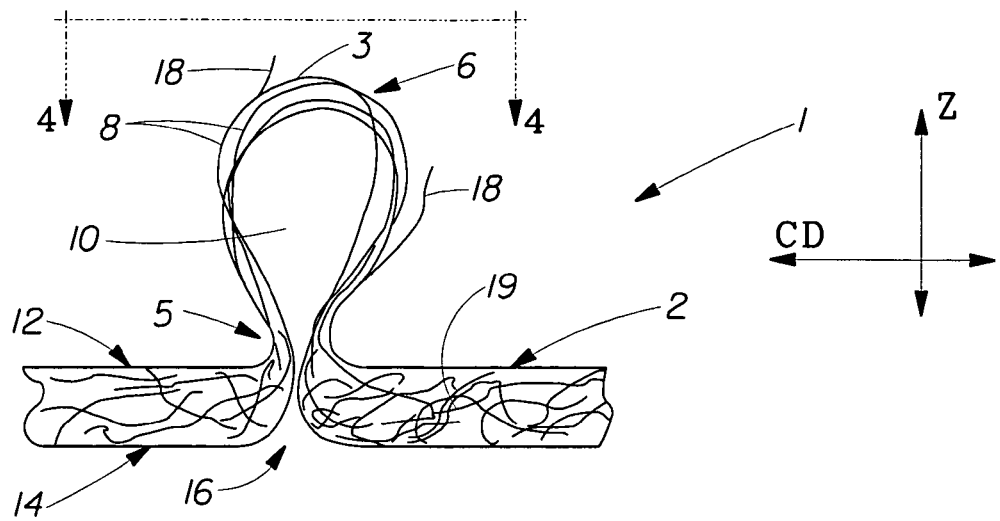
FIG. 3 is a cross-sectional view of section 3-3 of FIG. 2.

A representative deformation 6 for the embodiment of web 1 shown in FIG. 1 is shown in a further enlarged view of region 2 in FIG. 2. As shown, deformation 6 comprises a plurality of looped fibers 8 that are substantially aligned such that deformation 6 has a distinct longitudinal orientation and a longitudinal axis L. The term "longitudinal", as used herein, refers to a line, axis or direction in the plane of the deformations 6 that is aligned with the longest dimension of the deformation 6. Deformations 6 also have a transverse axis T, See FIG. 4., generally orthogonal to longitudinal axis L in the MD-CD plane. In the embodiment shown in FIGS. 1 and 2, longitudinal axis L is parallel to the MD. In one embodiment, all the spaced apart deformations 6 have generally parallel longitudinal axes L. The number of deformations 6 per unit area of web 1, i.e., the area density of deformations 6, can comprise at least 1 deformations 6 per square centimeter, preferably at least 4 deformations 6 per square centimeter, more preferably at least 10 deformations 6 per square centimeter, even more preferably at least 20 deformations 6 per square centimeter, still more preferably at least 30 deformations 6 per square centimeter. In general, the area density of deformations 6 need not be uniform across the entire area of web 1, but deformations 6 can be only in certain regions of web 1, such as in regions having predetermined shapes, such as lines, stripes, bands, circles, and the like.

Figure 4:
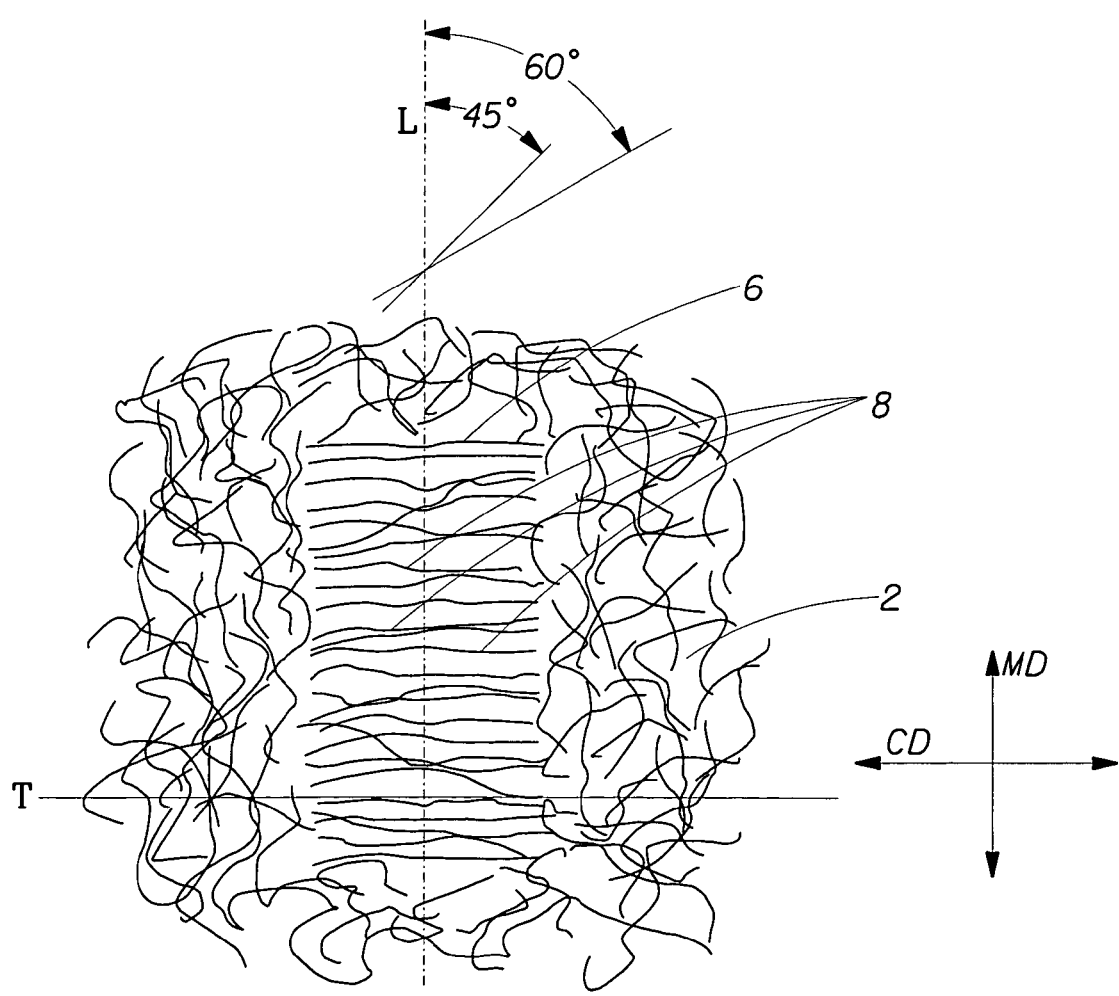
FIG. 4 is a plan view of a portion of the web as indicated by 4-4 in FIG. 3.

As shown in FIG. 2, and more clearly in FIGS. 3 and 4, one characteristic of the fibers 8 of deformations 6 in one embodiment of web 1 is the predominant directional alignment of the looped fibers 8 that are within the loop. As shown in FIGS. 3 and 4, the looped fibers 8 have a substantially uniform alignment with respect to transverse axis T when viewed in plan view, such as in FIG. 4. By "looped" fibers 8 is meant fibers 8 that begin and end in web 1. By "aligned" with respect to looped fibers 8 of deformations 6 is meant that looped fibers 8 are all generally oriented such that, if viewed in plan view as in FIG. 4, each of the looped fibers 8 has a significant vector component parallel to the transverse axis T, and preferably a major vector component parallel to the transverse axis T. As used herein, a looped fiber 8 oriented at an angle of greater than 45 degrees from the longitudinal axis L when viewed in plan view, as in FIG. 4, has a significant vector component parallel to the transverse axis T. As used herein, a looped fiber 8 oriented at an angle of greater than 60 degrees from longitudinal axis L when viewed in plan view, as in FIG. 4, has a major vector component parallel to the transverse axis T. Deformation can comprises a major vector component parallel to transverse axis T up to about 100%. In a preferred embodiment at least 1 weight percent, preferably at least 5 weight percent, more preferably at least 10 weight percent, still more preferably at least 20 weight percent, still more preferably at least 30 weight percent, even still more preferably at least 40 weight percent, still even more preferably at least 50 weight percent, still even more preferably at least 70 weight percent, and even more preferably at least 90 weight percent of fibers 8 of deformation 6 have a significant, and more preferably, a major vector component parallel to transverse axis T. Fiber orientation can be determined by use of magnifying means if necessary, such as a microscope fitted with a suitable measurement scale. In general, for a non-linear segment of fiber viewed in plan view, a straight-line approximation for both longitudinal axis L and the looped fibers 8 can be used for determining the angle of looped fibers 8 from longitudinal axis L.

The orientation of looped fibers 8 in the deformations 6 of second region 4 is to be contrasted with the fiber composition and orientation of the first region 2, which, for fibrous, nonwoven web precursor webs 20, is best described as having an essentially randomly-oriented fiber alignment.

In the embodiment shown in FIG. 1 the longitudinal axes L of deformations 6 are generally aligned in the MD. Deformations 6 and, therefore, longitudinal axes L, can, in principle, be aligned in any orientation with respect to the MD or CD. Therefore, in general, it can be said that for each deformation 6, the looped aligned fibers 8 are aligned generally orthogonal to the longitudinal axis L such that they have a significant vector component parallel to transverse axis T, and more preferably a major vector component parallel to transverse axis T.

Figure 5:
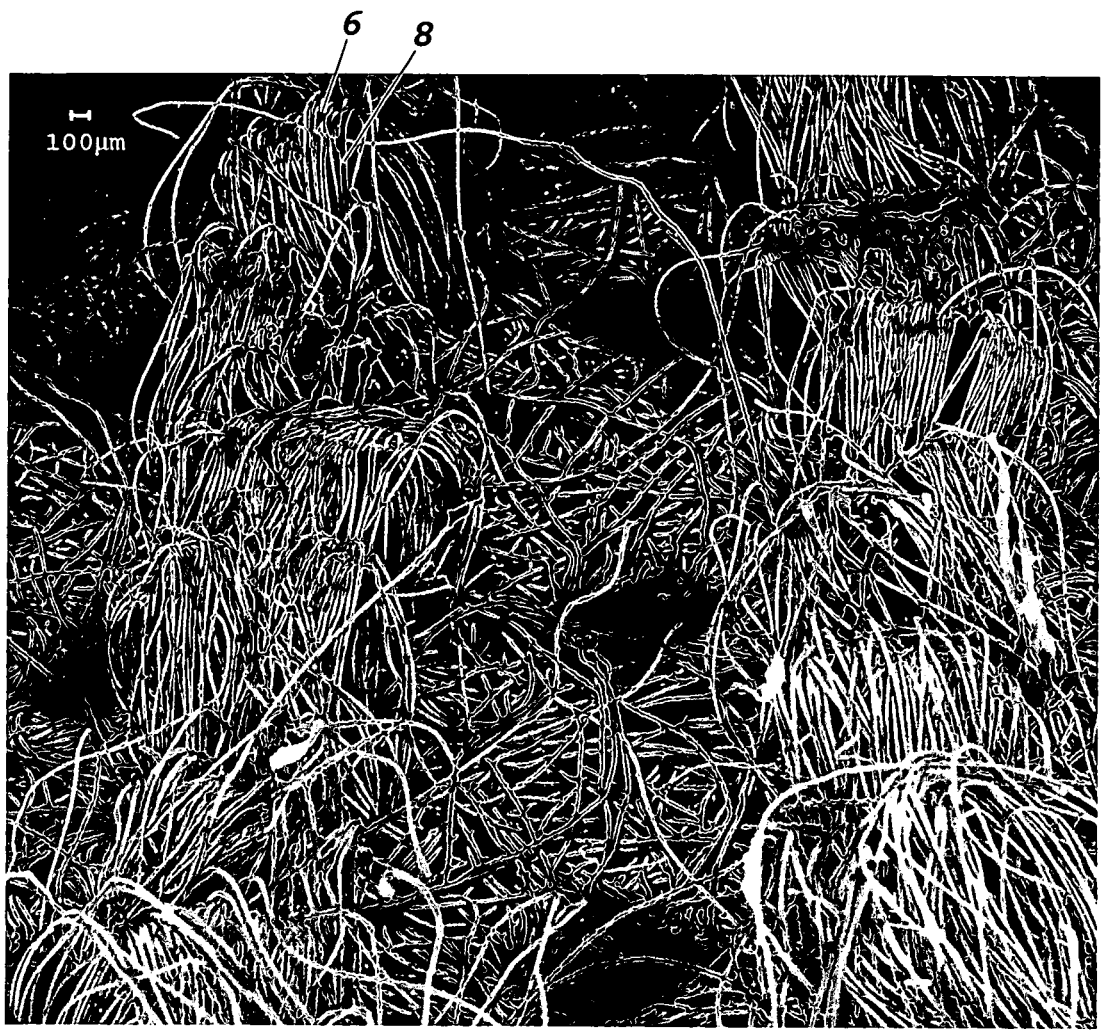
FIG. 5 is a photomicrograph of a portion of a web of the present invention.

FIG. 5 is a scanning electron microscope (SEM) photo of a web 1 similar to that described with respect to FIG. 1. The web 1 of FIG. 5 is a 70 gsm spunbond fibrous, non-woven web comprising polyethylene/polypropylene (sheath/core) bicomponent fibers. The perspective of FIG. 5 is essentially a side view of the first surface 2 and deformations 6 of web 1. By "side view" is meant that the photo of FIG. 5 is taken generally in the CD direction as indicated in FIGS. 1-4, such that the MD and longitudinal axes L of each deformation 6 are oriented across (e.g., from right to left) in FIG. 5. As shown in FIG. 5, deformations 6 comprising looped aligned fibers 8 are aligned generally orthogonal to the longitudinal axis L and have at least a significant vector component parallel to transverse axis T.

Figure 6:
FIG. 6 is a photomicrograph of a portion of the web of FIG. 5.

In some embodiments, due to the preferred method of forming deformations 6, as described below, another characteristic of deformations 6 is their generally open structure characterized by open void area 10, See FIGS. 2 and 3, defined interiorly of deformations 6. The void area 10 may have a shape that is wider or larger at the distal 3 end of deformation 6 and narrower at the base 5 of the deformation 6. This shape is opposite to the shape of the tooth which is used to form the deformation 6. By "void area" is not meant completely free of any fibers, but is meant as a general description of its general appearance. Therefore, it may be that in some deformations 6 a loose fiber 8 or a plurality of loose fibers 8 may be present in the void area 10. By "open" void area is meant that the two longitudinal ends of deformation 6 are generally open and free of fibers, such that deformation 6 forms something like a "tunnel" structure, as shown in FIG. 3. For example, FIG. 6 is a close-up SEM view of one deformation 6 of the web 1 shown in FIG. 5. As shown, in addition to the looped aligned fibers 8 there is a distinct open void area 10 defined by a plurality of looped aligned fibers 8. Very few broken fibers 18 are visible. As can be seen, the base 5 of the deformation 6 may be closed (as in the fibers forming the deformation 6 are close enough together to touch) or may remain open. Generally, any opening at the base 6 is narrow.

Additionally, as a consequence of a preferred method of making web 1, the second regions 4 associated with second surface 14 are discontinuities 16 characterized by a generally linear indentation defined by formerly random fibers of the second surface 14 having been urged directionally (i.e., the "Z-direction" as is commonly understood in the fibrous, non-woven web art to indicate an "out-of-plane" direction generally orthogonal to the MD-CD plane as shown in FIGS. 1 and 3) into deformation 6 by the teeth of the forming structure, described in detail below. The abrupt change of orientation exhibited by the previously randomly oriented fibers of precursor web 20 defines the discontinuity 16, which exhibits a linearity such that it can be described as having a longitudinal axis generally parallel to longitudinal axis L of the deformation 6. Due to the nature of many fibrous, non-woven webs useful as precursor webs 20, discontinuity 16 may not be as distinctly noticeable as deformations 6, for example. For this reason, the discontinuities 16 on the second side of web 1 can go unnoticed and may be generally undetected unless web 1 is closely inspected. Thus in some embodiments, web 1 has the look and feel of terry cloth in some embodiments, web 1 has the look and feel of terry cloth on a first side, and a relatively smooth, soft look and feel on a second side.

Further, as a consequence of a preferred method of making web 1, whether or not the second regions 4 have looped aligned fibers 8, each precursor web exhibits a pronounced linearity at or near the first and second surfaces 12, and 14, respectively, of web 1. As disclosed more fully below with respect to the method of making, one can appreciate that, due to the geometry of teeth 110 of roll 104 of FIG. 7, the deformations 6 and their corresponding discontinuities 16 of second regions 4 of precursor web 20 each have a linear orientation associated therewith. This linear orientation is an inevitable consequence of the method of making web 1 as described herein. One way of understanding this linear orientation is to consider the linear orientation of discontinuities 16 on the second surface 14 of web 1. Likewise, if deformation 6 were excised from web 1 at first surface 12, the second region 4 would appear as a linear discontinuity on the first surface 12 of web 1, e.g., as if a linear slit or cut had been made in precursor web 20 at the location of deformation 6. This linear web discontinuity corresponds directionally to longitudinal axis L.

From the description of web 1, it can be seen that the looped fibers 8 of deformation 6 can originate and extend from either the first surface 12 or the second surface 14 of web 1. Of course the fibers 8 of deformation 6 can also extend from the interior 18 of web 1. The fibers 8 of deformations 6 extend due to having been urged out of the generally two-dimensional plane of precursor web 20 (i.e., urged in the "Z-direction" as shown in FIG. 3). In general, the fibers of the second regions 4 comprise fibers that are integral with and extend from the fibers of the fibrous web first regions 2.

Therefore, from the above description, it is understood that in one embodiment web 1 can be described as being a fibrous web 1 having a first surface 12 and a second surface 14, the fibrous web 1 comprising a first region 2 and a plurality of discrete integral second regions 4, the second regions 4 having at least one portion being a discontinuity 16 exhibiting a linear orientation and defining a longitudinal axis L and at least another portion being a deformation 6 comprising a plurality of tufted fibers integral with but extending from the first region 2.

The extension of looped fibers 8 is can be accompanied by a general reduction in fiber cross sectional dimension (e.g., diameter for round fibers) due to plastic deformation of the fibers and the effects of Poisson's ratio. Therefore, the fibers 8 of deformation 6 can have an average fiber diameter less than the average fiber diameter of the fibers of precursor web 20 as well as the fibers of first regions 2, specifically; it is the portion of the fibers in the loop, between the distal and proximal portions, which exhibits the reduction in fiber diameter. The same fiber also exists in the first region, and has at that point the original fiber diameter. It is believed that this reduction in fiber diameter can contribute to a perceived softness or texture of the web 1, a softness that can be comparable to cotton terry cloth, depending on the material properties of the precursor web 20. It has been found that the reduction in fiber cross-sectional dimension is greatest intermediate the base 5 and the distal portion 3. This is believed to be due to the method of making, as disclosed more fully below. Briefly, portions of fibers at the base 5 and distal portion 3 of deformations 6 are adjacent the tip of teeth 110 of roll 104, described more fully below, and are frictionally locked and immobile during processing. Thus, the intermediate portions of deformations 6 are more free to stretch, or elongate, and accordingly more free to experience a corresponding fiber cross sectional dimension reduction.

Figure 7:
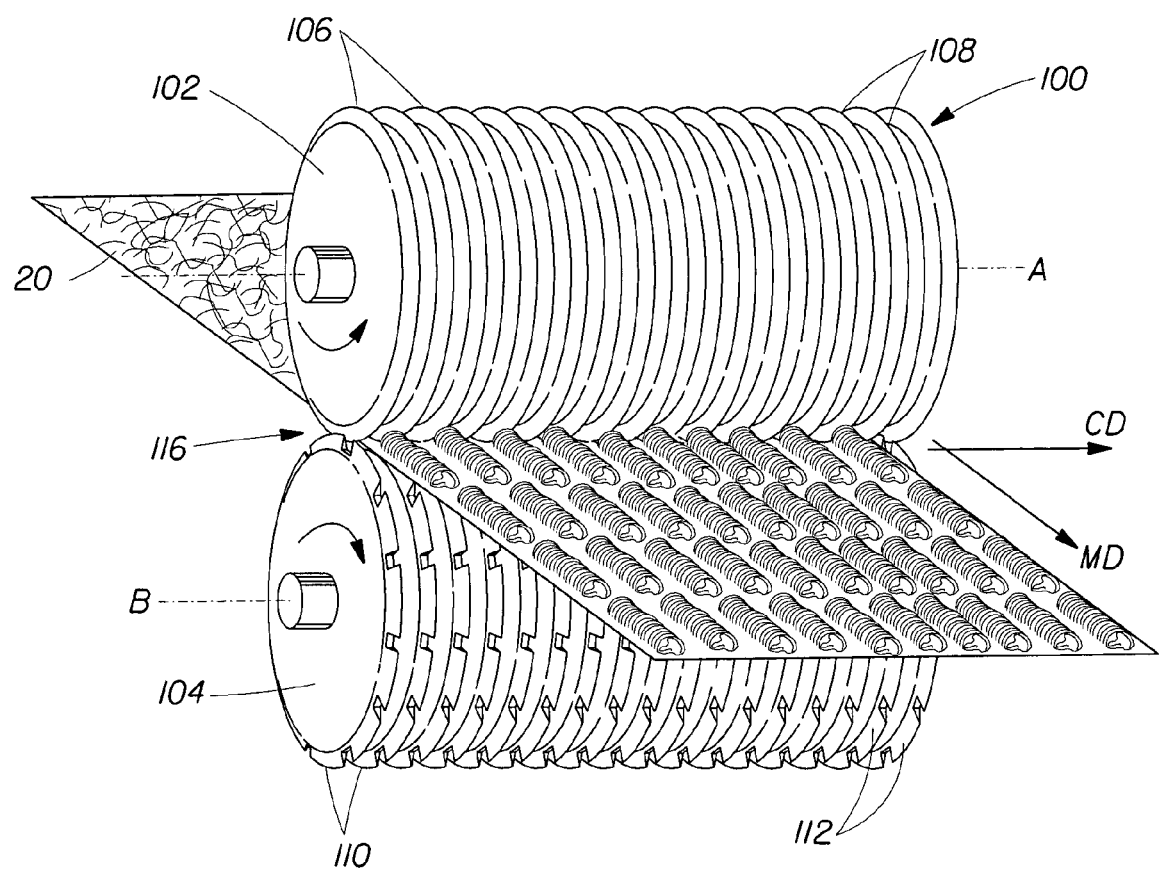
FIG. 7 is a perspective view of an apparatus for forming the web of the present invention.

It can be appreciated that a suitable preferred precursor web 20 for a web 1 of the present invention should comprise fibers capable of experiencing sufficient plastic deformation and tensile elongation such that looped fibers 8 are formed. However, it is recognized that a certain percentage of fibers urged out of the plane of the first surface 12 of precursor web 20 will not form a loop, but instead will break and form loose ends. Such fibers are shown as loose fiber ends 18 in FIGS. 2 and 3. Referring to FIG. 7 there is shown in an apparatus and method for making web 1 of the present invention. The apparatus 100 comprises a pair of intermeshing rolls 102, rotating around Axis A, and 104, rotating around axis B, the axes A being parallel in the same plane. Roll 102 comprises a plurality of ridges 106 and corresponding grooves 108 which extend unbroken about the entire circumference of roll 102. Roll 104 is similar to roll 102, but rather than having ridges that extend unbroken about the entire circumference, roll 104 comprises a plurality of rows of circumferentially-extending ridges that have been modified to be rows of circumferentially-spaced teeth 110 that extend in spaced relationship about at least a portion of roll 104. The individual rows of teeth 110 of roll 104 are separated by corresponding grooves 112. In operation, rolls 102 and 104 intermesh such that the ridges 106 of roll 102 extend into the grooves 112 of roll 104 and the teeth 110 of roll 104 extend into the grooves 108 of roll 102. The intermeshing is shown in greater detail in the cross sectional representation of FIG. 8, discussed below. Both by means or either of rolls 102 and 104 can be heated known in the art such as hot oil filled rollers, or electrically-heated the rollers.

In FIG. 7, the apparatus 100 is shown in a preferred configuration having one patterned roll, e.g., roll 104, and one non-patterned grooved roll 102. However, in certain embodiments it may be preferable to use two patterned rolls 104 having either the same or differing patterns, in the same or different corresponding regions of the respective rolls. Such an apparatus can produce webs with deformations protruding from both sides of the web 1.

The method of making a web 1 of the present invention in a commercially viable continuous process is depicted in FIG. 7. Web 1 is made by mechanically deforming a precursor web 20 that can be described as generally planar and two dimensional. By "planar" and "two dimensional" is meant simply that the web is flat relative to the finished web 1 that has distinct, out-of-plane, Z-direction three-dimensionality imparted due to the formation of second regions 4. "Planar" and "two-dimensional" are not meant to imply any particular flatness, smoothness or dimensionality.

Precursor web 20 is provided either directly from a web making process or indirectly from a supply roll (neither shown) and moved in the machine direction to the nip 116 of counter-rotating intermeshing rolls 102 and 104. Without being bound by theory, Precursor web can be a nonwoven web comprising any of known fiber types, including mono-component, bicomponent, and/or biconstituent, capillary channel fibers, hollow fibers, shaped or lobed fibers and can have major cross-sectional dimensions (e.g., diameter for round fibers) ranging from 5-500 microns. Precursor web 20 can be preheated by means known in the art, such as by heating over oil-heated rollers. Furthermore, precursor web can be a fibrous, non-woven web made by known processes, such as meltblown, spunbond, and bonded carded web processes. As precursor web 20 goes through the nip 116 the teeth 110 of roll 104 enter grooves 108 of roll 102 and simultaneously urge fibers out of the plane of plane of precursor web 20 to form deformations 6. In effect, teeth 110 "push" or "punch" through precursor web 20. As the tip of teeth 110 push through precursor web 20 the portions of fibers that are oriented predominantly in the CD and across teeth 110 are urged by the teeth 110 out of the plane of precursor web 20 in the Z-direction until the fibers either stretch or plastically deform or break, resulting formation of second region 4, including the looped fibers 8 of deformations 6 of web 1. Fibers that are predominantly oriented generally parallel to the longitudinal axis L, i.e., in the machine direction of precursor web 20 as shown in FIG. 1, are simply spread apart by teeth 110 and remain substantially in the first region 2 of web 1. Although, as discussed more fully below, it has been found that the rate of formation of deformations 6 affects fiber orientation, in general, and at least at low rates of formation, it can be understood why the looped fibers 8 can exhibit the unique fiber orientation which is a high percentage of fibers having a significant or major vector component parallel to the transverse axis T of deformation 6, as discussed above with respect to FIGS. 3 and 4. In general, at least some of the fibers of deformation 6 are looped, aligned fibers 8 which can be described as having a significant or major vector component parallel to a Z-oriented plane orthogonal to transverse axis T.

The number, spacing, and size of deformations 6 can be varied by changing the number, spacing, and size of teeth 110 and making corresponding dimensional changes as necessary to roll 104 and/or roll 102. This variation, together with the variation possible in precursor webs 20 and line speeds, permits many varied webs 1 to be made for many purposes.

Figure 8:
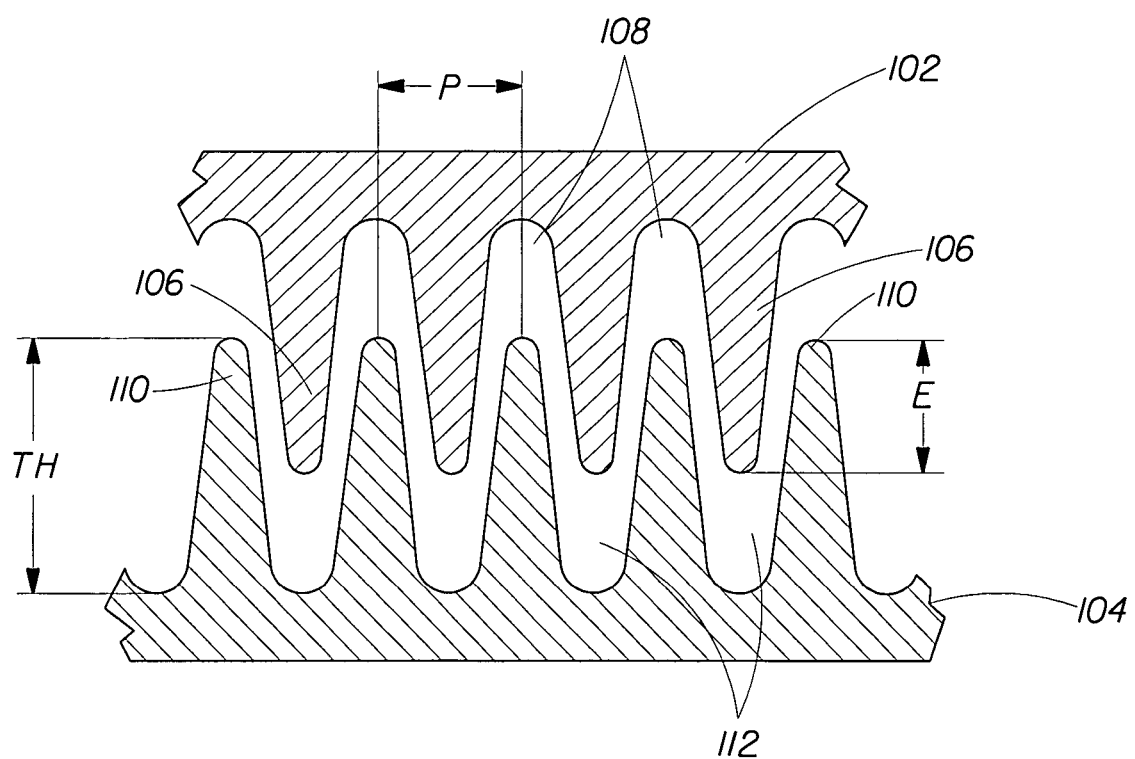
FIG. 8 is a cross-sectional depiction of a portion of the apparatus shown in FIG. 7.

FIG. 8 shows in cross section a portion of the intermeshing rolls 102 and 104 and ridges 106 and teeth 110. As shown teeth 110 have a tooth height TH (note that TH can also be applied to ridge height; in a preferred embodiment tooth height and ridge height are equal), and a tooth-to-tooth spacing (or ridge-to-ridge spacing) referred to as the pitch P. As shown, depth of engagement E is a measure of the level of intermeshing of rolls 102 and 104 and is measured from tip of ridge 106 to tip of tooth 110. The depth of engagement E, tooth height TH, and pitch P can be varied as desired depending on the properties of precursor web 20 and the desired characteristics of web 1. For example, in general, the greater the level of engagement E, the greater the necessary elongation characteristics the fibers of precursor web 20 should possess if predominantly looped deformations are desired. Also, the greater the density of second regions 4 desired (second regions 4 per unit area of web 1), the smaller the pitch should be, and the smaller the tooth length TL and tooth distance TD should be, as described below.

Figure 9:
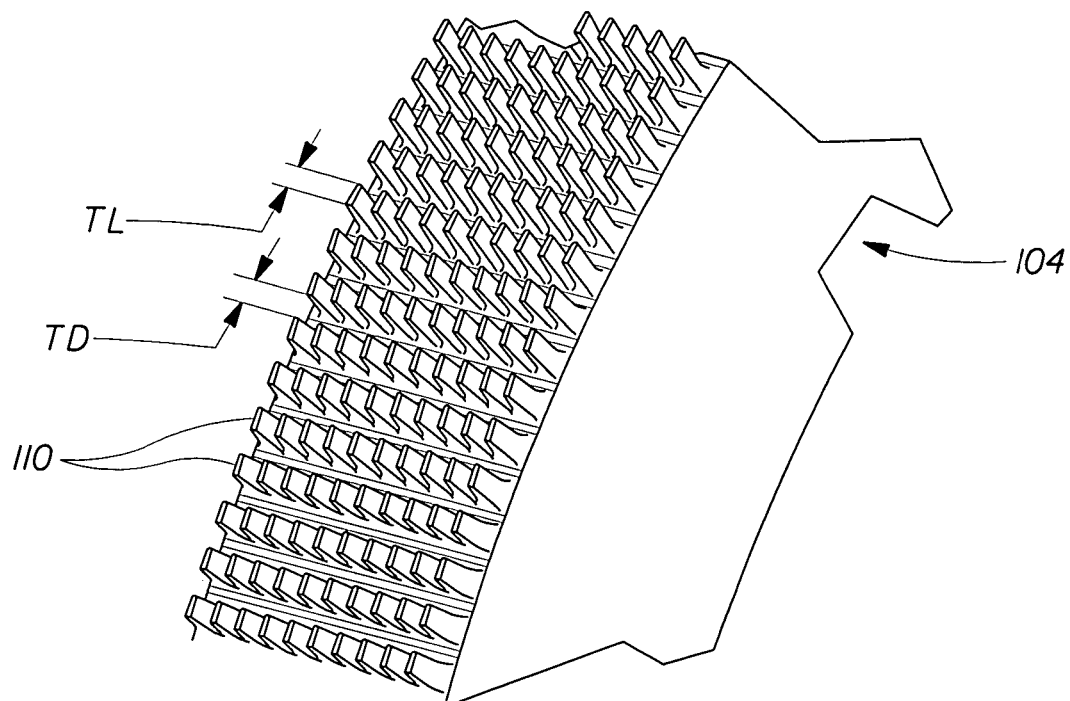
FIG. 9 is a perspective view of a portion of the apparatus for forming one embodiment the web of the present invention.
Figure 10:
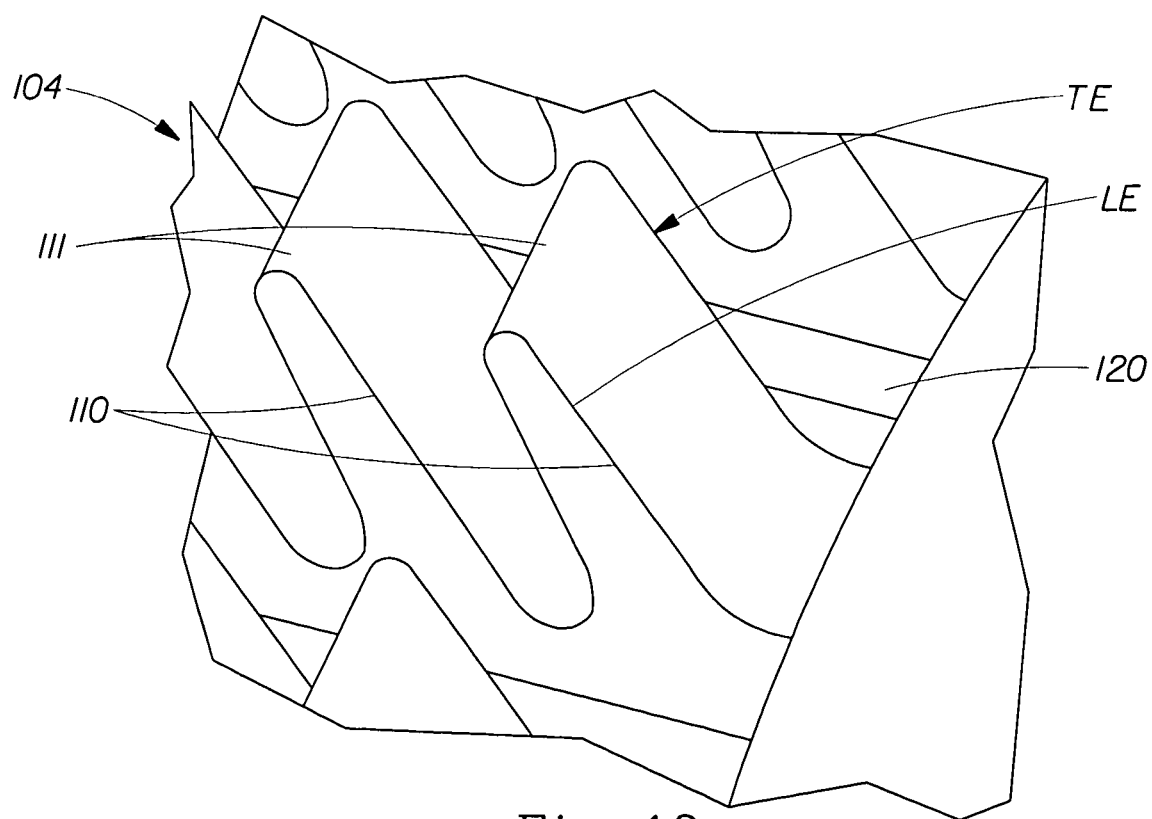
FIG. 10 is an enlarged perspective view of a portion of the apparatus for forming the web of the present invention.

FIG. 9 shows one embodiment of a roll 104 having a plurality of teeth 110 useful for making a terry cloth-like web 1 of spunbond fibrous, non-woven web material from a precursor web 20 having a basis weight of between about 60 gsm and 100 gsm, preferably about 80 gsm. An enlarged view of teeth 110 is shown in FIG. 10. In this embodiment of roll 104 teeth 110 have a uniform circumferential length dimension TL measured generally from the leading edge LE to the trailing edge TE at the tooth tip 111 of about 1.25 mm and are uniformly spaced from one another circumferentially by a distance TD of about 1.5 mm. For making a terry-cloth web 1 from a precursor web 20 having a basis weight in the range of about 60 to 100 gsm, teeth 110 of roll 104 preferably have a length TL ranging from about 0.5 mm to about 3 mm and a spacing TD from about 0.5 mm to about 3 mm, a tooth height TH ranging from about 0.5 mm to about 10 mm, and a pitch P between about 1 mm (0.040 inches) and 2.54 mm (0.100 inches). Depth of engagement E can be from about 0.5 mm to about 5 mm (up to a maximum equal to tooth height TH). Of course, E, P, TH, TD and TL can be varied independently of each other to achieve a desired size, spacing, and area density of deformations 6 (number of deformations 6 per unit area of web 1).

As shown in FIG. 10, each tooth 110 has a tip 111, a leading edge LE and a trailing edge TE. The tooth tip 111 is elongated and has a generally longitudinal orientation, corresponding to the longitudinal axes L of second regions 4. It is believed that to get the tufted, looped deformations 6 of the web 1 that can be described as being terry cloth-like, the LE and TE should be very nearly orthogonal to the local peripheral surface 120 of roll 104. As well, the transition from the tip 111 and LE or TE should be a sharp angle, such as a right angle, having a sufficiently small radius of curvature such that teeth 110 push through precursor web 20 at the LE and TE. Without being bound by theory, it is believed that having relatively sharply angled tip transitions between the tip of tooth 110 and the LE and TE permits the teeth 110 to punch through precursor web 20 "cleanly", that is, locally and distinctly, so that the resulting web 1 can be described as "tufted" in second regions 4 rather than "embossed" for example. When so processed, the web 1 is not imparted with any particular elasticity, beyond what the precursor web 20 may have possessed originally.

It has been found that line speed, that is, the rate at which precursor web 20 is processed through the nip of rotating rolls 102 and 104, and the resulting rate of formation of deformations 6, impacts the structure of the resulting deformations 6. For example, the deformations 6 shown in FIGS. 5 and 6 were made at a relatively low rate of approximately 3 meters per minute (m/min) (about 10 feet per minute). Three m/min is considered a relatively slow rate for commercial production for many consumer applications, but for the spun bond, bicomponent fibers used in the fibrous, non-woven web shown in FIGS. 5 and 6 this relatively slow speed results in very uniform, looped, aligned fibers in deformations 6.

Figure 11:
FIG. 11 is a photomicrograph of a portion of a web of the present invention.
Figure 12:
FIG. 12 is a photomicrograph of a portion of a web of the present invention.

At higher line speeds, i.e., relatively higher rates of processing through the nip of rotating rolls 102 and 104, like materials can exhibit very different structures for deformations 6, i.e., tufts. For example, FIGS. 11 and 12 show representative deformations 6 for webs 1 made from the same material with the same process conditions, the only difference being the rotational speed of the rolls 102 and 104, i.e., line speed (in units of length/time) of the precursor web 20 being processed into web 1. The web shown in FIGS. 11 and 12 is a 25 gsm available from BBA Fibrous, non-woven webs, Simpsonville, S.C., and sold under the trade name Softspan 200®. The web shown in FIG. 11 was processed through the nip 116 of rolls 102 and 104 having a depth of engagement E of about 3.4 mm (about 0.135 inch), a pitch P of 0.060 in., a tooth height TH of 0.154 in, a tooth distance of TD of 0.0625 in., and a tooth length of TL of 0.050 in. The web was run at a line speed of about 15 meters/minute (about 50 feet per minute). The web shown in FIG. 12 is identical to the web shown in FIG. 11, and was processed under identical conditions except for the line speed, which was about 150 meters per minute (about 500 feet per minute).

As can be seen from an inspection of FIGS. 11 and 12, the deformations 6 shown are noticeably different. The deformation 6 shown in FIG. 11 is similar in structure to the deformations shown in FIGS. 1-6. That is, it exhibits substantially aligned, looped fibers 8 with very few broken fibers, e.g., fibers 18 as shown in FIG. 3. The deformation 6 shown in FIG. 12, however, exhibits a very different structure, a structure that appears to be typical of spunbond fibrous, non-woven web materials processed to form deformations 6 at relatively high speeds. Typical of this structure is broken fibers between the proximal portion, i.e., base 5, of deformations 6 and the distal portion, i.e., the top, of deformations 6, and what appears to be a "mat" 7 of fibers at the top of the deformation 6. Mat 7 comprises and is supported at the top of deformations 6 by unbroken, looped fibers 8, and also comprises portions of broken fibers 11, that are no longer integral with precursor web 20. That is, mat 7 comprises fiber portions which were formerly integral with precursor web 20 but which are completely detached from precursor web 20 after processing at sufficiently high line speeds in the process described with reference to FIGS. 7 and 8.

Therefore, from the above description, it is understood that in one embodiment web 1 can be described as being a fibrous web 1 having a first surface 12 and a second surface 14, the fibrous web 1 comprising a first region 2 and a plurality of discrete second regions 4, the second regions 4 having at least one portion being a discontinuity 16 exhibiting a linear orientation and defining a longitudinal axis L and at least another portion being a deformation 6, the deformation 6 comprising fibers integral with but extending from first region 2 and fibers neither integral with nor extending from first region 2.

Figure 13:
FIG. 13 is a photomicrograph of a portion of a web of the present invention.
Figure 14:
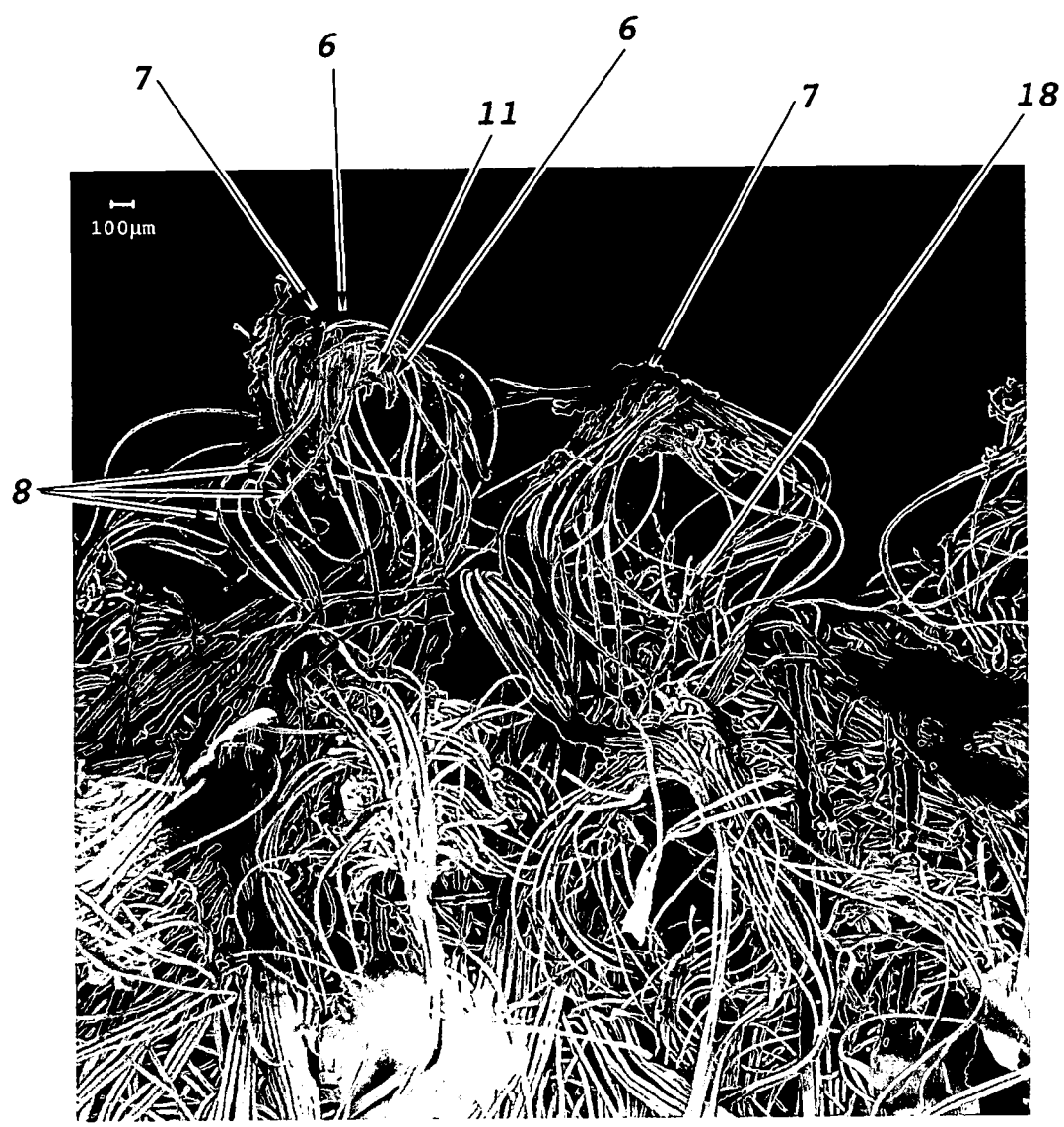
FIG. 14 is a photomicrograph of a portion of a web of the present invention.

Another example of webs 1 being identical in material and processing except for line speed is shown with respect to FIGS. 13 and 14. The precursor web 20 for each web 1 shown in FIGS. 13 and 14 was a 60 gsm DAPP (Ductile Oriented Polypropylene) available from BBA Fibrous, non-woven web s, Simpsonville, S.C., and sold under the trade name Softspan 200®. The web shown in FIG. 13 was processed through the nip 116 of rolls 102 and 104 having a depth of engagement E of about 3.4 mm (about 0.135 inch), a pitch P of 0.060 in., a tooth height TH of 0.145 in., a tooth distance of TD of 0.0625 in., and a tooth length of TL of 0.050 in. The web was run at a line speed of about 15 meters/minute (about 50 feet per minute). The web shown in FIG. 14 is identical to the web shown in FIG. 13, and was processed under identical conditions except for the line speed, which was about 150 meters per minute (about 500 feet per minute).

The web 1 shown in FIG. 13 was processed at a line speed of about 15 meters per minute (about 50 feet per minute). As shown, even at this relatively moderate line speed, some amount of matting at the distal end of deformation 6 is noticed. This matting, which appears to be a higher density of flattened, compressed fiber portions, occurs on the portion of deformation 6 associated with the tip of tooth 110 of roll 104. As line speed is increased, this matting, i.e., mat 7, becomes more distinct, as shown in FIG. 14, which shows a web processed under identical conditions as the web shown in FIG. 13, but was processed at a line speed of about 150 meters per minute (about 500 feet per minute). The deformations 6 shown in FIG. 14 exhibit a more distinct mat 7 and can be described as comprising fibers integral with but extending from first region 2 and fibers neither integral with nor extending from first region 2.

It is believed that the distinct fiber orientation observed at the distal portion of deformations 6, e.g., mat 7, is due primarily to processing rates, it is also believed to be affected by other parameters, such as fiber type, basis weight of the precursor web 20 as well as processing temperatures that can affect the of fiber-to-fiber bonding For example, as observed above, matting of fibers occurs on the portion of deformation 6 associated with the tip of tooth 110 of roll 104. It is believed that frictional engagement of the fibers at the tip of the teeth "lock" the fibers in place, thereby limiting fiber elongation and/or fiber mobility, two mechanisms believed to permit formation of deformations 6. Therefore, once locked, so to speak, in position, fibers adjacent tooth 110 tip can be broken, and, due to the random entanglement of the precursor web as well as possible cold fusion of fibers due to pressure and friction, the broken fibers become and remain lodged in mat 7 at the distal end of deformations 6.

Precursor webs 20 having relatively higher basis weights generally have relatively more fiber portions in mat 7. In one sense, it appears as is as if most of the fiber content of the precursor web is simply displaced in the Z-direction to the distal portion of deformations 6, resulting in mat 7. Precursor webs 20 comprising relatively low elongation fibers, or fibers with relatively low fiber-to-fiber mobility (e.g., fiber reptation) appear to result in relatively few fibers becoming and remaining lodged in mat 7 at the distal end of deformations 6. Fiber-to-fiber mobility can be increased reducing or eliminating the fiber-to-fiber bonds. Thermal bonds can be completely eliminated, or significantly reduced in certain nonwoven webs to increase fiber-to-fiber mobility. Similarly, hydroentangled web can be less entangled to increase fiber-to-fiber mobility. For any precursor web 20 lubricating it prior to processing as disclosed herein can also increase fiber-to-fiber mobility. For example, a surfactant or mineral oil lubricant can be applied to precursor web 20 prior to it entering the nip 116 of rolls 102 and 104.

The result of the presence of mats 7 is a slightly rougher, textured web 1 useful, for example, for wipes in which more scrubbing texture is desirable. In one sense a web having soft terry cloth-like tactile impression under relatively low-speed processing, can have the feel of a cheap hotel towel when processed under identical, but relatively higher speed conditions. This rough, textured tactile impression can be useful for some applications, such as for a hard surface cleaning wipe, an exfoliating facial wipe, and a skin cleansing wipe.

Figure 15:
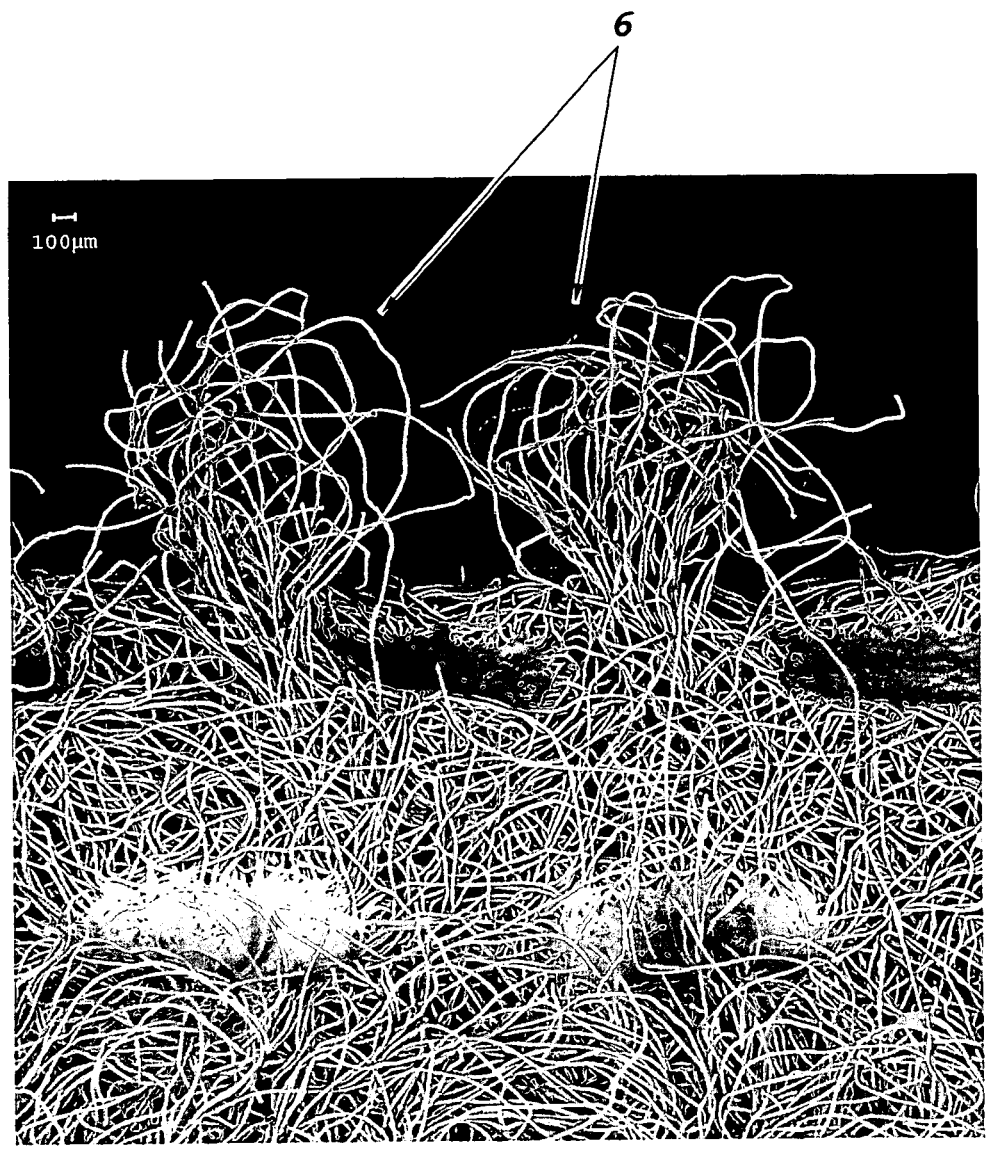
FIG. 15 is a photomicrograph of a portion of a web of the present invention.

It has been found that certain bonded carded webs comprising staple-length fibers produce very few looped fibers 8 in deformations 4, so that the deformations 6 produced in these webs cannot be described as comprising a plurality of looped, aligned fibers 8 as described above with respect to FIGS. 1-6. Instead, as shown in the SEM photograph of FIG. 15, carded fibrous, non-woven webs can produce deformations 6 having few, if any, looped, aligned fibers 8, and many, if not all, non-aligned fibers and/or broken fibers 18. The precursor web 20 used to make the web 1 shown in FIG. 15 was a 40 gsm carded web available from BBA Nonwovens, Simpsonville, S.C., as High Elongation Carded (HEC®) and was processed through the nip 116 of rolls 102 and 104 having a depth of engagement E of about 3.4 mm (about 0.135 inch), a pitch P of about 1.5 mm (about 0.060 inch), a tooth height TH, of about 3.7 mm (about 0.145 inch), a tooth distance of TD of about 1.6 mm (about 0.063 inch), and a tooth length of TL of about 1.25 mm (about 0.050 inch). The web was run at a line speed of about 15 meters/minute (about 50 feet per minute). It is believed that the non-alignment of fibers in deformations 6 made from carded webs is due in part to the nature of the fiber content of carded webs. Staple fibers are not "endless," but instead have a predetermined length on the order of 25 mm to about 400 mm, and, more typically from about 40 mm to about 80 mm. Therefore, when a carded web is processed by the apparatus described with respect to FIG. 7, it is believed that there is a much greater likelihood that a loose fiber end will be in the vicinity of a deformation 6 and thus produce a non-looped fiber end in deformation 6.

Therefore, from the above description, it is understood that the web of the present invention need not have looped, aligned fibers, and in one embodiment can be described as being a fibrous web 1 formed by selective mechanical deformation of a precursor web 20 having a first surface 12 and a second surface 14 and comprising substantially randomly-oriented fibers, the fibrous web comprising a first region of substantially randomly-oriented fibers being substantially free of deformation by the selective mechanical deformation, and a plurality of discrete integral second regions, the second regions 4 comprising spaced-apart deformations 6 of the precursor web 20, each of the second regions 4 having at least one portion being a discontinuity 16 exhibiting a linearity and defining a longitudinal axis L and at least another portion comprising a plurality of tufted fibers integral with but extending from said first region.

Webs 1 of the present invention offer many opportunities for producing engineered materials having selected characteristics. For example, a web 1 can be made by selecting the length of staple fibers in a carded precursor web 20 so that the probability of having fiber ends exposed in deformations 6 can be reliably predicted. Also, a carded web of staple fibers can be blended or laminated with a spunbond fibrous, non-woven web to produce a hybrid, such that the deformations 6 of second regions 4 comprise primarily looped spunbond fibers and the first regions 2 comprise both carded and spunbond fibers. The type of fibers, the length of staple fibers, the layering of fibers, and other variations of precursor web 20 can be varied as desired to produce desired functional characteristics of the web 1.

In preferred embodiments precursor web 20 is a fibrous, non-woven web in which there are minimal fiber-to-fiber bonds. For example, the precursor web can be a fibrous, non-woven web having a pattern of discrete thermal point bonds, as is commonly known in the art for fibrous, non-woven webs. Preferred carded thermal bonded webs for the present invention are lightly bonded. As used herein, the term "lightly bonded" means that the nonwoven web has been thermally bonded sufficiently to melt the fusible fibers and provide web integrity for easy handling and transporting, but not enough to heavily bond the web such that the web losses its softness and flexibility. Among carded thermal bonded webs, lightly bonding is preferred for making tufts and loops.

In general, however, it is desirable to minimize the number and spacing of bond points so as to allow for maximum fiber mobility and dislocation at the second regions 4 of web 1. In general, utilizing fibers having relatively high diameters, and/or relatively high extension to break, and/or relatively high fiber mobility, results in better and more distinctly formed second regions 4, specifically deformations 6.

Although web 1 is disclosed in preferred embodiments as a single layer web made from a single layer precursor web 20, it is not necessary that it be so. For example, a laminate or composite precursor web 20 having two or more layers or plies can be used. In general, the above description for web 1 holds, recognizing that looped aligned fibers 8, for example, formed from a laminate precursor web may be comprised of fibers from both (or all) layers of the laminate. In such a web structure, it is important, therefore, that all the fibers of all the layers have sufficient diameter, elongation characteristics, and fiber mobility, so as not to break prior to extension and deformation. In this manner, fibers from all the layers of the laminate may contribute to the tufted deformations 6. In a multilayer web, the fibers of the different webs may be mixed or intermingled in the deformation 6. The fibers do not protrude through but combine with the fibers in an adjacent web. This is often observed when the webs are processed at very high speeds.

Figure 16:
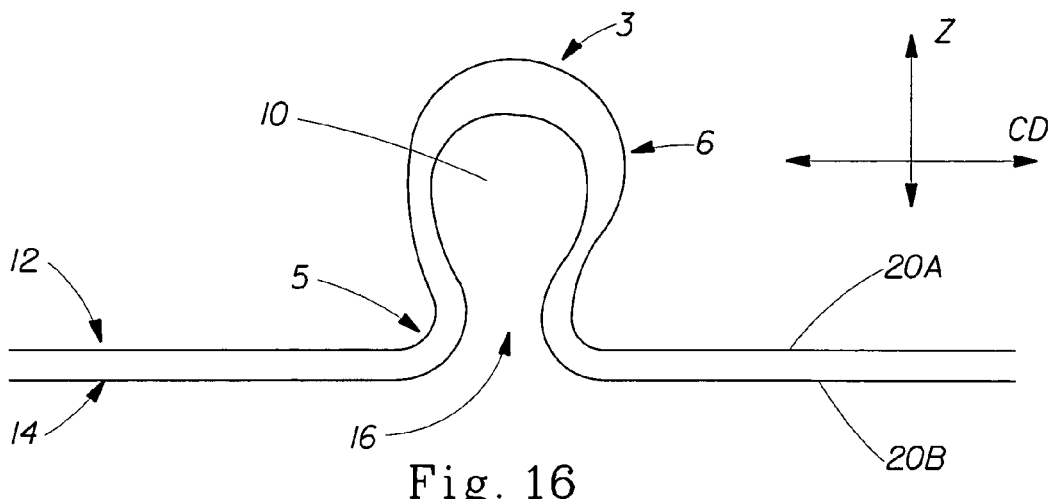
FIG. 16 is a schematic representation of a portion of a web of the present invention.
Figure 17:
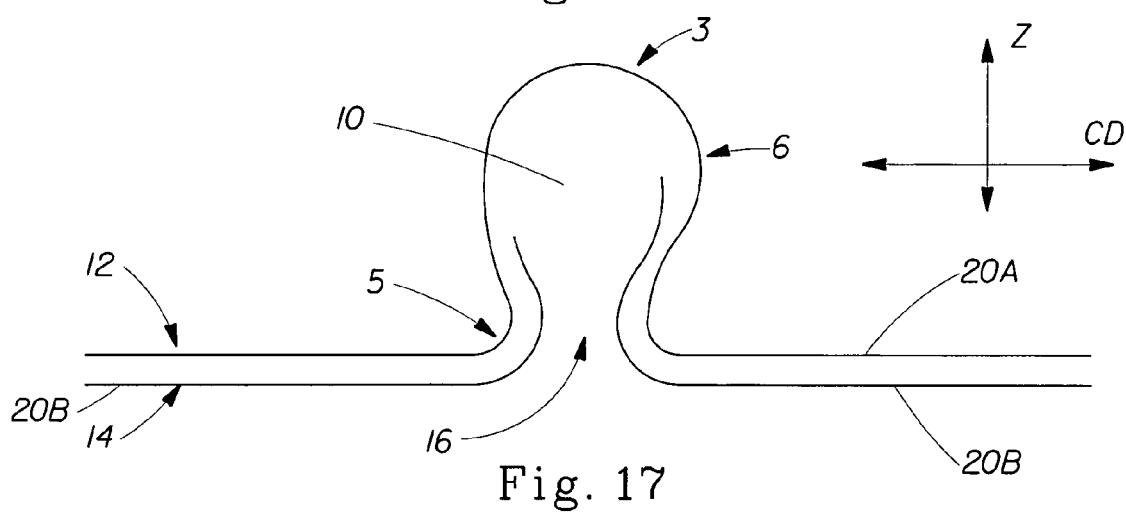
FIG. 17 is another schematic representation of a portion of a web of the present invention.
Figure 18:
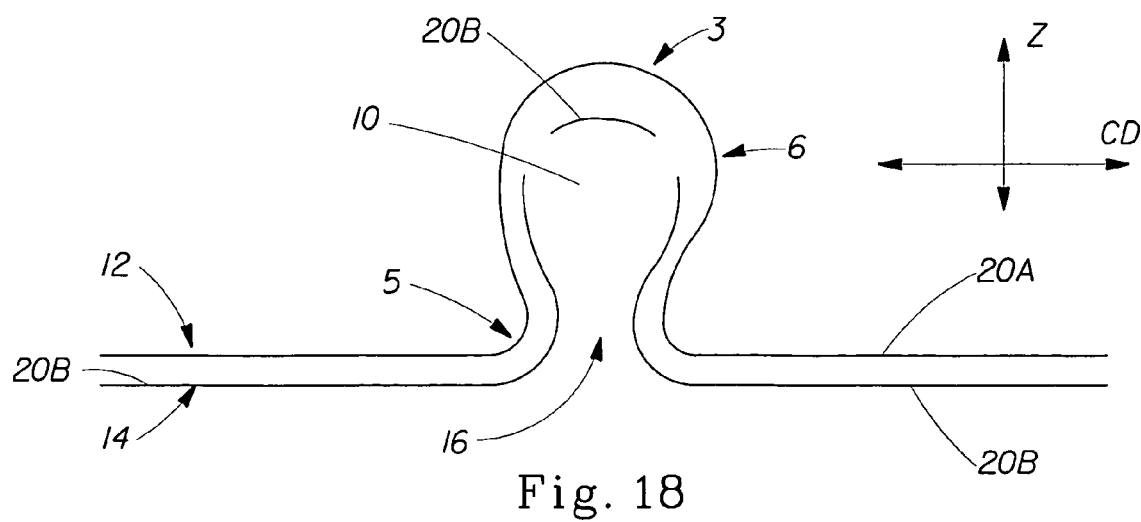
FIG. 18 is another schematic representation of a portion of a web of the present invention

Multilayer webs 1 can have significant advantages over single layer webs 1. For example, a deformation 6 from a multilayer web 1 using two precursor webs 20A and 20B, is shown schematically in FIGS. 16-18. As shown, both precursor webs 20A and 20B contribute fibers to deformations 6 in a "nested" relationship that "locks" the two precursor webs together, forming a laminate web without the use or need of adhesives or thermal bonding between the layers. However, if desired an adhesive, chemical bonding, resin or powder bonding, or thermal bonding between the layers can be selectively utilized to certain regions or all of the precursor webs. In a preferred embodiment, the deformations 6 retain the layered relationship of the laminate precursor web, as shown in FIG. 16, and in all preferred embodiments the upper layer (specifically layer 20A in FIGS. 16-18, but in general the top layer with reference to the Z-direction as shown in FIGS. 16-18) remains substantially intact and forms looped fibers 8 shown in FIG. 2.

In a multilayer web 1 each precursor web can have different properties. For example, web 1 can comprise two (or more) precursor webs, e.g., first and second precursor webs 20A and 20B. First precursor web 20A can form an upper layer exhibiting high elongation and significant elastic recovery which enables the web 20A to spring back. The spring back helps to laterally squeeze the base portion 5 of the deformation 6 of both webs as shown in FIG. 16. The spring back or lateral squeeze also helps to secure and stabilize the Z-oriented fibers in the deformation 6. The lateral squeeze provided by precursor web 20A can also increase the stability of the second precursor web 20B. An example of a multilayer web 1 includes a first precursor web 20A comprised of spunbond PE/PP sheath/core nonwoven web made by BBA, Washougal Wash. The second precursor web 20B is comprised of a thermal point bonded carded PET/Co-PET nonwoven web (50% 6 dpf PET Wellman Type 204 made in Charlotte N.C. and 50% 6 dpf Co-PET Kanematsu Type LM651 made in Gastonia N.C. The second precursor web 20B can be loosely bonded to enable tufting so the lateral squeeze of the first precursor web 20A can also increase the stability of the second precursor web 20B. The multilayer web 1 can be utilized as a body-contacting layer when used as a topsheet on a disposable absorbent article or can be utilized as a lower layer which is disposed between the topsheet and an absorbent core. The multilayer web could also be utilized as an absorbent core.

In a multilayer web 1 each precursor web can have different material properties, thereby providing web 1 with beneficial properties. For example, web 1 comprising two (or more) precursor webs, e.g., first and second precursor webs 20A and 20B can have beneficial fluid handling properties for use as a topsheet on a disposable absorbent article, as described more fully below. For superior fluid handling, for example, first precursor web 20A can form an upper layer (i.e., a body-contacting when used as a topsheet on a disposable absorbent article) and be comprised of relatively hydrophobic fibers. Second precursor web 20B can form a lower layer (i.e., disposed between the topsheet and an absorbent core when used on a disposable absorbent article) comprised of relatively hydrophilic fibers. Fluid deposited upon the upper, relatively hydrophobic layer is quickly transported to the lower, relatively hydrophilic, layer. One reason for the observed rapid fluid transport is the capillary structures formed by the generally aligned fibers 8, 18 of deformations 6. The fibers 8, 18 form directionally-aligned capillaries between adjacent fibers, and the capillary action is enhanced by the general convergence of fibers near proximal portion 5 of deformations 6.

It is believed that the rapid fluid transport is further increased due to the ability of fluid to enter the web 1 via the voids 10 created by deformations 6. This "lateral entry" capability and/or capillary action, and/or the hydrophilicity gradient afforded by the structure of web 1 makes web 1 an ideal material for optimal fluid handling for disposable absorbent articles. In particular, a multilayer web 1 can provide for even greater improvement in fluid handling characteristics.

In another embodiment, first precursor web 20A can be comprised of relatively soft fibers (e.g., polyethylene), while second precursor web 20B can be comprised of relatively stiff fibers (e.g., polyester). In such a multilayer web 1, deformations 6 can retain or recover a certain amount of height h, even after applied pressure.

Depending on the precursor web 20 utilized and the dimensional parameters of rolls 102 and 104, including teeth 110, web 1 of the present invention can exhibit a wide range of physical properties. The web 1 can exhibit a range of texture subjectively experienced as ranging from softness to roughness; an absorbency ranging from non-absorbent to very absorbent; a bulkiness ranging from relatively low bulk to relatively high bulk; a tear strength ranging from low tear strength to high tear strength; an elasticity ranging from non-elastic to at least 100% elastically extensible; a chemical resistance ranging from relatively low resistance to high resistance; depending on the chemical considered, and many other variable parameters generally described as shielding performance, alkali resistance, opacity, wiping performance, water absorptivity, oil absorptivity, moisture permeability, heat insulating properties, weatherability, high strength, high tear force, abrasion resistance, electrostatic controllability, drape, dye-affinity, safety and the like. In general, depending on the elongation properties of the fibers of precursor web 20, the dimensions of apparatus 100 can be varied to produce a web 1 having a wide range of dimensions associated with second regions 4, including the height h (as shown in FIG. 20), and spacing (including area density of discrete second regions 4).

Figure 19:
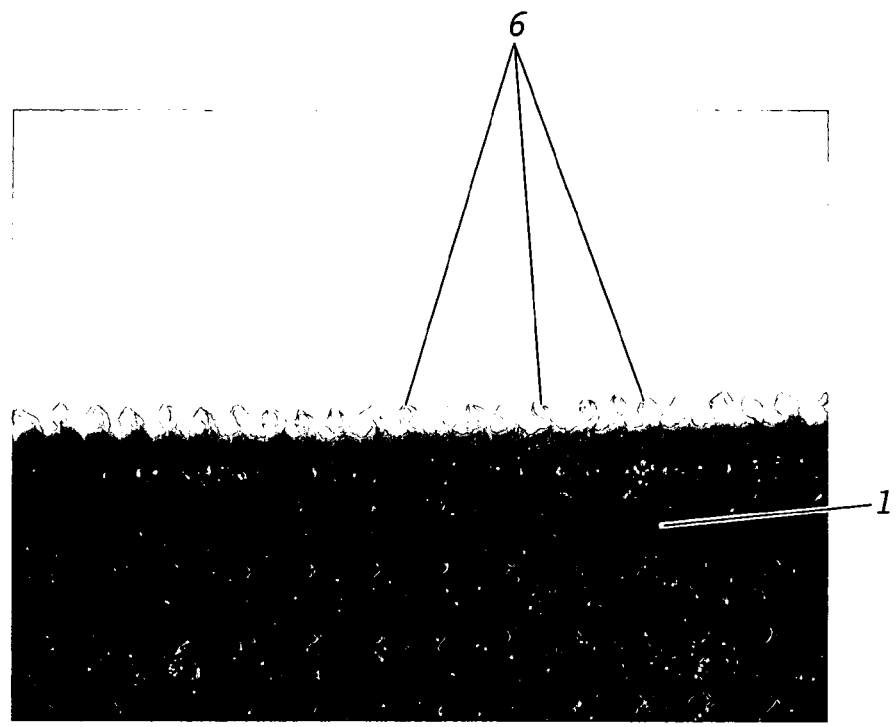
FIG. 19 is a photomicrograph of a portion of a web of the present invention.

FIG. 19 is a photomicrograph of a terry cloth-like fibrous, non-woven web fabric web 1 made by the process of the present invention using a roll 104 as shown in FIGS. 9 and 10 and useful as a component of a disposable, absorbent article. The precursor web 20 used for the web 1 shown in FIG. 19 was a spunbond fibrous, non-woven web having a basis weight of about 80 gsm, and comprising polyethylene/polypropylene (sheath/core) polyethylene/polypropylene (sheath/core) polyethylene/polypropylene (sheath/core) bicomponent fibers having an average diameter of about 33 microns. The web 1 of FIG. 19 has about 24 deformations 6 per square centimeter and is folded with the folded edge visible to show more clearly a plurality of spaced apart, tufted, looped deformations 6 having a plurality of looped, aligned fibers 8, each of which has an average fiber diameter of about 18 microns.

Figure 20:
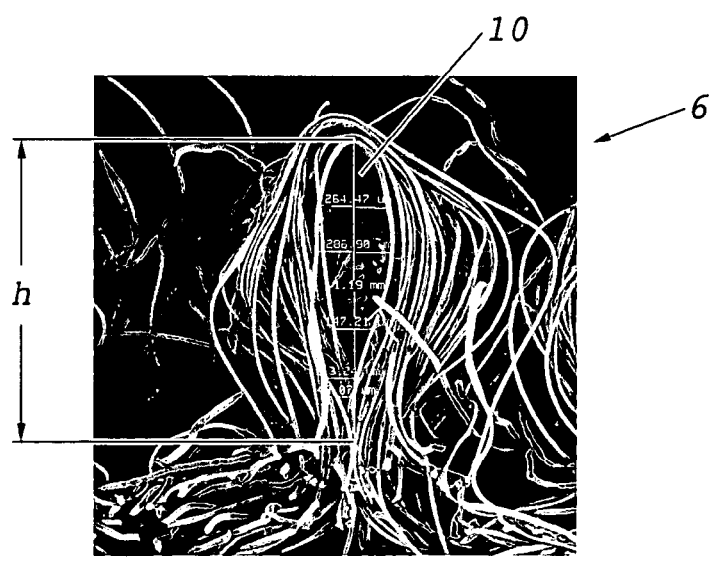
FIG. 20 is an enlarged photograph of a portion of the web shown in FIG. 16.

A single deformation 6 is shown in FIG. 20 with dimensions indicated. As shown in FIG. 10, for the web described with respect to FIG. 20, the void area 10 tufted, looped, deformation 6 is typically generally circular or oblong in shape, having a major dimension, referred to as height h, that can be at least 1 mm. In general, the height is not considered to be critical to the operation of the web, but can be varied depending on the desired end use of web 1. The height h can be from 0.1 mm to about 10 mm or more. A web 1 formed from a fibrous, non-woven web precursor web 20 and having a look and feel of terry cloth should have a height h of about 1 mm to about 3 mm.

Figure 21:
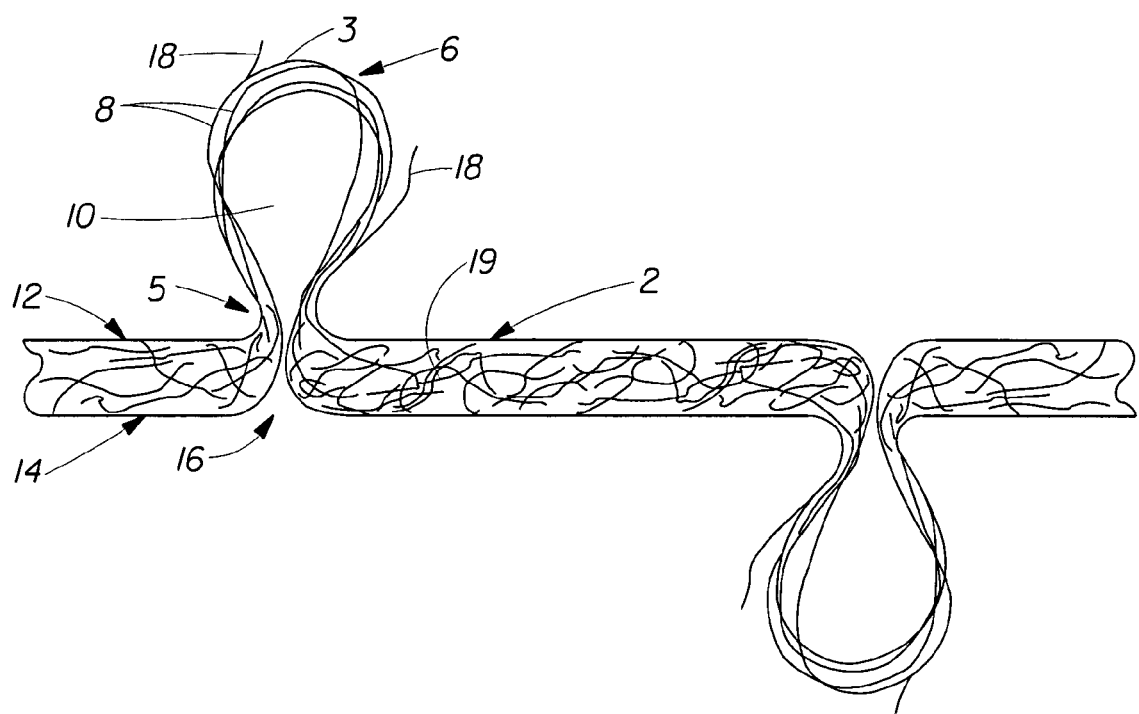
FIG. 21 is a perspective view of a web of the present invention.

An additional embodiment of web 1, shown in FIG. 21, on the side of web 1 associated with first surface 12 of web 1, second region 4 can comprise deformations 6, each deformation 6 comprising a plurality of tufted, aligned fibers 8 extending outwardly from first surface 12. Deformations 6 can be described as "tufts" of fibers, and each deformation 6 has a base 5 proximal to the first surface 12, and a distal portion 3 at a maximum distance from the first surface 12. On the first surface 12 of web 1 a second region 4 can comprise discontinuities 16 which are defined by fiber orientation discontinuities on the first surface 12 of web 1. On the side of web 1 associated with second surface 14, second region 4 can comprise deformations 6, each deformation 6 comprising a plurality of tufted, looped, aligned fibers 8 extending outwardly from second surface 14. Deformations 6 can be described as "tufts" of fibers, and each deformation 6 has a base 5 proximal to the second surface 14, and a distal portion 3 at a maximum distance from the second surface 14. On the second surface 14 of web 1 a second region can comprise discontinuities 16 which are defined by fiber orientation discontinuities on second surface 14 of web 1. Therefore, web 1 can comprise deformation 6 and discontinuities 16 on first surface 12 and second surface 14.

Table 1 below shows representative dimensions for representative apparatus and webs made thereon.

TABLE 1

Examples of Apparatus Dimensional Parameters and Web Dimensions

| Sample No. | Precursor Web | Pitch (P) <mm> (inches) | Engagement (E) <mm> (inches) | Tooth Height (TH) <mm> (inches) | Loop height (h) (mm) | Avg. Fiber Diameter of Precursor Web (μm) | Avg. Fiber Diameter of Loop Fiber (μm) |
|---|---|---|---|---|---|---|---|
| 1 | 80 gsm spunbond PE/PP core/sheath | <1.5> (0.060) | <3.4> (0.135) | <3.7> (0.145) | 1.07 | 33 | 18 |
| 2 | 80 gsm spunbond PE/PP core/sheath | <1.5> (0.060) | <2.2> (0.085) | <3.7> (0.145) | 0.49 | 31 | 23 |
| 3 | 60 gsm spunbond PE/PP copolymer | <1.5> (0.060) | <3.4> (0.135) | <3.7> (0.145) | 1.10 | 23 | 14 |
| 4 | 60 gsm spunbond PE/PP copolymer | <1.5> (0.060) | <3.4> (0.135) | <3.7> (0.145) | 1.41 | 28 | 15 |
| 5 | 60 gsm spunbound PP | <1.5> (0.060) | <3.4> (0.135) | <3.7> (0.145) | 1.0 | 27 | 20 |

In Table 1 above, all Samples are available from BBA Fibrous, non-woven webs, Simpsonville, S.C. Samples 1, and 2, are sold under the trade name Softex®. Samples 3 and 4 are sold under the trade name Softspan 200®.

Method for Characterizing Tufts

A representative portion of a side of a web is selected and a sample of the web is prepared suitable for evaluation by scanning electron microscope (SEM) imaging, which produces an image or photomicrograph, by standard procedures well known to those skilled in the art. Imaging first at a relatively low magnification, about 10×, a field is chosen having tufts. Within the field, several representative tufts are selected and images taken at several viewing angles in order to augment the ability to count fibers contained in the selected tufts. At least a first image is taken of each selected tuft facing in the machine direction at a low angle from the surface, viewing through the open ends of the tuft. At least a second image is obtained at an angle rotated close to 90 degrees from the first image. Magnification is selected to enhance the ability to accurately count and measure the diameter of fibers within the tuft. If a representative portion of the bulk is not visible in the images already obtained, an image of the bulk surface, away from the tuft, is also obtained for comparison. Suitable magnifications typically range from about 10× to about 100× when the images are printed out in 8 in.×10 in. size and measurements taken with a 6 inch caliper. Print the images in 8 in.×10 in. size or larger, which is a photomicrograph. Include a scale bar on each printed image.

Fiber Count

Examine the photomicrographs of a tuft to be counted. Select a photomicrograph of the tuft viewing through the open area of the tuft. If the open area of the tuft is not apparent, select any image that allows the fibers to be counted. The tuft will be composed of fibers rising out of the web surface at one point, some of which may loop over and re-enter the surface at another point. Look for a region of the tuft that readily allows distinction between upward and downward portions of the same fiber, having as few obscured fibers as possible.

Use a pencil, pen or marker to count the number of fibers. Begin from the center of the tuft and count outward toward the edge (or vice versa), moving in roughly a straight line. This minimizes the risk of counting the same fiber more than once. Carefully examine the tuft looking for fibers that missed being counted or were counted twice. Some fibers have been broken. Carefully check to see that the two halves of a broken fiber have not been counted as two separate fibers. Adjust the count accordingly. Count the fibers again, in a second line, in a different direction from the first count. The maximum number of fibers counted is the Total Number of Fibers per Tuft in the tuft. Select an image of the same tuft, from a different angle. Verify the accuracy of the count obtained by counting fibers in the tuft from the second viewing angle, counting across from one side to the other side (e.g., left to right), or along the top of the tuft. If fibers are obscured from one viewing angle, such that the count from a different angle gives a larger number, select the larger number as the number of fibers in the tuft. Make sure to count only individual fibers, and not matted or fused areas such as can occur as the result of processing including optional processing such as heat fusing or cold welding of the tops of the tufts or loops.

Fiber End Count

Count all the visible fiber ends in the tuft. Use a pencil, pen or marker to identify each end as it is counted. This minimizes the risk of counting the same end more than once. Carefully examine the tuft images, looking for ends that missed being counted. Adjust the count accordingly. The result obtained is the Number of Fiber Ends per Tuft. Note that some fibers may pull out of the web surface, exposing only one end, in which case the Number of Fiber Ends per Tuft can be an odd value, not an even value. It is reported as counted regardless of whether the value obtained is odd or even.

Repeat the counting process of Total Number of Fibers per Tuft, and Number of Fiber Ends per Tuft with at least another tuft. Report the average result.

Number of Fibers Per Tuft Not Broken

Calculate the Number of Fibers per Tuft Not Broken (N) by Equation 1.

$$N = \text{Total Number of Fibers per Tuft} - (\text{Number of Fiber Ends per Tuft})/2 \qquad (1)$$

Express the Number of Fibers per Tuft Not Broken as a percentage according to Equation 2.

$$N/\% = 100 \times N/\text{Total Number of Fibers per Tuft} \qquad (2)$$

Fiber Diameter

Visually inspect a photomicrograph of a tuft at a magnification suitable for measuring the width of individual fibers. Inspect the tuft for uniformity of fiber diameter. If fiber diameters seem fairly consistent, choose one fiber that seems representative and set the caliper spacing to the width of that fiber. Compare the caliper spacing with five to ten additional fibers in the tuft to verify the chosen fiber was representative. If most fibers seem larger (or smaller) than the caliper setting, adjust the gap and repeat the comparison. Calculate the actual diameter as the average caliper readings of the 6-11 readings taken, using the scale bar to correct the result and report actual diameter as the average as the results. The result is the Average Diameter of Fibers In Tuft. Similarly, concentrate on the bulk web and visually inspect for uniformity. Determine the representative bulk fiber diameter using the same procedure as for tuft fibers. Average the result and use the scale bar to correct the results to actual dimensions. The result is the Average Diameter of Fibers Ex Tuft. The ratio of the diameters can be easily determined as an indication of the extent of fiber draw.

Tuft Height Tuft Maximum Width, and Tuft Minimum Width

Figure 22:
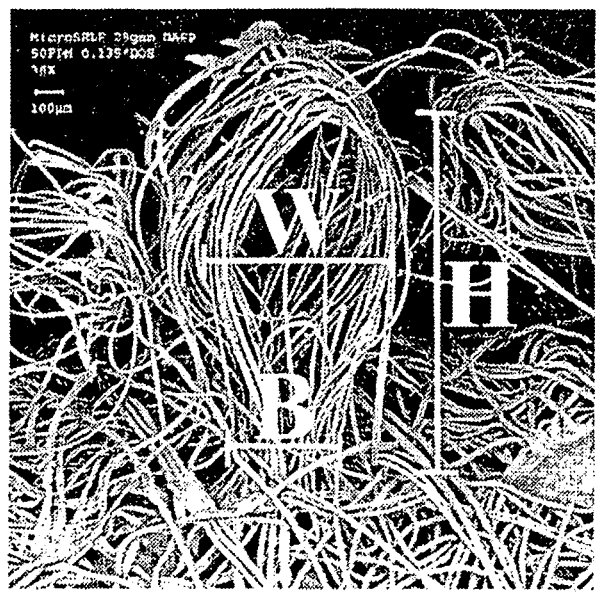
FIG. 22 is a photomicrograph of a portion of a web of the present invention.

Select the same photomicrograph as the first one used to count fibers, viewing through the open portion of the tuft which may also be a loop. In the photomicrograph shown in FIG. 22, Tuft Height is H, Tuft Maximum Width is W, and Tuft Minimum Width is B. Visually inspect the photomicrograph for uniformity of tuft dimension being measured. To measure the Tuft Maximum Width, set the caliper spacing to the width of that tuft at the widest point. Most tufts will have a few random stray fibers that protrude dramatically from the bulk of the tuft. Do not include these fibers within the caliper gap. Compare the caliper spacing with several additional tufts (5-10). Average the results, and use the scale bar to adjust the result to actual dimensions. Follow this same procedure for Tuft Height and Tuft Minimum Width.

Personal Care Articles

Personal care articles of the present invention require, in addition to the fibrous web of the present invention, at least one cleansing and, or treatment composition associated with the fibrous, non-woven web that are useful for cleansing and, or treating the skin, hair, and similar keratinous surfaces of the body. Inventors have discovered that the combined action of the tufted web and the treatment/cleansing component (i.e., composition as part of another composition) associated with the web of the current invention provides an unexpected level of benefits in personal care articles. Without being limited by theory, it is believed that the multitude of fibers oriented orthogonal to the plane of the web, in addition to providing a surface which can advantageously feel soft or textured, provide unique cleansing, exfoliating, treating and/or lathering benefits when combined with treatment compositions of the present invention. Inventors believe the fibers oriented orthogonal to the plane of the web, i.e., the MD CD plane, enhance cleaning action to the skin by intimately scraping skin features such as pores or wrinkles to remove associated soils; wick soils associated with the skin into the cloth by combined scraping and wicking away from the skin surface; entrap particles present on the skin surface which may be contaminants (i.e., "dirt") or simply residue from temporary skin treatments (i.e., particles associated with cosmetics such as facial foundation); apply treatment to the skin by exposing cleaner skin surfaces and/or by wicking treatment compositions from the article of the present invention to the skin; and provide enhanced lather benefit for lathering articles by providing air voids within/around the tufts which promote lather generation when combined with a lathering surfactant component and mechanical agitation.

Personal care articles of the present invention may comprise volatile and non-volatile fluids selected from the group consisting of water, mono- and polyhydric alcohols (glycerin, propylene glycol, ethanol, isopropanol, etc.), hydrocarbon oils such as mineral oil, silicone fluids, also triglyceride oils, also fluid resins such as silicone MQ resins, esters and ethers of hydrocarbons, alcohols, perfume, fragrance oils, natural oils such as terpenes, various tree and plant oils, as well as mixtures of the above and can contain other components dissolved or dispersed within them, or in addition to them.

The articles may also be useful without the addition of fluids or the fluid may be activated, or both. Because of the interaction of the tufted web with the treatment composition, low levels of the treatment component can provide substantial benefit. For example, only about 0.25 grams to about 10 grams of dried surfactant component per square meter of web surface area (0.25-10.0 gsm) can provide a lather benefit useful for facial cleansing. Because of the low density nature of the tufted web, the web is also capable of holding at least about 10 times the weight of the fibrous, non-woven web of a liquid treatment component, useful for wiping onto or delivering to the designated surface a treatment composition. Other uses of the articles of the present invention will become apparent from the examples disclosed herein.

Under certain circumstances, personal care articles of the present invention may appear to not contain deformations, for example in the presence of treatment compositions contained thereon, if a large amount of opaque composition is added to the web of the invention, masking the presence of deformations. For example, a stack of 30 folded, interleaved personal care articles of the current invention, each article containing 500 weight percent by weight of the substrate of a viscous, opaque, therapeutic, semi-solid emulsion may not readily exhibit the tufts and loops contained therein. Masking the presence of deformations in no way diminishes the benefits obtained thereby, and the presence of deformations, i.e., tufts and/or loops, can be verified by first removing the personal care composition from the web of the invention.

Personal Care Compositions

The present invention is for personal care articles used by individuals primarily for cleansing and, or treatment of skin, hair or other and similar keratin-containing surfaces including skin, hair and finger and toe nails. These personal care articles encompass the use of personal care compositions that are embedded or impregnated onto the surface of the fibrous nonwoven web of the present invention. The personal care compositions of the present invention are selected from the group consisting of cleansing compositions and treatment agents and mixtures thereof. The present invention can comprise articles that combine both cleansing compositions and treatment agents into a single article.

I. Cleansing Compositions

A. Lathering Cleansing Compositions

Besides the fibrous, non-woven web, the articles of the present invention also comprise one or more lathering surfactants that are associated with the fibrous, non-woven web or substrate fibrous, non-woven web. Thus the lathering surfactants can be added onto or impregnated into the fibrous, non-woven web. Generally this will be done prior to the point of use of the article, i.e., the surfactants will be combined with the article before the article is ultimately wetted for use. The body cleansing compositions of the present invention comprise a sufficient amount of one or more lathering surfactants such that the articles are capable of generating at least 1400 ml of Total Steady Lather Volume according to the Steady Lather Volume Test described below. The face cleansing compositions of the present invention of the present comprises a sufficient level of surfactant described herein that it generates at least 85 ml of Mechanical Lather Volume, as described in the Mechanical Lather Volume Test described below. The shampoo articles of the present invention comprise sufficient level of a shampoo composition dried on the fibrous, non-woven web.

1) Body Cleansing Composition

The body cleansing compositions are characterized as having lather that lasts for an extended time period, and are most useful for washing a larger surface, i.e. such as washing the entire body during showering. Generally the body cleansing composition will preferably comprise no more than about 1600 weight percent by weight of the web of the lathering surfactant, preferably comprise no more than about 1000 weight percent, more preferably no more than about 800 weight percent, and still more preferably no more than about 600 weight percent by weight of the web of a lathering surfactant. Generally the body cleansing composition will preferably comprise at least 15 weight percent by weight of the web of the lathering surfactant, preferably at least 25 weight percent, more preferably at least 50 weight percent, and still more preferably at least 60 weight percent by weight of the web of a lathering surfactant.

The body cleansing compositions of the present invention comprise a sufficient amount of one or more lathering surfactants such that the compositions are capable of generating at least 1400 ml of Steady Total Lather Volume according to the Steady Lather Volume Test described below. Preferably the body cleansing composition generates at least 1900 ml of Steady Total Lather Volume, even more preferably at least 2500 ml of Steady Total Lather Volume, and even more preferably at least 3000 ml of Steady Total Lather Volume, and still more preferably at least 3500 ml of Total Steady Lather Volume. In the context of this application, lathering surfactant means a surfactant, that when combined with a fluid and mechanically agitated generates foam or lather sufficient to cause the article that it's associated with to form a lather. Preferably, these lathering surfactants and, or their combination with other surfactants should be mild, which means that these surfactants provide sufficient cleansing or detersive benefits but do not overly dry the skin or hair, and yet meet the lathering criteria described in the Steady Lather Volume Test.

2) Face Cleansing Compositions

The face cleansing compositions create a lather which is used to wash a small portion of the skin generally using lower amounts of fluid. Face cleansing compositions are particularly useful for facial cleansing at a sink. Generally the face cleansing compositions will preferably comprise no more than about 250 weight percent by weight of the web of a lathering surfactant. Preferably, the compositions of the present invention comprises no more than about 100 weight percent, more preferably no more than about 75 weight percent, and still more preferably no more than about 50 weight percent by weight of the web of a lathering surfactant. Generally the face cleansing compositions will preferably comprise at least 0.5 weight percent by weight of the web of a lathering surfactant. Preferably, the compositions of the present invention comprises at least 0.6 weight percent, more preferably at least 0.75 weight percent, and still more preferably at least 1 weight percent by weight of the web of a lathering surfactant.

The face cleansing compositions of the present invention comprise a sufficient amount of one or more lathering surfactants such that the compositions are capable of generating at least 85 ml of Mechanical Lather Volume according to the Mechanical Lather Volume Test described below. Preferably the face cleansing composition generates at least 150 ml of Mechanical Lather Volume, even more preferably at least 220 ml of Mechanical Lather Volume, and still more preferably at least 350 ml of Mechanical Lather Volume. By a lathering surfactant is meant a surfactant, which when combined with a fluid and mechanically agitated generates a foam or lather sufficient to cause the article, as a whole, to lather. Preferably, these surfactants or combinations of surfactants should be mild, which means that these surfactants provide sufficient cleansing or detersive benefits but do not overly dry the skin or hair, and yet meet the lathering criteria described above.

A wide variety of lathering surfactants are useful for both the body cleansing compositions and the face cleansing compositions described herein and include those selected from the group consisting of anionic lathering surfactants, non-ionic lather surfactants, amphoteric lathering surfactants, and mixtures thereof. Non-limiting examples of lathering surfactants useful in the compositions of the present invention are disclosed in U.S. Pat. No. 6,280,757, to McAtee et al., issued Aug. 28, 2001. Generally, the lathering surfactants do not strongly interfere with deposition of any conditioning agents that are present, e.g., are fairly water soluble, and usually have an HLB value of above 10. Cationic surfactants can also be used as optional components, provided they do not negatively impact the overall lathering characteristics of the required lathering surfactants.

3) Shampoo Compositions

The shampoo article comprises shampoo compositions that are applied to the fibrous, non-woven web. Said article may be a dry, moist or wet article as previously disclosed. This article is suitable for shampoo and the body.

Suitable Surfactants for the lathering cleansing compositions described above include the following surfactants:

Anionic Lathering Surfactants

Non-limiting examples of anionic lathering surfactants useful in the compositions of the present invention are disclosed in McCutcheon's, Detergents and Emulsifiers, North American edition (1986), published by allured Publishing Corporation; McCutcheon's, Functional Materials, North American Edition (1992); and U.S. Pat. No. 3,929,678, to Laughlin et al., issued Dec. 30, 1975.

A wide variety of anionic lathering surfactants are useful herein. Non-limiting examples of anionic lathering surfactants include those selected from the group consisting of sarcosinates, sulfates, isethionates, taurates, phosphates, lactylates, glutamates, and mixtures thereof. Amongst the isethionates, the alkoyl isethionates are preferred, and amongst the sulfates, the alkyl and alkyl ether sulfates are preferred.

Other anionic materials useful herein include are fatty acid soaps (i.e., alkali metal salts, e.g., sodium or potassium salts) typically having from a fatty acid having about 8 to about 24 carbon atoms, preferably from about 10 to about 20 carbon atoms. These fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps and their preparation are described in detail in U.S. Pat. No. 4,557,853.

Other anionic materials include phosphates such as monoalkyl, dialkyl, and trialkylphosphate salts. Non-limiting examples of preferred anionic lathering surfactants useful herein include those selected from the group consisting of sodium lauryl sulfate, ammonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl lactylate, triethanolamine lauroyl lactylate, sodium caproyl lactylate, sodium lauroyl sarcosinate, sodium myristoyl sarcosinate, sodium cocoyl sarcosinate, sodium lauroyl methyl taurate, sodium cocoyl methyl taurate, sodium lauroyl glutamate, sodium myristoyl glutamate, and sodium cocoyl glutamate and mixtures thereof.

Especially preferred for use herein is ammonium lauryl sulfate, ammonium laureth sulfate, sodium lauroyl sarcosinate, sodium cocoyl sarcosinate, sodium myristoyl sarcosinate, sodium lauroyl lactylate, and triethanolamine lauroyl lactylate.

Non-Ionic Lathering Surfactants

Non-limiting examples of nonionic lathering surfactants for use in the compositions of the present invention are disclosed in McCutcheon's, Detergents and Emulsifiers, North American edition (1986), published by allured Publishing Corporation; and McCutcheon's, Functional Materials, North American Edition (1992);

Nonionic lathering surfactants useful herein include those selected from the group consisting of alkyl glucosides, alkyl polyglucosides, polyhydroxy fatty acid amides, alkoxylated fatty acid esters, lathering sucrose esters, amine oxides, and mixtures thereof.

Non-limiting examples of preferred nonionic surfactants for use herein are those selected form the group consisting of $C_8$-$C_{14}$ glucose amides, $C_8$-$C_{14}$ alkyl polyglucosides, sucrose cocoate, sucrose laurate, lauramine oxide, cocoamine oxide and mixtures thereof.

Amphoteric Lathering Surfactants

The term "amphoteric lathering surfactant," as used herein, is also intended to encompass zwitterionic surfactants, which are well known to formulators skilled in the art as a subset of amphoteric surfactants.

A wide variety of amphoteric lathering surfactants can be used in the compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Non-limiting examples of amphoteric surfactants useful in the compositions of the present invention are disclosed in McCutcheon's, Detergents and Emulsifiers, North American edition (1986), published by allured Publishing Corporation; and McCutcheon's, Functional Materials, Noith American Edition (1992).

Non-limiting examples zwitterionic surfactants are those selected from the group consisting of betaines, sultaines, hydroxysultaines, alkyliminoacetates, iminodialkanoates, aminoalkanoates, and mixtures thereof.

Preferred lathering surfactants for use herein are the following, wherein the anionic lathering surfactant is selected from the group consisting of ammonium lauroyl sarcosinate, sodium trideceth sulfate, sodium lauroyl sarcosinate, ammonium laureth sulfate, sodium laureth sulfate, ammonium lauryl sulfate, sodium lauryl sulfate, ammonium cocoyl isethionate, sodium cocoyl isethionate, sodium lauroyl isethionate, sodium cetyl sulfate, sodium lauroyl lactylate, triethanolamine lauroyl lactylate, and mixtures thereof, wherein the non-ionic lathering surfactant is selected from the group consisting of lauramine oxide, cocoamine oxide, decyl polyglucose, lauryl polyglucose, sucrose cocoate, $C_{12-14}$ glucosamides, sucrose laurate, and mixtures thereof; and wherein the amphoteric lathering surfactant is selected from the group consisting of disodium lauroamphodiacetate, sodium lauroamphoacetate, cetyl dimethyl betaine, cocoamidopropyl betaine, cocoamidopropyl hydroxy sultaine, and mixtures thereof.

B. Non-Lathering Cleansing Compositions

Besides the fibrous, non-woven web, the compositions of the present invention also comprise one or more non-lathering surfactants that are associated with the fibrous, non-woven web. Preferred articles of the present invention are either wet or moist and the compositions comprise a sufficient amount of one or more non-lathering surfactants such that the compositions do not generate a lather as disclosed in the Steady Lather Volume Test. The non-lathering cleansing compositions of the present invention comprise a sufficient amount of one or more non-lathering surfactants such that the compositions are capable of generating from at the most 700 ml of Steady Flash Lather Volume according to the Steady Lather Volume Test described below. Preferably the non-lathering cleansing composition generates less than 400 ml of Steady Flash Lather Volume, even more preferably less than 300 ml of Steady Flash Lather Volume, and still even more preferably less than 250 ml of Steady Flash Lather Volume.

Generally the non-lathering cleansing composition will preferably comprise no more than about 1600 weight percent by weight of the web of the non-lathering surfactant, preferably comprise no more than about 1000 weight percent, more preferably no more than about 800 weight percent, and still more preferably no more than about 600 weight percent by weight of the web of a non-lathering surfactant. Generally the non-lathering cleansing composition will preferably comprise at least 15 weight percent by weight of the web of the non-lathering surfactant, preferably at least 25 weight percent, more preferably at least 50 weight percent, and still more preferably at least 60 weight percent by weight of the web of a non-lathering surfactant.

Non-lathering articles will be used for exfoliation, wiping clothes (e.g., wet wipes, refreshment wipes) where lather is not desirable and to lie on skin. Nonlimiting examples of these are skin wiping compositions and refreshing compositions.

Nonlimiting examples of these non-lathering surfactants are: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, PPG-2 methyl glucose ether distearate, ceteth-10, diethanolamine cetyl phosphate, glyceryl stearate, PEG-100 stearate, and mixtures thereof.

1) Skin Wiping Compositions

The skin, nail or hair wipe consists of an article that includes face make-up removal, baby wipes, skin refreshing wipes, incontinent patient bathing wipes, masks and hand cleaning wipes.

2) Refreshing Compositions

Other articles that are useful for non-lathering cleaning include pet shampoo wipes, and cow udder cleaning wipes.

II. Treatment Compositions

Besides the fibrous, non-woven web, the articles of the present invention also comprise one or more treatment compositions that are associated with the fibrous, non-woven web. As being used for treatment, these articles are generally considered non-lathering and such articles can be wet, moist or dry as previously defined. Among the treatment compositions associated with the fibrous, non-woven web of the present invention are skin conditioning agents and skin treatment agents for skin, hair and similar keratinous regions. The treatment compositions of the present invention comprise a sufficient amount of one or more non-lathering surfactants such that the compositions are capable of generating from at the most 700 ml of Steady Flash Lather Volume according to the Steady Lather Volume Test described below. Preferably the treatment composition generates less than 400 ml of Steady Flash Lather Volume, even more preferably less than 300 ml of Steady Flash Lather Volume, and still even more preferably less than 250 ml of Steady Flash Lather Volume.

A. Skin Conditioning Agents

The articles of the present invention can comprise a skin conditioning agent that is useful for providing a conditioning benefit to the skin, hair and other parts of the body with keratin-containing tissue. The skin conditioning agent can comprise no more than about 1600 weight percent, preferably no more than about 1000 weight percent, more preferably no more than about 800 weight percent, and most preferably no more than about 600 weight percent by weight of the web of a skin conditioning agent. The skin conditioning agent can comprise at least 0.05 weight percent, preferably at least 15 weight percent, more preferably at least 15 weight percent, and most preferably no more than about 60 weight percent by weight of the web of a skin conditioning agent.

The skin conditioning agent useful in the present invention can comprise: a water soluble conditioning agent; an oil soluble conditioning agent; a conditioning emulsion; or any combination or permutation of the three. The oil soluble conditioning agent is selected from one or more oil soluble conditioning agents such that the weighted arithmetic mean solubility parameter of the oil soluble conditioning agent is less than or equal to 10.5. The water soluble conditioning agent is selected from one or more water soluble conditioning agents such that the weighted arithmetic mean solubility parameter of the water soluble conditioning agent is greater than 10.5. It is recognized, based on this mathematical definition of solubility parameters, that it is possible, for example, to achieve the required weighted arithmetic mean solubility parameter, i.e. less than or equal to 10.5, for an oil soluble conditioning agent comprising two or more compounds if one of the compounds has an individual solubility parameter greater than 10.5. Conversely, it is possible to achieve the appropriate weighted arithmetic mean solubility parameter, i.e. greater than 10.5, for a water soluble conditioning agent comprising two or more compounds if one of the compounds has an individual solubility parameter less than or equal to 10.5.

Solubility parameters are well known to the formulation chemist of ordinary skill in the art and are routinely used as a guide for determining compatibilities and solubilities of materials in the formulation process. See "Solubility Effects in Product, Package, Penetration, and Preservation", Cosmetics and Toiletries vol. 103, p 47-69, (October 1988).

Non-limiting examples of useful conditioning agents include those selected from the group consisting of petrolatum, fatty acids, esters of fatty acids, fatty alcohols, ethoxylated alcohols, polyol polyesters, glycerine, glycerin monoesters, glycerin polyesters, epidermal and sebaceous hydrocarbons, lanolin, straight and branched hydrocarbons, silicone oil, silicone gum, vegetable oil, vegetable oil adduct, hydrogenated vegetable oils, nonionic polymers, natural waxes, synthetic waxes, polyolefinic glycols, polyolefinic monoester, polyolefinic polyesters, cholesterols, cholesterol esters, triglycerides and mixtures thereof.

More particularly, the conditioning agent may be selected from the group consisting of paraffin, mineral oil, petrolatum, stearyl alcohol, cetyl alchohol, cetearyl alcohol, behenyl alcohol, C10-30 polyesters of sucrose, stearic acid, palmitic acid, behenic acid, oleic acid, linoleic acid, myristic acid, lauric acid, ricinoleic acid, steareth-1-100, cetereath 1-100, cholesterols, cholesterol esters, glyceryl tribehenate, glyceryl dipalmitate, glyceryl monostearate, trihydroxystearin, ozokerite wax, jojoba wax, lanolin wax, ethylene glycol distearate, candelilla wax, carnauba wax, beeswax, and silicone waxes.

Mineral oil, which is also known as petrolatum liquid, is a mixture of liquid hydrocarbons obtained from petroleum. See The Merck Index, Tenth Edition, Entry 7048, p. 1033 (1983) and International Cosmetic Ingredient Dictionary, Fifth Edition, vol. 1, p.415-417 (1993).

Petrolatum, which is also known as petroleum jelly, is a colloidal system comprising nonstraight-chain solid hydrocarbons and high-boiling liquid hydrocarbons. See The Merck Index, Tenth Edition, Entry 7047, p. 1033 (1983); Schindler, Drug. Cosmet. Ind., p. 89, 36-37, 76, 78-80, 82 (1961); and International Cosmetic Ingredient Dictionary, Fifth Edition, Vol. 1, p. 537 (1993).

Nonvolatile silicones such as polydialkylsiloxanes, polydiarylsiloxanes, and polyalkarylsiloxanes are also useful skin conditioning agents. These silicones are disclosed in U.S. Pat. No. 5,069,897, to Orr, issued Dec. 3, 1991.

The skin conditioning agent preferably used in the present invention may also comprise a conditioning emulsion that is useful for providing a conditioning benefit to the skin, hair and similar keratin-containing surfaces during the use of the article. The term "conditioning emulsion" as used herein can either mean the combination of an internal phase comprising a water soluble conditioning agent that is enveloped by an external phase comprising an oil soluble agent or the term "conditioning emulsion" as used herein means the combination of an internal phase comprising an oil soluble agent that is enveloped by an external phase comprising a water soluble agent. In preferred embodiments, the conditioning emulsion would further comprise an emulsifier. The conditioning emulsion comprises from about 15% to about 1600%, preferably from about 25% to about 1000%, more preferably from about 50% to about 800%, and most preferably from about 60% to about 600% by weight of said water insoluble fibrous, nonwoven web. In a preferred embodiment the conditioning emulsion comprises (i) an internal phase comprising water soluble conditioning agents as described above, and (ii) an external phase comprising oil soluble agents as described hereinbefore in the oil soluble conditioning agent section or hereinafter in the "Materials Used to Increase Lipid Hardness Value" section. In further embodiments, the conditioning emulsion further comprises an emulsifier capable of forming an emulsion of said internal and external phases. Although an emulsifier capable of forming an emulsion of the internal and external phases is preferred in the present invention, it is recognized in the art of skin care formulations that a water soluble conditioning agent can be enveloped by an oil soluble agent without an emulsifier. As long as the water soluble conditioning agent is enveloped by the oil soluble agent, thereby protected from being rinsed away during the cleansing process, the composition would be within the scope of the present invention.

B. Skin Treatment Agents

The articles of the present invention can comprise a skin treatment agent that is useful for providing a therapeutic benefit and/or cosmetic benefit to the skin, hair and similar keratin-containing surfaces during the use of the article. The skin treatment agents are suitable for application to keratin-containing tissue, that is, they are suitable for use in contact with human keratin-containing tissue without undue toxicity, incompatibility, instability, allergic response, and the like within the scope of sound medical judgment.

The *CTFA Cosmetic Ingredient Handbook*, Second Edition (1992) describes a wide variety of nonlimiting cosmetic and pharmaceutical ingredients commonly used in the personal care industry, which are suitable for use in the compositions of the present invention. The skin treatment agent can comprise no more than about 1600 weight percent, preferably no more than about 1000 weight percent, more preferably no more than about 800 weight percent, and most preferably no more than about 600 weight percent by weight of the web of a skin treatment agent. The skin treatment agent can comprise at least 0.05 weight percent, preferably at least 15 weight percent, more preferably at least 15 weight percent, and most preferably no more than about 60 weight percent by the weight of the web of a skin treatment agent.

The skin treatment agents useful in the present invention can comprise compositions described herein.

Vitamins

The present articles can comprise vitamin compounds, precursors, and derivatives thereof. These vitamin compounds may be in either natural or synthetic form. Suitable vitamin compounds include, but are not limited to, Vitamin A (e.g., beta carotene, retinoic acid, retinol, retinoids, retinyl palmitate, retinyl proprionate, etc.), Vitamin B (e.g., niacin, niacinamide, riboflavin, pantothenic acid, etc.), Vitamin C (e.g., ascorbic acid, etc.), Vitamin D (e.g., ergosterol, ergocalciferol, cholecalciferol, etc.), Vitamin E (e.g., tocopherol acetate, etc.), and Vitamin K (e.g., phytonadione, menadione, phthiocol, etc.) compounds.

In particular, the articles of the present invention may comprise a safe and effective amount of a vitamin $B_3$ compound. Vitamin $B_3$ compounds are particularly useful for regulating skin condition as described in co-pending U.S. application Ser. No. 08/834,010, filed Apr. 11, 1997 (corresponding to international publication WO 97/39733 A1, published Oct. 30, 1997) which is incorporated by reference herein in its entirety. The therapeutic component of the present invention preferably comprise from about 0.0001% to about 50%, more preferably from about 0.1% to about 10%, even more preferably from about 0.5% to about 10%, and still more preferably from about 1% to about 5%, most preferably from about 2% to about 5%, of the vitamin $B_3$ compound.

As used herein, "vitamin $B_3$ compound" means a compound having the formula:

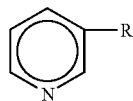

wherein R is —$CONH_2$ (i.e., niacinamide), —COOH (i.e., nicotinic acid) or —$CH_2OH$ (i.e., nicotinyl alcohol); derivatives thereof; and salts of any of the foregoing.

Exemplary derivatives of the foregoing vitamin $B_3$ compounds include nicotinic acid esters, including non-vasodilating esters of nicotinic acid, nicotinyl amino acids, nicotinyl alcohol esters of carboxylic acids, nicotinic acid N-oxide and niacinamide N-oxide.

Examples of suitable vitamin $B_3$ compounds are well known in the art and are commercially available from a number of sources, e.g., the Sigma Chemical Company (St. Louis, Mo.); ICN Biomedicals, Inc. (Irvin, Calif.) and Aldrich Chemical Company (Milwaukee, Wis.).

The vitamin compounds may be included as the substantially pure material, or as an extract obtained by suitable physical and/or chemical isolation from natural (e.g., plant) sources.

Zeolites

Non-limiting examples of zeolites useful herein include natural zeolites such as analcite, chabazite, heulandite, natrolite, stilbite, and thomosonite; and synthetic zeolites such as those made by the gel process (sodium silicate and alumina) or a clay process (kaolin), which forms a matrix to which the zeolite is added.

Peptides

Peptides, including but not limited to, di-, tri-, tetra-, and pentapeptides and derivatives thereof, may be included in the compositions of the present invention in amounts that are safe and effective. Non-limiting examples of peptides and peptide derivatives useful herein include; Carnosine® (beta-ala-his), gly-his-lys, arg-lys-arg, his-gly-gly, palmitoyl-gly-his-lys (which may be purchased as Biopeptide CL®, 100 ppm commercially available from Sederma, France), Peptide CK (arg-lys-arg), PEPTIDE CK+ (ac-arg-lys-arg-$NH_2$), and a copper derivative of his-gly-gly sold commercially as IAMIN, from Sigma (St. Louis, Mo.). Tetrapeptides and pentapeptides (such as palmitoyl-lys-thr-thr-lys-ser commercially available from Sederma France) are also suitable for use herein.

When included in the present compositions, peptides are preferably included in amounts of from about $1\times10^{-6}$% to about 10%, more preferably from about $1\times10^{-6}$% to about 0.1%, by weight of the composition.

Sunscreen Actives

The compositions of the subject invention may contain a sunscreen active. As used herein, "sunscreen active" includes both sunscreen agents and physical sunblocks.

Inorganic sunscreens useful herein include the following metallic oxides; titanium dioxide having an average primary particle size of from about 15 nm to about 100 nm, zinc oxide having an average primary particle size of from about 15 nm to about 150 nm, iron oxide having an average primary particle size of from about 15 nm to about 500 nm, and mixtures thereof. When used herein, the inorganic sunscreens are present in the amount of from about 0.1% to about 20%, preferably from about 0.5% to about 10%, by weight of the composition.

A wide variety of conventional organic sunscreen actives are suitable for use herein. Sagarin, Vol. 102 pages 21 et seq., of *Cosmetics and Toiletries* (1987), discloses numerous suitable actives. Nonlimiting examples of organic sunscreen actives useful herein include octylsalicylate, 2-phenylbenzimidazole-5-sulphonic acid salts, salts of terephthalylidene dicamphor sulfonic acid, octocrylene, octylmethoxycinnamate, avobenzone, and mixtures thereof.

When present in compositions of the present invention, a safe and effective amount of the organic sunscreen active is used, typically from about 1% to about 20%, more typically from about 2% to about 10% by weight of the composition.

Terpene Alcohols

The topical compositions of the present invention may, in some embodiments, contain a safe and effective amount of a terpene alcohol such as farnesol, farnesol derivatives, and mixtures thereof. When included in compositions of the present invention, the terpene alcohol is preferably is included in an amount from about 0.001% to about 50% by weight of the composition, more preferably from about 0.01% to about 20%, by weight of the composition.

Desquamation Actives

A safe and effective amount of a desquamation active may be added to the compositions of the present invention, preferably from about 0.1% to about 10%, more preferably from about 0.2% to about 5%, by weight of the composition. Non-limiting examples of desquamation systems useful herein include; a combination of sulfhydryl compounds and zwitterionic surfactants; and a combination of salicylic acid and zwitterionic surfactants.

Anti-Acne Actives

The compositions of the present invention may contain a safe and effective amount of one or more anti-acne actives. Examples of useful anti-acne actives include resorcinol, sulfur, salicylic acid, benzoyl peroxide, erythromycin, zinc, etc.

Anti-Wrinkle Actives/Anti-Atrophy Actives

The compositions of the present invention may further contain a safe and effective amount of one or more anti-wrinkle actives or anti-atrophy actives. Non-limiting examples of anti-wrinkle/anti-atrophy actives suitable for use in the compositions of the present invention include hydroxy acids (e.g., alpha-hydroxy acids such as lactic acid and glycolic acid or beta-hydroxy acids such as salicylic acid and salicylic acid derivatives such as the octanoyl derivative), phytic acid, lipoic acid; lysophosphatidic acid, and skin peel agents.

Anti-Oxidants/Radical Scavengers

A safe and effective amount of an anti-oxidant/radical scavenger may be added to the compositions of the subject invention, preferably from about 0.1% to about 10%, more preferably from about 1% to about 5%, of the composition.

Non-limiting examples of anti-oxidants/radical scavengers useful herein include; ascorbic acid (vitamin C) and derivatives thereof; tocopherol (vitamin E) and derivatives thereof (e.g. tocopherol sorbate, tocopherol acetate); butylated hydroxy benzoic acids and their salts, 6-hydroxy-2,5,7,8-tetramethylchroman-2-carboxylic acid; sorbic acid and its salts; lipoic acid, amines (e.g., N,N-diethylhydroxylamine, amino-guanidine); tea extracts; grape skin/seed extracts; and mixtures thereof.

Flavonoids

The compositions of the present invention may optionally contain a flavonoid compound. Flavonoids are broadly disclosed in U.S. Pat. Nos. 5,686,082 and 5,686,367. Non-limiting examples of flavonoids useful herein include unsubstituted flavone, 7,2'-dihydroxy flavone, 3',4'-dihydroxy naphthoflavone, 4'-hydroxy flavone, 5,6-benzoflavone, and 7,8-benzoflavone, unsubstituted isoflavone, daidzein (7,4'-dihydroxy isoflavone), 5,7-dihydroxy-4'-methoxy isoflavone, soy isoflavones (a mixture extracted from soy), and mixtures thereof.

When present, the flavonoid compounds are preferably present in concentrations of from about 0.01% to about 20%, more preferably from about 0.1% to about 10%, by weight of the composition.

Anti-Inflammatory Agents

A safe and effective amount of an anti-inflammatory agent may be added to the compositions of the present invention, preferably from about 0.1% to about 10%, more preferably from about 0.5% to about 5%, of the composition.

Nonlimiting examples of "natural" anti-inflammatory agents that are useful herein include candelilla wax, bisabolol (e.g., alpha bisabolol), aloe vera, plant sterols (e.g., phytosterol), and mixtures thereof.

Additional anti-inflammatory agents useful herein include glycyrrhizinate compounds such as dipotassium glycyrrhizinate.

Anti-Cellulite Agents

The compositions of the present invention may also contain a safe and effective amount of an anti-cellulite agent. Non-limiting examples of anti-cellulite agents useful herein include xanthine compounds (e.g., caffeine, theophylline, theobromine, and aminophylline).

Topical Anesthetics

The compositions of the present invention may also contain a safe and effective amount of a topical anesthetic. Examples of topical anesthetic drugs include benzocaine, lidocaine, pharmaceutically acceptable salts thereof, and mixtures thereof.

Tanning Actives

The compositions of the present invention may contain a tanning active. When present, it is preferable that the compositions contain from about 0.1% to about 20%, more preferably from about 2% to about 7%, by weight of the composition, of the artificial tanning active.

A non-limiting example of a tanning active useful herein is dihydroxyacetone.

Chelators

As used herein, "chelator" or "chelating agent" means an active agent capable of removing a metal ion from a system by forming a complex so that the metal ion cannot readily participate in or catalyze chemical reactions. The inclusion of a chelating agent is especially useful for providing protection against Lw radiation which can contribute to excessive scaling or skin texture changes and against other environmental agents which can cause skin damage.

Exemplary oil-soluble chelators that are useful herein are disclosed in U.S. Pat. No. 5,487,884, issued Jan. 30, 1996 to Bissett et al.; International Publication No. 91/16035, Bush et al., published Oct. 31, 1995; and International Publication No. 91/16034, Bush et al., published Oct. 31, 1995. Preferred oil-soluble chelators useful in compositions of the subject invention are furildioxime, furilmonoxime, and derivatives thereof.

Skin Lightening Agents

The compositions of the present invention may contain a skin lightening agent. When used, the compositions preferably contain from about 0.1% to about 10%, more preferably from about 0.2% to about 5%, by weight of the composition, of a skin lightening agent. Non-limiting examples of skin lightening agents useful herein include those known in the art, including niacinamide, kojic acid, arbutin, glucosamine and derivatives, phytosterol derivatives (e.g. sitosterol, campesterol, brassicasterol, lupenol, α-spinasterol, stigmasterol, their derivatives, and combinations thereof), ascorbic acid and derivatives thereof (e.g sodium ascorbyl phosphate), and extracts (e.g., mulberry extract, placental extract).

Antimicrobial and Antifungal Actives

The compositions of the present invention may contain an antimicrobial or antifungal active. A safe and effective amount of an antimicrobial or antifungal active may be added to the present compositions, preferably, from about 0.001% to about 10%, more preferably from about 0.01% to about 5%, and still more preferably from about 0.05% to about 2%.

Preferred examples of actives useful herein include those selected from glycolic acid, lactic acid, phytic acid, N-acetyl-L-cysteine, phenoxyethanol, phenoxypropanol, phenoxyisopropanol, and mixtures thereof.

Skin Soothing and Skin Healing Actives

The compositions of the present invention may include a skin soothing or skin healing active. Skin soothing or skin healing actives suitable for use herein includes panthenoic acid derivatives (including panthenol, dexpanthenol, ethyl panthenol), aloe vera, allantoin, bisabolol, and dipotassium glycyrrhizinate. A safe and effective amount of a skin soothing or skin healing active may be added to the present composition, preferably, from about 0.1% to about 30%, more preferably from about 0.5% to about 20%, by weight of the composition.

Preferred embodiments include: therapeutic treatment (e.g., acne articles), sunscreen application articles, anti-cellulite articles, anti-wrinkle articles, masks, self tanner articles, foot scrubbing articles, cosmetic application articles and perfume/fragrance articles.

III. Combination Cleansing and Treatment Compositions

These articles exemplify treatments together with cleansing compositions on a single cloth. The compositions can be added separately or the compositions can be mixed together prior to being associated with the fibrous, non-woven web.

Additional Ingredients

The articles of the present invention can comprise a wide range of other optional components. These additional components should be pharmaceutically acceptable. The CTFA Cosmetic Ingredient Handbook, Second Edition, 1992, which is incorporated by reference herein in its entirety, describes a wide variety of nonlimiting cosmetic and pharmaceutical ingredients commonly used in the skin care industry, which are suitable for use in the compositions of the present invention. Nonlimiting examples of functional classes of ingredients are described at page 537 of this reference. Examples of these and other functional classes include: abrasives, absorbents, anticaking agents, antioxidants, vitamins, binders, biological additives, buffering agents, bulking agents, chelating agents, chemical additives, colorants, cosmetic astringents, cosmetic biocides, denaturants, drug astringents, external analgesics, film formers, fragrance components, humectants, opacifying agents, pH adjusters, preservatives, propellants, reducing agents, skin bleaching agents, and sunscreening agents.

Also useful herein are aesthetic components such as fragrances, pigments, colorings, essential oils, skin sensates, astringents, skin soothing agents, and skin healing agents.

The compositions used in the present invention may also contain a "fluid" such as water, mono- and polyhydric alcohols (glycerin, propylene glycol, ethanol, isopropanol, etc.), hydrocarbon oils such as mineral oil, silicone oils having a viscosity, and can contain other components dissolved or dispersed within them, or in addition to them.

Cationic Polymers

The compositions used in the present invention may also contain an organic cationic deposition polymer. Concentrations of the cationic deposition polymer preferably range from about 0.025% to about 3%, more preferably from about 0.05% to about 2%, even more preferably from about 0.1% to about 1%, by weight of the personal care composition.

Suitable cationic deposition polymers for use in the present invention contain cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the personal cleansing composition. The average molecular weight of the cationic deposition polymer is between about 5,000 to about 10 million, preferably at least about 100,000, more preferably at least about 200,000, but preferably not more than about 2 million, more preferably not more than about 1.5 million. The polymers also have a cationic charge density ranging from about 0.2 meq/gm to about 5 meq/gm, preferably at least about 0.4 meq/gm, more preferably at least about 0.6 meq/gm., at the pH of intended use of the personal cleansing composition, which pH will generally range from about pH 4 to about pH 9, preferably between about pH 5 and about pH 8.

Nonlimiting examples of cationic deposition polymers for use in the personal care composition include polysaccharide polymers, such as cationic cellulose derivatives. Preferred cationic cellulose polymers are the salts of hydroxyethyl cellulose reacted with trimethyl ammonium substituted epoxide, referred to in the industry (CTFA) as Polyquatemium 10 which are available from Amerchol Corp. (Edison, N.J., USA) in their Polymer KG, JR and LR series of polymers with the most preferred being KG-30M.

Other suitable cationic deposition polymers include cationic guar gum derivatives, such as guar hydroxypropyltrimonium chloride, specific examples of which include the Jaguar series (preferably Jaguar C-17) commercially available from Rhodia Inc., and N-Hance polymer series commercially available from Aqualon.

Other suitable cationic deposition polymers include synthetic cationic polymers. The cationic polymers suitable for use in the cleansing composition herein are water soluble or dispersible, non crosslinked, cationic polymers having a cationic charge density of from about 4 meq/gm to about 7 meq/gm, preferably from about 4 meq/gm to about 6 meq/gm, more preferably from about 4.2 meq/gm to about 5.5 meq/gm. The select polymers also must have an average molecular weight of from about 1,000 to about 1 million, preferably from about 10,000 to about 500,000, more preferably from about 75,000 to about 250,000.

The concentration of the cationic polymer in the personal care composition ranges from about 0.025% to about 5%, preferably from about 0.1% to about 3%, more preferably from about 0.2% to about 1%, by weight of the composition.

A non limiting example of a commercially available synthetic cationic polymer for use in the cleansing compositions is polymethyacrylamidopropyl trimonium chloride, available under the trade name POLYCARE™ 133, from Rhodia, Cranberry, N.J., U.S.A.

Steady Lather Volume Test

Articles of the present invention can provide a steady lather profile as described hereafter. The body cleansing compositions have high Total Steady Lather Volumes, whereas the non-lathering articles have low Steady Flash Lather Volumes. The personal care article can be cleansing or non-cleansing, and can be lathering or non-lathering with different lather profiles as described below. The Steady Lather Volume Test provides a measure of the lather profile of an article in the presence of a renewed water supply, a condition such as naturally exists during bathing or showering.

The lather profile described herein is a combination of the Steady Flash Lather Volume and the Steady Total Lather Volume, both of which are determined in accordance with the following Steady Lather Volume Test. Eight 1,000 ml graduated cylinders are chosen which are marked in 10 ml increments and have a height of 14.5 inches at the 1,000 ml mark from the inside of the base (for example, Pyrex No. 2982). 100 grams of distilled water (+/−0.3 grams, at 23° C.) is added to each graduated cylinder. The cylinders, numbered sequentially from the first cylinder (Cylinder 1) to the last cylinder (Cylinder 8) are clamped in a rotating apparatus which clamps the cylinders with an axis of rotation which transects the center of the graduated cylinder in an axis parallel to the ground with the cylinder standing upright. Stopcocks are added to Cylinder 2 through Cylinder 8.

The article is prepared by cutting it into four equal width strips in the longest dimension. If the article contains entrapped contents that spill if the article is cut into strips, the article is instead folded into four equal strips. If folding and inserting into the graduated cylinders is not possible due to size of the article, the article is cut into strips that can be inserted, and any contents which may spill out during this procedure are caught and added separately into the first graduated cylinder described hereinafter. These strips are stacked and clipped at one end with a simple binder clip, which is selected to be narrow enough to fit inside the neck of the graduated cylinders. A thin polymer thread such as a thin fishing line is tied to the clip so that when the thread is held aloft, the strips hang vertically from the clip and thread. The strips are inserted into the first graduated cylinder (Cylinder 1) so that they hang vertically inside the graduated cylinder with the top ends of the stack of strips hanging evenly with the 1,000 ml mark on the side of Cylinder 1.

The stopcock is then inserted into the neck of Cylinder 1, fixing the strips of the article relative to the graduated cylinder. If necessary, the overhanging thread can be taped to the outside of Cylinder 1 before inserting the stopcock. Also, to prevent leaking, Teflon® tape can be used to effect a waterproof seal. The cylinders are automatically rotated by the rotating apparatus 50 rotations at a steady rate of 50 rotations in 88 seconds in order to generate a lather, which is comprised of foam cells, and stopped in a vertical position to complete a first rotation sequence.

A timer is set to allow 30 seconds for the lather thus generated to drain. After 30 seconds of such drainage, the first lather volume, designated Lather in Cylinder 1, is measured to the nearest 10 ml mark by recording the lather height in ml up from the base in Cylinder 1 (said height includes water that has drained to the bottom, on top of which the lather is floating). If the top surface of the lather is uneven, the lowest height at which it is possible to see halfway across the first graduated cylinder is the Lather in Cylinder 1 (ml). If the lather is so coarse that a single or only a few foam cells reach across the entire cylinder, the height at which at least 5 foam cells are required to fill the diameter is the Lather in Cylinder 1, also in ml up from the base. Foam cells larger than one inch in diameter are designated as unfilled air instead of lather when they occur at the top surface of the lather. Lather that collects on the top of the graduated cylinder but does not move to the bottom of the graduated cylinder is also incorporated in the measurement of the lather on the top is in its own continuous layer, by adding the ml of foam collected there using a ruler to measure thickness of the layer and translating it to ml of volume, to the ml of lather measured up from the base. If a significant amount of lather (e.g., about 60 ml of volume or more) hangs on the side of the graduated cylinder making measurement of the total lather inaccurate or difficult, the lather on the top and sides is urged to the bottom part of the graduated cylinder to meet the other lather prior to measuring volume (during the 30 second drainage period) using a semicircular shaped flexible plow attached to a rod, for example a 2 inch diameter plug cut from a sponge, cut again in half, and secured to a long threaded rod. The maximum lather volume possible is 1,000 ml (even if the total foam height exceeds the 1,000 ml mark on the graduated cylinder). The minimum lather volume possible is 100 ml (even if there is no foam, the height of the water in the graduated cylinder is designated the top of the lather and is measured as the Lather in Cylinder 1).

After the Lather in Cylinder 1 is recorded, the thread is held and stopcock removed, and the strips are removed from the first graduated cylinder, which is then re-cocked. Holding the strips of article only by the thread, the strips are lightly touched for a few seconds to a stack of absorbent paper towels to remove water drops from the bottom of the strips. Then, in the same manner as previously described, the strips of the article are fixed inside the second graduated cylinder, which is numbered as previously described as Cylinder 2, its stopcock is added, and a second rotation sequence is completed, the lather volume being measured in the second cylinder in the same manner as described for the first graduated cylinder, and is recorded as the Lather in Cylinder 2. This sequence is continued a total of eight times, the lather volume in each graduated cylinder being recorded as the lather volume in that cylinder. That is, the lather volume in Cylinder 1, Cylinder 2, Cylinder 3, Cylinder 4, Cylinder 5, Cylinder 6, Cylinder 7 and Cylinder 8 is designated, respectively, as the Lather in Cylinder 1, Lather in Cylinder 2, Lather in Cylinder 3, Lather in Cylinder 4, Lather in Cylinder 5, Lather in Cylinder 6, Lather in Cylinder 7, and Lather in Cylinder 8. The Steady Flash Lather Volume is obtained by adding together the Lather in Cylinder 1 and the Lather in Cylinder 2. The Steady Total Lather Volume is obtained by adding together the lather obtained in all eight graduated cylinders.

Mechanical Lather Volume Test

Personal care articles of the present invention provide a Mechanical Lather Volume as described hereafter. The personal care articles can be cleansing or non-cleansing, and can be lathering or non-lathering with different Mechanical Lather Volumes as described below. The Mechanical Lather Volume Test provides a measure of the mechanical lather of an of an article in the presence of a restricted water supply, a condition such as naturally exists during washing at a sink, for example washing the face at a sink, especially removing makeup at a sink using a lathering cloth, cloth-like article, or fibrous, non-woven web.

A 1,000 ml graduated cylinder is chosen which is marked in 10 ml increments and has a height of 14.5 inches at the 1,000 ml mark from the inside of the base (for example, Pyrex No. 2982). 25 grams of distilled water (+/−0.1 grams, at 23° C.) is added to the graduated cylinder.

The article is prepared by cutting it into four equal width strips, by cutting lengthwise in the longest dimension. The strips are stacked and clipped at one end with a binder clip, designated the top clip, which is selected to be narrow enough to fit inside the neck of the graduated cylinders. If the article contains entrapped contents that spill if the article is cut into strips, the article is instead folded into four equal strips. If folding and inserting into the graduated cylinders is not possible due to size of the article, the article is cut into strips that can be inserted, and any contents which may spill out during this procedure are caught and added separately into the first graduated cylinder described hereinafter.

A binder clip is attached to the bottom of each strip, each facing the opposite direction of the top clip. A binder clip is attached to the center of each strip, facing a 90 degree angle from the direction of the top and each bottom clip. The clips weigh an average of 2.7 grams each. The clips are to provide a weight so that during rotation of the cylinder, the strips may alternately contract to a shorter length and expand to their full length, causing mechanical action which can generate lather in the presence of a lathering surfactant component. A thin polymer thread such as a thin fishing line is tied to the top clip so that when the thread is held aloft, the strips hang vertically from the top clip and thread.

The strips are inserted into the graduated cylinder so that they hang vertically inside the graduated cylinder with the top end of the stack of strips hanging evenly with the 1,000 ml mark on the side of the cylinder. A stopcock is inserted into the neck, fixing the strips of the article relative to the graduated cylinder. The cylinder is rotated for 25 rotations at a steady rate of 25 rotations in 44 seconds in order to generate a mechanical lather, which is comprised of foam cells, and is stopped in a vertical position. The strips are observed during the rotations, each rotation causing the strips to cycle through a maximum compression as they are inverted to a maximum extension in the original vertical position. The extent of compression is based on the wet compliance of the strips, and thus varies. If strips which are compliant (i.e., relatively easy to compress in the length direction) are observed not to compress during the inverted phase of the rotations due to interfering factors such as (1) too rapid rate of rotation of the cylinders, (2) interference by lather produced, (3) sticking of strips to the walls of the cylinder, or (4) a combination of factors, then the rotation speed of the apparatus is slowed down until the strips are observed to compress with each inversion and extend in the vertical position. It is important to complete a full 25 compression-extension cycles of the strips, to the extent that they compress and extend, based on their compliance. If the strips do not compress and extend, the rate of rotation is slowed to as low as 15 rotations per minute (rpm) to accomplish the intended compression-extension of the strips. If the strips still do not compress and/or extend because of interfering factors listed above, the cylinders are shaken by hand at each vertical position, being held there momentarily during each rotation, to allow the strips to compress and extend.

The measurement is then continued for a second 25 rotations by restarting the rotating apparatus. The rotating apparatus should be restarted within 5 seconds of stopping. The rotating apparatus is again restarted within 5 seconds of stopping, and a third 25 rotations is completed. The stopcock is removed and the article is lowered using the attached thread to the bottom with any lather gathered there. Remaining lather on the sides and top of the graduated cylinder is urged to the bottom of the graduated cylinder using the same plow described in the Steady Lather Volume Test. The plow is used to ensure the top lather surface is even. If the top of the lather surface extends beyond the collapsed article, the plow is also used to ensure large (>1 inch) air voids within the collapsed fibrous, non-woven web are filled with lather as it is lowered, before reading the lather volume. If the top of the lather surface does not extend beyond the article, the lather is urged with the plow to the lowest level possible in the cylinder without destroying it or compressing it.

The Mechanical Lather Volume is the height of the lather, inclusive of the underlying fibrous, non-woven web if the height is above the top level of the fibrous, non-woven web. The lather height is measured within 15 seconds of stopping. If the height is lower than the top level of the fibrous, non-woven web, the Mechanical Lather Volume is the height of the topmost portion of the lather surface that extends across the graduated cylinder. If the article expands during the test, such as a sponge might expand when first wetted, the plow is used to urge lather off the surface of the expanded fibrous, non-woven web, which is not lowered to the cylinder bottom and not included in the lather height. If the article fills during the test, such as a balloon fills with air, then a new article of the same type is prepared by scoring and/or puncturing the article and repeated the test, so that filling does not occur, and the Mechanical Lather Volume is the lather height with the scored or punctured article. The maximum lather volume possible is 1,000 ml (even if the total foam height exceeds the 1,000 ml mark on the graduated cylinder). The minimum lather volume possible is 0 ml (the height of the water, which may be absorbed into the article). If no lather is visible inside the graduated cylinder, it is not necessary to lower the article and measure a height: the Mechanical Lather Volume is designated as the height of the water in the bottom of the graduated cylinder.

Moisture Retention Methodology

As described above, the articles of the present invention can be "substantially dry". As used herein, "substantially dry" means that the articles of the present invention exhibit a Moisture Retention of less than about 0.95 gms, preferably less than about 0.75 gms, even more preferably, less than about 0.5 gms, even more preferably less than about 0.25 gms, even still more preferably less than about 0.15 gms, and most preferably, less than about 0.1 gms. The Moisture Retention is indicative of the dry feel that users perceive upon touching the articles of the present invention as opposed to the feel of "wet" wipes.

In order to determine the Moisture Retention of the present articles and other disposable fibrous, non-woven web-based products, the following equipment and materials are needed.

| Bounty White Paper Towel | Procter & Gamble SKU 37000 63037 Basis Weight = 42.14 gsm |
|---|---|
| Balance | Accurate to 0.0 g |
| Lexan | 0.5" thickness large enough to cover samples completely and weighs 1000 g |
| Weight | A 2000 g weight or combination to equal 2000 g |

Next, weigh two paper towels separately and record each weight. Place one paper towel on flat surface (e.g., lab bench). Place the sample article on top of that towel. Place the other paper towel on top of sample article. Next, place the Lexan and then the 2000 g weight(s) on top of the sandwiched sample article. Wait 1 minute. After the minute, remove weight(s) and Lexan. Weigh the top and bottom paper towel and record the weight.

Calculate the Moisture Retention by subtracting the initial paper towel weight from the final weight (after 1 minute) for both the top and bottom paper towels. Add the weight differences obtained for the top and bottom paper towels. Assuming multiple articles are tested, average the total weight differences to obtain the Moisture Retention.

As described above, the articles of the present invention can be "substantially dry", "moist", or "wet" prior to use. The article can feel dry to the touch and still contain high water content. The Moisture Retention is indicative of the dry feel that users perceive upon touching the articles of the present invention as opposed to the feel of "wet" articles. Thus, articles of the present invention that feel dry to the touch can have a dry feel relatively independent of the amount of fluid they contain. Articles of the present invention which have a dry feel will exhibit a Moisture Retention of less than about 0.95 gms, preferably less than about 0.75 gms, even more preferably, less than about 0.5 gms, even more preferably less than about 0.25 gms, even still more preferably less than about 0.15 gms, and most preferably, less than about 0.1 gms.

As described above, the articles of the present invention can be "wet" prior to use. The article can feel wet to the touch and contain high water content. The weight percent of fluid in the "wet" article is based on the dry weight of the web. The weight is expressed as a weight of the total composition. Thus, the "wet" articles of the present invention will generally comprise from about greater than 40% by weight of fluid, preferably from 40% to about 95% by weight of fluid, and more preferably from about 50% to about 80% by weight of fluid.

Methods of Manufacture

The articles of the present invention can be manufactured by separately or simultaneously adding onto the surface of said web and, onto or impregnating into said web, before or after it has undergone selective mechanical deformation, a cleansing and, or a treatment composition. By "separately" is meant that the cleansing and treatment compositions can be added sequentially, in any order without first being combined together. By "simultaneously" is meant that the cleansing and treatment compositions can be added with or without first being combined together.

The cleansing and/or the treatment composition can be embedded onto or impregnated into the fibrous, non-woven web using any means known to those skilled in the art. These components can be applied using various spraying, soaking, coating or dipping techniques. Excess surfactant and/or conditioning component can be removed (e.g., by a nipping process). The resulting article can remain as wet or can be further processed to be moist or dry using conventional methods known in the art.

Methods of Using Articles

The present invention also relates to a method of cleansing and, or treating the skin, hair or other keratin-containing tissues of the body with a personal care article of the present invention that is soft due to the structure of the fibrous, fibrous, non-woven web. These methods comprise the steps of wetting with fluid a disposable, personal care article comprising a fibrous, non-woven web, wiping the article across the area to be cleansed and, or treated with the cleansing and, or a treatment composition. The articles of the present invention can be wetted with fluid prior to use, already contain fluid prior to use, or not require any fluid in order to use the article. The substantially dry article is wetted by immersion in fluid or by placing it under a stream of fluid. Lather is generated from the article by mechanically agitating and/or deforming the article either prior to or during contact of the article with the skin, hair or other keratin-containing surfaces.

The resulting lather is useful for cleansing and treating the skin, hair or other keratin-containing surfaces. During the cleansing/treatment process and subsequent rinsing with water, the treatment agents and active ingredients are contacted with the skin, hair or other keratin-containing surfaces. Deposition of treatment compositions and active ingredients are enhanced by the physical contact of the fibrous, non-woven web with the skin, hair or other keratin-containing tissues of the body.

Without being limited by theory it is believed that the fibrous, non-woven web significantly contributes to generation of lather and deposition of treatment compositions and any other active ingredients. It is believed that this lathering and deposition is the result of the surface action of the fibrous, non-woven web. As a result, milder and significantly lower amounts of surfactants may be employed. The decreased amount of required surfactant is believed to relate to a decrease in the drying effect of the skin or hair by the surfactants. Furthermore, the diminished amount of surfactant lowers any inhibitory action (e.g., via emulsification or direct removal by the surfactants) which surfactants exhibit regarding deposition of treatment compositions. Further without being limited by theory, it is believed that the fibrous, non-woven web also enhances deposition of treatment compositions and active ingredients. Furthermore, because the treatment compositions and active ingredients are embedded onto or impregnated into the fibrous, non-woven web, they are transferred directly to the skin, hair or other keratin-containing surfaces by surface contact of the wet, moist or wetted article to the skin.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified amounts are concentrations by weight of the total cleansing, treatment compositions, unless otherwise specified.

Example 1

A tufted non-woven web is prepared, which is also looped. The nonwoven precursor non-woven web is comprised of 100% polypropylene spunbond fibers and has a basis weight about 17 grams per square meter (gsm) and is sold by First Quality Fibrous Nonwovens, Hazleton, Pa. (USA), specified as Hydrophilic PHOB+C 1,2,3, containing a softness additive. The precursor non-woven web is tufted using a toothed roll that has a 0.060 in. pitch (P), a tooth height (TH) of 0.145 in., a spacing between teeth (TD) of 0.0625 in., and a tooth length (TL) of 0.050 in. The toothed roll and grooved roll were set at an engagement (E) of 0.135 in. The diameter of the toothed and grooved rolls is each about 6 inches. The precursor non-woven web is fed through the nip at a line speed of 25 feet per minute (fpm). The tufted web is examined by preparing scanning electron microscope (SEM) images of the deformations of the first side (i.e., the tufted side) of the web and evaluated by the procedures described herein. Representative deformations comprised an average of 23 fibers of which about 83% were unbroken, tufted fibers that are looped. The diameter of individual looped fibers is about 12 microns midway between the proximal and distal portion, and about 15 microns in the bulk (0.80 diameter ratio). The height× maximum width of the loop is about 0.80 mm×1.1 mm, and the loops have a minimum width proximal to the surface of the web of about 0.60 mm. Assuming elliptical dimensions, a planar projection of the loops is represented by an ellipse with one axis equal to the loop height and a second axis equal to the maximum width for the loop, the loop area is calculated as 0.69 mm$^2$ according to the standard equation for area of an ellipse (=$\pi ab/4$, where a and b are the axes of the ellipse).

Example 2

A tufted fibrous, non-woven web is prepared. The same polypropylene fibrous, non-woven web of Example 1 is used, and the same toothed roll and setup, excepting the line speed is increased to 500 feet per minute. Deformations are observed to be less loop-like.

Example 3

A tufted fibrous, non-woven web is prepared which is dual zoned (i.e., one area of the web defines a zone having tufts; and a second area of the same web defines a second zone, having no tufts), having both tufted and untufted portions. The tufted portions appear mostly looped. The same polypropylene fibrous, non-woven web of Example 1 is used. A toothed roll is used which has the same pattern as the previous example, but is hand cranked (line speed only a few feet per minute, using an arm attached to the toothed roll, the toothed roll being geared to the grooved roll, so that when the arm is rotated using force applied by hand, the rolls rotate, drawing the web through the nip between the rolls, where tufting occurs). The toothed roll has portions of the rolls which do not have teeth, but instead have voids, the voids being in rows oriented in both the machine direction and cross machine direction, the rows having a width of about 0.85 cm. and spaced at 7.5 cm between rows (center to center distance) in both directions. Portions of the tufted web, in first regions, are tufted. Other portions of the web, in second regions, which is in rows and corresponding to the portions of the toothed roll which contains no teeth, are unmodified. Thickness of the web is measured using a Mitutoyo model ID-C112CEB micrometer. The thickness of the tufted portions in the first region is about 0.39 mm. The thickness of the tufted web in the second, untufted region is about 0.14 mm.

Example 4

A tufted fibrous, non-woven web is prepared. The fibrous, non-woven web is comprised of fibers which are DAPP fibers (Deeply Activated Polypropylene), which are multiconstituent fibers comprising polypropylene, polyethylene, and at least another copolymer. The basis weight of the fibrous, non-woven web is about 30 gsm+/5 gsm. The fibrous, nonwoven web is obtained from BBA Fibrous Nonwovens, Simpsonville, N.C., and produced by Fiberweb, Inc, of France and marketed as Sofstpan 200). The web is tufted using the toothed roll and setup in Example 1, at a line speed of 50 fpm, and the tufted web is examined in the same manner. Representative tufts comprise an average of 20 fibers of which about 90% are unbroken, looped fibers. The diameter of individual looped fibers is about 22 microns in the loops, and about 24 microns in the bulk (0.92 diameter ratio). The height×maximum width of the loop is about 1.30 mm×0.90 mm, and the loops have a minimum width of about 0.55 mm. Assuming elliptical dimensions as previously discussed in Example 1, the loop area is calculated as 0.92 mm².

Example 5

A tufted fibrous, non-woven web is prepared using the same materials, process and conditions as Example 4 except the line speed is increased to 500 fpm. Representative tufts comprised an average of 20 fibers of which about 70% were unbroken, looped fibers., The diameter of individual looped fibers is about 16.5 microns in the loops, and about 20 microns in the bulk (0.83 diameter ratio). The height×maximum width of the loop is about 0.95 mm×0.85 mm, and the loops have a minimum width of about 0.55 mm. Assuming elliptical dimensions as previously discussed in Example 1, the loop area is calculated as 0.63 mm².

Example 6

The same polypropylene fibrous, non-woven web of Example 4 is used to prepare a tufted fibrous, non-woven web. A toothed roll is used which has the same pattern as the previous example, but is hand cranked, as described in Example 3, (line speed only a few feet per minute). The toothed roll has portions of the rolls which do not have teeth, but instead have voids, voids being defined by the absence of teeth, in rows extending in the MD and in the CD. Portions of the tufted web, in first region, are tufted. Other portions of the web, in second regions, which is in rows and around the edges, as defined in Example 3, are unmodified. Thickness of the web is measured using a Mitutoyo model ID-C 112CEB micrometer. The thickness of the tufted web in the first region is about 0.92 mm. The thickness of the tufted web in the second, untufted region is about 0.21 mm.

Example 7

A fibrous, non-woven web is tufted utilizing the same toothed roll and equipment settings and line speed as Example 4, and using the same material from the same supplier as Example 4 but at a higher basis weight, 60 gsm. The web is evaluated microscopically. Representative tufts comprise an average of 32 fibers of which about 75% are unbroken, looped fibers. The diameter of individual looped fibers is about 13 microns in the loops, and about 18 microns in the bulk (0.72 diameter ratio). The height×maximum width of the loop is about 1.35 mm×1.03 mm, and the loops have a minimum width of about 0.45 mm. Assuming elliptical dimensions, as described in Example 1, the loop area is calculated as 1.09 mm².

Example 8

Utilizing the same material and toothed roll as the previous example, the line speed is increased to 500 fpm with no other changes. The web is evaluated microscopically. The diameter of individual looped fibers is about 17.5 microns in the loops that are formed, and about 21 microns in the bulk (0.83 diameter ratio). The height×maximum width of the loop is about 1.20 mm×1.20 mm, and the loops have a minimum width of about 0.60 mm. Assuming elliptical dimensions, as described in Example 1, the loop area is calculated as 1.13 mm². Representative tufts comprise an average of about 25 fibers of which about 68% are unbroken, looped fibers.

Example 9

A fibrous, non-woven web is tufted. The web is T260 HEC (High Elongation Carded), which is a lightly bonded, high elongation carded fiber web comprised of 100% polypropylene carded fibers, manuctured by BBA Fibrous, non-woven webs, Simpsonville, S.C., and has a basis weight of 40 gsm. The web is processed in the same manner as Example 4. The web is evaluated microscopically. Representative tufts comprise an average of 18 fibers of which about 44% are unbroken, looped fibers. The diameter of individual looped fibers is about 18.5 microns in the loops, and about 20 microns in the bulk (0.93 diameter ratio). The height×maximum width of the loop is about 1.30 mm×1.15 mm, and the loops have a minimum width of about 0.55 mm. Assuming elliptical dimensions, as described in Example 1, the loop area is calculated as 1.17 mm².

Example 10

Utilizing the same material and toothed roll as the previous example, the line speed is increased to 500 fpm with no other changes. The web is evaluated microscopically. Representative tufts comprise an average of 22 fibers of which about 36% are unbroken, looped fibers. The diameter of individual looped fibers is about 15 microns in the loops, and about 15 microns in the bulk. The height×maximum width of the loop is about 1.20 mm×0.85 mm, and the loops have a minimum width of about 0.60 mm. Assuming elliptical dimensions, as described in Example 1, the loop area is calculated as 0.80 mm².

Example 11

A fibrous, non-woven web is tufted. The web is 100% polypropylene prepared by a spunbond/spunlace process, has a basis weight of 50 gsm, and is manufactured by Avgol Nonwovens, Greensboro, N.C. The same toothed roll as the previous example was used, with a line speed of 10 fpm. The depth of engagement of the toothed and grooved rolls is set at an engagement (E) of 0.100 in. The web is evaluated microscopically. Representative tufts comprise an average of about 29 fibers of which about 50% are unbroken, looped fibers.

The diameter of individual looped fibers is about 16 microns in the loops, and about 16 microns in the bulk. The height×maximum width of the loop is about 0.90 mm×0.70 mm, and the loops have a minimum width of about 0.60 mm. Assuming elliptical dimensions, as described in Example 1, the loop area is calculated as 0.49 mm².

Example 12

A fibrous, non-woven web is tufted using a heated press. The web is the same as Example 11. A pneumatic toothed roll is used with top and bottom metal plates having the same tooth and groove measurements as the rolls of Example 1. The plates are 1.5 cm thick and 30 cm square in the x and y dimensions, the toothed top plate and grooved bottom plate being milled to the aforementioned tooth and groove dimension specifications. Two pins on the top plate align with two holes on the bottom plate, allowing the plates to be mounted on the pneumatic tufting roll precisely so that teeth align with depressions between grooves, engaging in the same manner as the rolls of Example 1. Shims, which are metal spacers having a precise thickness, are used to effect a depth of engagement (E) of 0.050 in. between the toothed and grooved plates. The pneumatic toothed roll is an AIRAM ATP-1585 pneumatic press made by Airam, Inc, Aiken, S.C., USA. The web is tufted using a 1 second dwell time (contact time). The web is evaluated microscopically. Representative tufts comprise an average of about 50 fibers of which about 100% are unbroken, looped fibers. The diameter of individual looped fibers is about 7 microns in the loops, and about 15 microns in the bulk. The height×maximum width of the loop is about 0.55 mm×0.50 mm, and the loops have a minimum width of about 0.50 mm. Assuming elliptical dimensions, as described in Example 1, the loop area is calculated as 0.22 mm².

Example 13

A fibrous, non-woven web is tufted at a line speed of 10 fpm using the toothed roll described in Example 1, with the same 0.135 in. engagement (E). The web is comprised of 5 denier spunbond Polyethylene (PE)/Polypropylene (PP) bicomponent fibers in a core-sheath configuration and has a basis weight of 70 gsm, and is manufactured and sold by BBA Nonwovens, Simpsonville, S.C., USA under the trade name Softex®. The tufted, looped web has a thickness of 1.09 mm measured by the Mitutoyo micrometer. The web is evaluated microscopically. Representative tufts comprise an average of about 44 fibers of which about 100% are unbroken, looped fibers. The diameter of individual looped fibers is about 17 microns in the loops, and about 27 microns in the bulk. The height×maximum width of the loop is about 1.55 mm×1.20 mm, and the loops have a minimum width of about 0.65 mm. Assuming elliptical dimensions, as described in Example 1, the loop area is calculated as 1.46 mm².

Example 14

The same material as Example 13 at a higher basis weight, 80 gsm, is tufted in the same manner as described in Example 13. The web is evaluated microscopically. Representative tufts comprise an average of about 61 fibers of which about 100% are unbroken, looped fibers. The diameter of individual looped fibers is about 19 microns in the loops, and about 32 microns in the bulk. The height×maximum width of the loop is about 1.05 mm×1.25 mm, and the loops have a minimum width of about 0.625 mm. Assuming elliptical dimensions, as described in Example 1, the loop area is calculated as 1.03 mm².

Example 15

Using the same process and material as Example 13, the line speed is increased to 300 fpm. The web is evaluated microscopically. Representative tufts comprise an average of about 67 fibers of which about 100% are unbroken, looped fibers. The diameter of individual looped fibers is about 16 microns in the loops, and about 26 microns in the bulk. The height×maximum width of the loop is about 1.00 mm×1.10 mm, and the loops have a minimum width of about 0.60 mm. Assuming elliptical dimensions, as described in Example 1, the loop area is calculated as 0.86 mm².

Example 16

A baby wipe is prepared. A chemical component is prepared from the following ingredients by mixing until homogeneous and buffering the pH to 5.5.

| Ingredient | CTFA or common name (supplier) | % of ingredient (100% solids basis) |
|---|---|---|
| Water | water | qs |
| Benzyl alcohol | Benzyl alcohol (CAS No. 100-51-6) | 0.50 |
| IPBC | Iodopropynyl butylcarbamate (CAS No. 55406-53-6) | 0.09 |
| Disodium EDTA | Disodium EDTA | 0.10 |
| Aloe vera ritaloe | *Aloe Barbadensis* Juice (Rita Corp) | 0.0025 |
| 50 cSt dimethicone | Dimethicone (GE Silicones) | 2.0 |
| Polysorbate 20NF | Polysorbate 20 (Croda) | 0.08 |
| Suttocidea | sodium hydroxymethylglycinate 50% solution (Sutton Laboratories, Chatham, NJ, USA) | 0.15 |
| Preservative | | 0.15 |

The looped web of Example 7 is cut into individual wipes having dimensions 18 cm by 20 cm, and Z-folded in an interleaving configuration with an overlapping portion and stacked in groups of 40 wipes with the tufted side facing out. The chemical component is added to the stacks at an add-on rate of 350% based on the cloth weight, and cloths are packaged in a "pop-up" wipes dispenser, in which upon pulling a wipe out of the tub, an edge of the next wipe is presented for easy dispensing.

Example 17

A tufted fibrous, non-woven web is prepared from a spunbond web having a basis weight of about 18 gsm. The web is comprised of fibers which are 100% white polyester (PET), and is manufactured by Freudenberg Fibrous Nonwovens, 3440 Industrial Dr., Durham, N.C. 27704. The web is tufted using the equipment and setup and hand cranking procedure as Example 6. The web produced is tufted with a low proportion of looped fibers. The web has a thickness of 0.36 mm in the tufted zone, and a thickness of 0.13 mm in the untufted zone.

Example 18

A fibrous, non-woven web is prepared which is tufted and has a high proportion of looped fibers. The web is a core-sheath bicomponent fiber (PE/PP) spunbond web having a basis weight of 46 gsm, manufactured by BBA Fibrous Nonwovens. The tufts are prepared using a toothed roll having teeth with TL of 0.25 in. and pitch (P) of 0.25 in. The teeth are arranged in rows, every other row offset by ½ pitch to create a staggered pattern. The depth of engagement (E) is 0.135 in. The apparatus is cranked by hand as described previously. The web has tufts which appear as tunnel-like loops, seen to be open at two ends by careful examination, which measure about 6 mm length×1.25 mm width. The web has a thickness of 0.91 mm in tufted regions and 0.37 mm in untufted regions.

The webs are each tufted to prepare a tufted web using the process and conditions of Example 4. The webs are prepared according to the following compositions:

|  | Example 22 | Example 23 | Example 24 | Example 25 | Example 26 | Example 27 | Example 28 |
|---|---|---|---|---|---|---|---|
| Fiber | Core-sheath Bico 50/50 PE/PP | 100% PP | 100% PP | Layered 50/50 bico 20 gsm; PP 40 gsm | Core-sheath Bico 70/30 PE/PP | Core-sheath Bico 50/50 PE/PP | Core-sheath Bico 50/50 PE/PP |
| Denier | 5 | "high" 5 | "low" 2.5 | 5 | 5 | 5 | 5 |
| Basis wt. | 60 gsm | 60 gsm | 60 gsm | 60 gsm | 60 gsm | 80 gsm | 50 gsm |

Example 19

A fibrous, non-woven web is prepared utilizing the apparatus and procedure of Example 18. The web is the same as Example 11. Tunnel-like tufts are evident, which have looped fibers.

Example 20

A fibrous, non-woven web is prepared utilizing the apparatus and procedure of Example 18. The web is the same as Example 1. Tunnel-like tufts are evident, which have looped fibers.

Example 21

A tufted fibrous, non-woven web having looped fibers is prepared from two precursor webs. Two identical webs are mated physically, which are 34 gsm webs comprising core-sheath bicomponent fibers which are dark blue in color. The mated webs are fed into the toothed roll, using conditions of Example 3 to create tufts, which have fibers originating and ending in both precursor webs. The tufting procedure with the two webs creates what is essentially a single web by interlocking the webs at the tufts. The tufted web has a thickness of 1.18 mm in the tufted regions, and 0.42 mm in the untufted regions. In a cloth measuring 8.375 in. long×6.75 in. wide there are three tufted regions, four untufted rows extending across the width of the cloth (including the untufted rows at the edge), and two untufted rows extending the length of the cloth, at the edges. The untufted rows are connected. The cloth has the appearance and feel of a high quality, terry cloth washcloth or small towel with a hemmed edge.

Examples 22-28

Spunbond webs are prepared using a process with multiple (sequential) spinnerets, producing webs which have mixtures of PP and PE/PP bicomponent fibers. Some of the webs are prepared with mixtures of fibers that are not organized. Other webs are prepared with sequential spinnerets using different fibers to layer the fibers from the top to the bottom of the web.

The following fibrous, non-woven webs or formed films are prepared which are not tufted, but are used as components of subsequent examples by combining with the webs of the previous examples.

Example 29

A web is obtained from Tredegar Corp., Terre Haute, Ind., USA which is a large hex pattern (8.75 hex) formed film comprising a polyethylene blend (HDPE/LDPE). The web has a basis weight of about 36 gsm and a thickness of 0.04 in. The formed film is a film containing hexagonally shaped pores formed from a precursor film by drawing the film across the surface of a forming screen, the forming screen being a drum shaped, hollow frame with a screen on the surface of the drum, the screen having a hexagonal pattern corresponding to the resulting land area of the film and open area corresponding to the pores. The formed film is formed from the precursor film by rotating the drum with the film in contact with the drum and applying water jets which impinge upon the film at a pressure of about 3,000 psi, said jets rupturing the film in the open area of the screen, creating pores in the film.

Example 30

A web is obtained from the Tredegar Corp., Terre Haute, Ind., USA which is a formed film having a basis weight of 25 gsm and a thickness of about 0.017 in., comprising low density polyethylene polymer.

Example 31

A web is obtained commercially which is 100% polyester, adhesive bonded using a latex adhesive and a dip & nip process, which dips the unbonded web through a trough filled with adhesive and uses two rubber rolls with a nip to squeeze excess adhesive, the web having a basis weight of 2 oz/yd$^2$ (68 gsm), as is available commercially by many manufacturers, such as Steams Textiles, Cincinnati, Ohio, USA. The web is a batting and has a thickness of about 5.8 mm.

Example 32

A web is obtained which is a closed cell polyethylene foam. The web has a thickness of about ⅛ in., a basis weight of 93 gsm, and a density of about 30 kg/m$^3$. The web is slit in the machine direction in rows, the slits ¾ in. long with ¼ in. between slits within a row, and ⅛ in. between rows of slits. Slits in alternating rows are offset in the MD by ½ the length of a slit, so that when the slitted web is pulled apart in the CD, the web opens to a lattice pattern. Such a web is supplied by Kevron LLC, Portland, Oreg., U.S.A.

Example 33

A batting is obtained which is an airlaid blend of carded fibers (50% PET, 50% PE/PP core-sheath bicomponent) having a basis weight of 65 gsm and a thickness of 2.7 mm, from Libeltex NV, Belgium.

Example 34

A composite web is prepared, which is a web formed from two precursor webs. A single ply sheet of a cellulose absorbent paper towel (Bounty towel, marketed by Procter & Gamble Co., Cincinnati, Ohio, USA) is attached to a sheet of 0.25 oz/yd$^2$ spunbond polypropylene using point bonds which are ultrasonic welds spaced at about 5 mm between points in offset rows. A polypropylene web is available from BBA Fibrous Nonwovens is marketed as Celestra®.

Example 35

A dual textured lathering cloth or article (terms used interchangeably to mean the same thing in these Examples) for cleansing the body in a shower is prepared. A lathering surfactant component is prepared from the following ingredients:

| Ingredient | Supplier or common CTFA name | Amount added |
|---|---|---|
| Alkyl Glyceryl Sulfonate (AGS) 47.5% solids paste | (Procter & Gamble Co., Iowa City, Iowa, USA) | 62.8% |
| Lauramidopropyl Betaine, 30-35% active | Colonial Chemical Inc., USA | 19.7% |
| Citric Acid Anhydrous | Citric acid | 0.2% |
| Propylene Glycol | Propylene glycol | 15.2% |
| Polyox WSR-301 | (Amerchol) PEG 90M | 0.20% |
| JR30M | (Amerchol) Polyquaternium-10 | 0.50% |
| Perfume | | 1.0% |
| Preservative & misc. | | 0.4% |

The ingredients are prepared by mixing the cationic polymer with the glycol and surfactants under heat with continuous stirring to avoid lumps. The perfume is added during cooling. The lathering surfactant component melts upon heating to about 60 degrees C. or more, and solidifies upon cooling to a hard solid. The percentages added in this and subsequent examples are of the ingredient including water it may contain.

A layered, laminated article is prepared using two layers of the tufted web of Example 20 with the deformations facing away from the cloth interior (same direction for all following examples also), and two layers of the batting of Example 33. The lathering surfactant component is heated until liquid, and slot coated in 3 rows between the batting layers at a rate of 4 grams per finished article. The layers are sealed using an ultrasonic sealer such as a Branson Model 9000 Ultrasonic Sealer, which seals a dot pattern comprising a grid of 4 mm diameter sealing points spaced evenly across the article at 3 cm intervals. The sealed web is cut into 11.9 cm×9.0 cm rectangles to create the finished article.

Example 36

A dual textured lathering cloth for cleansing the body in a shower is prepared. A lathering surfactant component is prepared from the following ingredients:

| Ingredient | Supplier or common CTFA name | Amount added |
|---|---|---|
| Alkyl Glyceryl Sulfonate (AGS) 47.5% solids paste | (Procter & Gamble Co., Iowa City, Iowa, USA) | 61.7% |
| Empigen Total Active LC/U, 35% active | Lauramidopropyl betaine (Huntsman Surface Sciences, London, England, U.K.) | 19.2% |
| Citric Acid Anhydrous | Citric acid | 0.2% |
| Propylene Glycol | Propylene glycol | 11.8% |
| Polyox WSR-301 | (Amerchol) PEG 90M | 0.2% |
| JR30M | (Amerchol) Polyquaternium-10 | 0.5% |
| Perfume | | 1.0% |
| Preservative, colorants & misc. | | 0.4% |
| Petrolatum[1] | | 5.0% |

[1](Crompton Witco Refined Products, Middlebury, CT, USA) petrolatum.

The ingredients are processed in the same manner as Example 35. A layered, laminated article is prepared using a first layer of the tufted web of Example 19, an interior layer which is the formed film of Example 30 with the male side facing toward the batting layer, and a layer of the batting of Example 33. The lathering surfactant component is slot coated in a thin layer between the first layer and the interior batting layer at a rate of 5.0 grams per finished article and is finished in the same manner as Example 35.

Example 37

A dual textured lathering cloth for cleansing the body in the bath is prepared. A lathering surfactant component is prepared from the following ingredients:

| Ingredient | Supplier, chemical or common CTFA name | Amount added |
|---|---|---|
| Triethanolamine | Aldrich Chemical Co, USA | 16.9% |
| TEA-Stearate (TEA soap of Stearic acid) | From Emery 410 Stearic acid (Emery Division of Henkel, Cincinnati, OH, USA) and Triethanolamine (Aldrich) | 32.3% |
| Sodium tallowate | From Emery 401 (Emery/Henkel) and Sodium hydroxide (Aldrich) | 16.1% |
| Water | Dist. water | 6.9% |
| Glycerin | Aldrich Chemical Co, USA | 10.7% |
| Sodium cocoate | From coconut fatty acids (Emery/Henkel) and Sodium hydroxide (Aldrich) | 6.6% |
| Sodium ricinoleate | From ricinoleic acid, (Acme-Hardesty, Blue Bell, PA, USA) and Sodium hydroxide (Aldrich) | 4.3% |
| TEA-Oleate | From Emery 233 oleic acid (Emery/Henkel) and Triethanolamine (Aldrich) | 3.9% |
| Cocoamide DEA | CAS # [68603-42-9] (USA Chemicals, Inc, West Memphis, Arkansas, USA) | 1.3% |
| Fragrance and preservative | | 1.0% |

Separately, a sodium soap is prepared from an excess amount of the tallow fatty acid, coconut fatty acids, ricinoleic acid in the relative proportions indicated by the component amounts, and half the amount of glycerin and water necessary in the final component batch. Sodium hydroxide is added in the stoichiometric amount necessary to neutralize the fatty acids with no excess to make the soap. Also separately, a triethanolamine (TEA) soap is prepared in the same manner with the stearic acid and oleic acid, neutralizing with a 10% excess of TEA. The sodium and TEA soaps are blended with the other ingredients except fragrance and heated to 85 degrees C. When homogeneous, the mixture is cooled, fragrance is added during cooling. The mixture is a hard soap at room temperature, and is a liquid above 80° C. with a viscosity of only about 19 cP at 85 degrees C. and 2.5 l/seconds shear rate on a cone & plate viscometer.

A layered, laminated article is prepared using a first layer of the tufted web of Example 18, an interior layer which is the web of Example 33, and two layers of the creped web of Example 30. The lathering surfactant component is heated to 80° C. and sprayed onto the center layer at a rate of 3 grams per finished article on the side facing the batting, prior to sealing the layers together. The layers are then sealed through the surfactant component, and cut into a square about 150 cm$^2$ to finish the article.

Example 38

A dual textured lathering cloth for cleansing the body in a shower is prepared. A lathering surfactant component is prepared from the following ingredients:

| Ingredient | Supplier or common CTFA name | Amount added |
|---|---|---|
| Alkyl Glyceryl Sulfonate (AGS) 47.5% solids paste | (Procter & Gamble Co., Iowa City, Iowa, USA) | 77.7% |
| Petrolatum | (Crompton Witco Refined Products, Middlebury, CT, USA) petrolatum | 5.0% |
| Citric Acid Anhydrous | Citric acid | 0.2% |
| Propylene Glycol | Propylene glycol | 15.0% |
| Polyox WSR-301 | (Amerchol) PEG 90M | 0.2% |
| N-Hance 3196 | (Aqualon-Hercules, Irvine, CA, USA) cationic guar or guar hydroxypropyltrimonium chloride | 0.50% |
| Perfume | | 1.0% |
| Preservative & misc. | | 0.4% |

The ingredients are processed in the same manner as Example 35. A layered, laminated-article is prepared using a first layer of the tufted web of Example 19, an interior layer which is the batting of Example 37, and an exterior layer of the same batting. The lathering surfactant component is slot coated in stripes between the batting layers at a rate of 4.0 grams per finished article and is finished in the same manner as Example 35.

Example 39

A dual textured lathering cloth for cleansing the body in a shower is prepared. A lathering surfactant component comprising 33.1% active surfactants is prepared from the following ingredients.

| Ingredient | Supplier or common CTFA name | Amount added |
|---|---|---|
| Sodium lauryl sulfate (SLS) 29% active solution | (Stepan Chemical, Northfield, IL, USA) Stepanol WA-EXTRA | 21.9% |
| Sodium Laureth Sulfate 70% active | (Stepan Chemical) STEOL CS-270 | 29.1% |
| Citric Acid Anhydrous | Citric acid | 0.2% |
| Cocamidopropyl betaine 30% active | (Stepan Chemical) AMPHOSOL CG | 21.4% |
| Water | | 25.3% |
| JR30M | (Amerchol) Polyquaternium-10 | 0.5% |
| Perfume | | 1.2% |
| Preservative, colorants & misc. | | 0.4% |

A web is prepared by sealing together two layers of the tufted web of Example 20, and a layer of the web of Example 33, with the side formed at the highest temperature facing away from the cloth interior. The lathering surfactant component, which has a low viscosity, is sprayed onto the web at a rate of 12 grams per finished article and the web is dried using forced hot air to a water content of about 5%. The web is cut into rectangular shapes having an area of about 270 cm to create finished articles.

Examples 40-43

Lathering surfactant components are prepared for Examples 40-43 having the following percentages.

| | Example 40 component | Example 41 component | Example 42 component | Example 43 component |
|---|---|---|---|---|
| Example 39 surfactant component | | 50.8% | 59.8% | 34.1% |
| AGS 47.5% solids paste | 74.2% | 49.2% | | |
| Sodium Laureth Sulfate 70% active | 25.8% | | 40.2% | 60.9% |
| Cocamidopropyl betaine 30% active | | | | 5.0% |

Next, webs are laminated according to the following table, without the surfactant component. The layers are sealed together using point bonds in a grid pattern with a heat sealing die utilizing a pressure-platen heat sealing device such as a Sentinel Model 808 heat sealer available from Sencorp, Hyannis, Mass. The point bonds measure about 4 mm diameter each and are spaced at 2 cm intervals in a hexagonal array. The laminates are cut into rectangles having an area of about 270 cm$^2$.

|  | Example 40 | Example 41 | Example 42 | Example 43 |
|---|---|---|---|---|
| Soft side web | Example 1 | Example 2 | Example 3 | Example 34 |
| Rougher side web | Example 31 | Example 31 | Example 31 | Example 31 |

The examples are finished by coating the surfactant components onto the laminated webs. The surfactant components are heated to reduce viscosity and, drawn into a syringe, and coated through the rougher side of the web (Examples 40-42) or onto the surface of the rougher side (Example 43) at a rate of 3.8 grams per finished article.

Examples 44-47

The following chemical components are prepared and used for Examples 44-47 articles, which are useful for cleaning the face, especially removing makeup, at the sink. The component phase B is prepared in water and the petrolatum emulsified into the component phase B at 75° C. to make a 25% solids aqueous mixture of phase A+B, which is the surfactant component for these examples. The formula shown does not include the added water. Component phase C is prepared by mixing the ingredients separately.

| Ingredient common name or trade name | Ingredient CTFA name | CAS # | % active chemical added | Phase |
|---|---|---|---|---|
| Petrolatum (Witco) | Petrolatum | 8009-03-8 | 32.3 | A |
| Carbowax PEG 4600 flake (Dow Chemicals, USA) | Polyethylene Glycol 4600 | 25322-68-3 | 17.5 | C |
| Cocamidopropyl Hydroxysultaine | Cocamidopropyl Hydroxysultaine | 68139-30-0 | 11.7 | B |
| Hamposyl L-30 (Hampshire Chem) | Sodium Lauroyl Sarcosinate | 137-16-6 | 11.7 | B |
| Plantaren 2000 N UP (Cognis Care Chemicals, NJ, USA) | Decyl Glucoside | mixture | 11.7 | B |
| Beta CycloDextrin | Beta CycloDextrin | 7585-39-9 | 5.0 | C |
| Butylene Glycol | Butylene Glycol | 107-88-0 | 3.6 | B |
| Polyox WSR N3000 (Amerchol) | PEG 14M | 25322-68-3 | 1.8 | B |
| Ucare Polymer JR30M (Amerchol) | Polyquaternium-10 | 53568-66-4 | 0.9 | B |
| Perfume | Fragrance |  | 0.8 | C |
| D-Panthenol | Panthenol | 81-13-0 | 0.7 | B |
| Salicylic Acid | Salicylic Acid | 69-72-7 | 0.2 | B |
| Menthol | Menthol | 89-78-1 | 0.1 | C |
| Acusol 460N (Rohm & Haas) | Water & Sodium MA/ Diisobutylene Copolymer |  | 0.06 | C |
| Misc. preservatives, vitamins |  | mixture | 1.99 | B |

Articles are prepared by dipping webs into a trough of the surfactant component, running the webs through a nip roll to meter the surfactant to the appropriate add-on rate, spraying on component phase C, and drying the cloth in a forced air oven to a moisture content of about 11%. The surfactant component is added at a rate of 86 grams per square meter of web (gsm). Component C is added at the rate of 6.6 gsm. The webs used for Examples 44-47 are as follows:

|  | Example 44 | Example 45 | Example 46 | Example 47 |
|---|---|---|---|---|
| The web of example: | Example 22 | Example 7 | Example 23 | Example 24 |

The webs are cut into rectangles having rounded corners and a surface area of about 275 cm$^2$.

Example 48-50

Lathering, face cleansing articles are prepared. The surfactant component of Examples 44-47 is prepared in the same manner except the petrolatum is left out, and the surfactant component is prepared at 25% solids. Articles are prepared by spraying the surfactant component onto the webs at a rate of 39 gsm, drying the web to about 11% moisture content, and spraying petrolatum onto the web at a rate of 4.5 gsm (Example 48), 9.1 gsm (Example 49) and 13.5 gsm (Example 50). Component C is added at the same rate as Examples 46-49. The webs used for Examples 48-50 are as follows.

|  | Example 48 | Example 49 | Example 50 |
|---|---|---|---|
| The web of example: | Example 25 | Example 26 | Example 27 |

The webs are cut into rectangles having rounded corners and a surface area of about 275 cm$^2$.

Example 51

A fragrance free cloth is prepared useful for washing the face and removing makeup. The surfactant component of Examples 48-50 is prepared and sprayed onto a web at the rate of 30 gsm (i.e., about 7.5 gsm chemicals). No petrolatum or fragrance is added to the web. The web used is the web of Example 28. The web is dried and cut in the manner of the previous example.

Example 52

A wet lathering cloth is prepared, useful for washing the face and removing makeup. The cloth of Example 21 is prepared having a surface area of about 365 cm$^2$. The surfactant component (25% solids) of Example 48 is sprayed onto the cloth at the rate of 63 gsm. Thirty cloths are prepared identically, folded in half, stacked, and packaged in a hermetically sealed wrap having good vapor barrier properties. The wrap is placed in a tub with a snap lid. The article can be used as a wipe or activated with additional fluid to produce lather.

Example 53

A dual textured lathering cloth for cleansing the body in a shower is prepared. First, a lathering surfactant component is prepared. Shave 53.0 gm of a bar soap which includes the following components:

| Ingredient | Wt % |
| --- | --- |
| Sodium Cocyl Isethionate | 27.77 |
| Paraffin wax | 16.72 |
| Sodium Alkyl Glycerol Sulfonate (AGS) | 14.90 |
| Sodium tallowate | 11.41 |
| Glycerin | 8.57 |
| Water | 5.50 |
| Stearic Acid | 5.74 |
| Sodium Isethionate | 3.04 |
| NaCl | 1.41 |
| Polyox WSR N3000 | 0.03 |
| Perfume | 0.70 |
| Miscellaneous (including pigments) | 4.21 |

Mix the bar soap shavings with 37.0 gm glycerin (99.7% pure), 9.5 gm water, and 0.5 gm perfume. Heat mixture to 200° F. while stirring continuously. Cold-mill mixture on a standard 3-roll mill to make a homogeneous surfactant paste. An article of the present invention is prepared using the web of Example 15 on one side, two center webs which are the web of Example 30, and the web of Example 11 on the other exterior side. 3.5 grams of the surfactant paste of the current example is extruded in 3 stripes between the webs of Example 30. The article is sealed using the Sentinel Model 808 sealer with point bonds in rows, the rows avoiding the surfactant stripes.

Example 54

A dual textured lathering cloth for cleansing the body in a shower is prepared. First, a dry, powdered lathering surfactant component is prepared by dry blending the following ingredients in a high speed shearing mixer. Perfume is added last, spraying onto the powder once the powder is homogeneous.

| Ingredient | Wt % |
| --- | --- |
| Citric acid, anhydrous (Aldrich Chemical Co) | 24.0 |
| Sodium bicarbonate (Aldrich) | 23.0 |
| Sodium carbonate (Aldrich) | 1.0 |
| Sodium Lauryl Sulfate (Stepanol ME-DRY, Stepan Chemical) | 3.8 |
| Sodium Cocoyl isethionate | 3.8 |
| Guar hydroxypropyltrimonium chloride (N-Hance 3196, Aqualon) | 0.75 |
| Sodium C14-16 Olefin Sulfonate (Bio-TERGE AS90 BEAD, Stepan Chemical) | 3.7 |
| Paraffin wax | 5.0 |
| Sodium Stearoyl Lactylate (Pationic SSL, Rita Corporation, Woodstock, IL, USA) | 3.0 |
| (Mackanate DC-50, McIntyre Group Ltd, University Park, IL, USA) | 1.0 |
| Sodium Behenoyl Lactylate (Pationic SBL, Rita Corp) | 5.0 |
| PEG 9M (Rita PEO-2, Rita Corp) | 5.0 |
| Tocopherol | 0.4 |
| Anticaking agents (mixed silicates) | 9.0 |
| Maltodextrin | 11.1 |
| Perfume | 0.45 |

The tufted webs of Example 14 and Example 12 are cut to matching 150 cm² ovals and bonded at the edges and in the center point using the Sencorp Model 808 heat sealer with 3.0 grams of the surfactant component in the center, and stored in a sealed container.

Example 55

The spunbond, tufted webs of Examples 7 and 13 are bonded in the same manner as the previous example, with 3 grams of the same surfactant component in the center. Petrolatum is sprayed onto one side of the web of Example 7 at the rate of 2 grams per cloth.

Example 56

A cleansing article useful for cleansing the face is prepared. The tufted webs of Examples 8 and 11 are bonded in the same manner as the previous example, with 0.5 grams of the same surfactant component in the center. Lanolin wax (Rita Corp) is sprayed onto one side of the web of Example 11 at the rate of 2 grams per cloth.

Example 57

The surfactant component of Example 54 is prepared. The surfactant component is mixed with a 50/50 mixture of Lanolin wax and Petrolatum in a ratio of 2 parts surfactant component to 1 part lipid mixture by melting the lipid mixture and adding to the surfactant component as it is being agitated in a high shear mixer. A layered article is prepared with the web of Example 4 on one side and the web of Example 17 on the other exterior side, and the webs of Example 5 and 9 layered in the center. 5 grams of the surfactant component is spread between the two center webs, and the webs are bonded at the edges and center using the Sencorp sealer. The lipid ingredients added help the dry ingredients to keep from migrating around the cloth, and also serve to extend the duration of lathering activity of the surfactant component.

Example 58

A commercial body wash is obtained which has about 16% active surfactants. The body wash is distributed by Bath & Body Works and comprises water, sodium laureth sulfate, lauraminde DEA, TEA cocoyl glutamate, cocamidopropyl betaine, fragrance, sodium PCA, aloe leaf juice, carica papaya fruit extract, propylene glycol, polyquaternium-10, preservatives, fragrance, PEG-150 distearate, sodium chloride and colors. A layered article is prepared by bonding with ultrasonic point bonds the web of Example 6 on one side, the foam of Example 32 in the center, and the batting of Example 33 on the bottom. The bonded webs are soaked in the commercial body wash, which is added to the webs at the rate of 1100 gsm. The webs are dried in a forced air oven, turning them over when partially dry and wiping excess body wash back onto the web as it is turned. After drying to about 16% moisture, the web is cut into rectangles measuring 11.9 cm×9.0 cm.

Example 59

A combination shampoo and skin cleansing article is prepared. The following ingredients are blended together, heated to 60° C., the pH is adjusted to 6.5, and the mixture cooled to room temperature.

| Ingredient | Supplier or common CTFA name | Amount of ingredient added |
|---|---|---|
| Additional Water | | 55.18% |
| Stepanol AM | Ammonium lauryl sulfate (Stepan, 28% active) | 4.0% |
| Steol CA-230D | ammonium laureth sulfate Stepan (25% active) | 10.4% |
| Mackam 2C | Disodium Cocoamphodiacetate (McIntyre Group, 50% active) | 15.0% |
| Plantaren 2000 | Decyl polyglucoside (Cognis, 50% active) | 12.0% |
| STEPAN PEG 6000 MS | PEG-150 stearate (Stepan) | 1.5% |
| Citric acid premix | Citric acid (50% aqueous) | 0.4% |
| Jaguar C162 | Hydroxypropyl Guar Hydroxypropyl Trimonium Chloride (Rhodia) | 0.3% |
| Tetrasodium EDTA | Tetrasodium EDTA | 0.1% |
| Preservatives | | 0.05% |
| Colamide HPC | Capramide DEA (Thornley Co., Wilmington, DE, USA) | 1.0% |
| Sodium chloride | | 0.07% |

The web of Example 5 is bonded to the web of Example 33 using point bonds, and is cut into 192 cm² rectangles. Fourteen grams of the ingredient mixture is added to the article and the article is dried to a water content of less than 10%. The article is useful for cleansing the hair and skin and is tear-free composition, not irritating to the eyes and mucosae.

Example 60

A skin conditioning article with sunscreen is prepared comprising the following chemical components.

| Ingredient | Supplier or common CTFA name | Amount of ingredient added |
|---|---|---|
| Sepigel 305 | Polyacrylamide and C13-14 isoparaffin and Laureth-7 (Seppic Inc, Fairfield, NJ, USA) | 3.0% |
| DC 9040 Silicone Elastomer Blend | (Dow Corning) (cyclomethicone (and) dimethicone crosspolymer) | 7.0% |
| Water | | 75.3% |
| Preservatives | | 0.2% |
| Benzophenone-3 | Sunscreen (Shipro Kasei Kaisha, Japan) | 3.0% |
| Octyl methoxycinnamate | Sunscreen (CAS # 5466-77-3) | 7.0% |
| Fragrance | | 1.0% |
| Titanium dioxide | Titanium dioxide (U. S. Cosmetics Corp, Dayville, CT, USA) | 3.5% |

The Sepigel is mixed with the CD 9040 until homogeneous. The titanium dioxide is milled into the water then slowly added to the Sepigel phase with stirring. Separately, the sunscreens are mixed together at 40° C. until homogeneous, and added to the other ingredients with stirring. The fragrance is added and the mixture cooled to ambient.

A cloth is prepared having deformations on both sides of a web. The web is comprised of 5 denier spunbond Polyethylene (PE)/Polypropylene (PP) bicomponent fibers in a core-sheath configuration and has a basis weight of 80 gsm, and is manufactured and sold by BBA Fibrous Nonwovens, Simpsonville, S.C., USA under the trade name Softex®. Deformations are made to both sides of the web simultaneously using a top and a bottom plate having interlocking teeth. A top plate is prepared having rows of teeth with a tooth height (TH) of 0.145 in., a Tooth Length (TL) of 0.050 in., an in-row spacing between teeth (TD) of 0.0625 in., and a pitch (P) of 0.060 in. A bottom plate is prepared having offset rows which interlock with the top plate, the teeth of the bottom row having TL of 0.25 in. The teeth of the bottom row are arranged to form a macroscopic pattern of rectangular arrays, three parallel arrays forming a square, with adjacent squares having alternating, orthogonal direction of the long axis of the array, in order to give the article the appearance of an embroidered cloth. The chemical components are loaded onto the cloth at the rate of 400 gsm. Cloths are stacked and packaged. The article is useful for transferring the sunscreen composition to skin, and gives the skin a soft feel.

Example 61

A conditioning article is prepared for application of emollient material to dry skin. The webs of Example 9 and Example 10 are thermally bonded using point bonds using a Sentinel Model 808 heat sealer from Sencorp. Petrolatum is heated to 90 degrees C. and sprayed onto the side of Example 9 web with a paint sprayer at an add-on rate of 280 gsm. Rectangular articles measuring 124 cm² area are cut. The articles are useful for moisturizing dry skin and can be used in the shower, or on dry skin.

Example 62

A water-free skin wiping article is prepared which comprises a water-free emulsion component useful for moisturizing and cleansing the skin comprising the following ingredients.

| Ingredient | CTFA or common name (supplier) | % of ingredient |
|---|---|---|
| Propylene glycol | Propylene glycol (Aldrich) | q.s. |
| Glycerin | Glycerin (Aldrich) | 6.0% |
| Salicylic acid | Salicylic Acid (Aldrich) | 0.15% |
| PEG-600 ML | PEG-12 Laurate (Stepan) | 13.2% |
| Plurafac D25 | Alcohol alkoxylate (BASF) | 7.6% |
| Plurafac B26 | Alcohol alkoxylate (BASF) | 7.6% |
| Chemonic L-60 | ethoxylated linear alcohol (Chemron, Paso Robles, CA, USA) | 12.5% |
| Mineral oil | Mineral oil (Witco) | 9.2% |
| Benzalkonium chloride, USP | | 10.0% |
| Fragrance | | 0.4% |

The web of Example 14 is prepared, and the emulsion component added to the web at an add-on rate of 240 gsm. The web is cut into rectangular articles 275 cm² in size.

Example 63

A facial treatment mask, that is either wet or dry. For the dry mask, the web is dried. For the wet mask, the web is wet. The facial treatment mask is prepared by mixing Phase A until homogeneous, then combining Phase B and adding the combination to Phase A and, additionally add a preservative. Stir in slowly the Salcare, mixing until uniform.

| Ingredient | CTFA or common name (supplier) | % of ingredient |
|---|---|---|
| Phase A | | |
| Wheat gliadin protein | Wheat gliadin (MGP Ingredients, Atchison, KS, USA) | 5.0 |
| Water, deionized | Water | 90.6 |
| Phase B | | |
| PEG 75 Lanolin | PEG-75 Lanolin (Deutsche Lanolin Gesellschaft, Germany) | 0.5 |
| Perfume | | 0.1 |
| Phase C | | |
| Salcare SC96 | Polyquaternium 37 (and) Propylene Glycol Dicaprate Dicaprylate (and) PPG-1 Trideceth-6 | 3.00 |
| Preservative | | .80 |

The mixture is coated onto a web at the rate of 800 gsm add-on, the web comprised of 5 denier spunbond Polyethylene (PE)/Polypropylene (PP) bicomponent fibers in a core-sheath configuration with a basis weight of 80 gsm, manufactured and sold by BBA Fibrous Nonwovens, Simpsonville, S.C., USA under the trade name Softexg. The web is dried by convection to a water content of 8%. The coated web is tufted at a line speed of 10 fpm using the toothed roll and rolls described in Example 1, with the same 0.135 in. engagement (E). Articles are cut measuring 15 cm square. Articles are used by wetting with warm water and placing them as a mask on the face with the looped side against the skin.

Example 64

A liquid foundation applicator pad is prepared from the following chemical component.

| Ingredient | CTFA or common name (supplier) | % of ingredient |
|---|---|---|
| Water, deionized | | q.s. |
| Potassium hydroxide, 10% aq. | Potassium hydroxide (Aldrich) | 1.0 |
| Niacinamide | Niacinamide | 0.5 |
| Crillet 4 | Polysorbate 80 (Croda, Parsippany, NJ, USA) | 0.1 |
| Titanium dioxide | Titanium dioxide (US Cosmetics) | 0.1 |
| Talc | Pigment | 3.8 |
| Yellow iron oxide | Pigment | 0.8 |
| Red iron oxide | Pigment | 0.4 |
| Black iron oxide | pigment | 0.05 |
| Propylene glycol | Propylene glycol (Aldrich) | 6.0 |
| Veegum | Magnesium aluminum silicate | 1.0 |
| CMC 7H3SF | Cellulose gum (Aqualon) | 0.12 |
| Cromollient DP3-A | di-PPG-3 myristyl ether adipate (Croda) | 12.0 |
| Crodafos CS20 acid | cetearyl alcohol (and) ceteth-20 phosphate (and) dicetyl phosphate (Croda) | 3.0 |
| Volpo S-10 | Steareth-10 (Croda) | 2.0 |
| Vitamin E | Tocopherol | 0.2 |
| Crodacol C-70 | Cetyl alcohol (Croda) | 0.6 |
| Volpo S-2 | Steareth-2 (Croda) | 0.5 |
| Preservative | | 1.0 |

The component is prepared using a standard emulsion procedure and milling the pigments into the water phase with the Polysorbate 80 as the first step, being careful not to aerate the component. The pH is adjusted to 7.5 as a final step. The foundation component is applied to the web of Example 14 at the rate of 400 gsm and cut into 2.5 in. diameter circles and packaged in a hermetically sealed package. The articles are used to apply colored cosmetics to the skin and as an anti-wrinkle treatment.

Example 65

A baby wipe is prepared from the following chemical component. 500 grams of the chemical component is prepared.

| Ingredient | CTFA or common name (supplier) | % of ingredient |
|---|---|---|
| Propylene glycol | (Aldrich) | 7.5 |
| Preservatives | | 1.4 |
| Polysorbate 20 | (Croda) CAS No. 9005-64-5 | 1.0 |
| Fragrance oil | | 0.19 |
| Deionized water | | 484.9 |
| Mackanate ™ DC30 | 30% disodium dimethicone copolyol sulfosuccinate solids (McIntyre Group) | 1.5 |
| Allantoin powder | CAS No. 97-59-6 | 2.5 |

The mixture is sprayed onto the looped web of Example 14 at an add-on rate of 600%. The treated cloths are packaged in a conventional plastic tub with a lid and are useful for wiping the skin, removing soil from baby bottoms effectively while being very soft to the skin during wiping.

Example 66

A wipe is prepared which is useful for removing makeup, which does not require additional water. A chemical component is prepared from the following ingredients:

| Ingredient | CTFA or common name (supplier) | % of ingredient |
|---|---|---|
| Water | | qs |
| Dipropylene glycol | (Aldrich) | 3.0 |
| Glycerin | (Aldrich) | 2.5 |
| Miranol ™ C2M Conc, 50% aq. | Disodium cocoamphodiacetate (Rhodia, Cranbury, NJ, USA) | 0.5 |
| Preservatives | | 0.7 |
| Citric Acid | | 0.4 |
| Sodium Citrate | | 0.2 |
| Polysorbate 20 | CAS No. 9005-64-5 (Croda) | 0.15 |
| Vitamin E | Tocopherol | 0.1 |
| Fragrance | | 0.001 |
| Dimethicone, 50 cSt | Dimethicone (GE) | 0.2 |

The chemical component is sprayed onto the looped web of Example 14 at an add-on rate of 300%. The treated wipes of this example are packaged in a hermetically sealed flexible package with a fitment snap opening closure.

Example 67

A skin sanitizing wiping article is prepared. A chemical component is prepared from the following ingredients by dispersing the Carbopol in water, sequentially adding each ingredient while stirring to maintain a homogeneous mixture. The pH is adjusted to 6.5.

| Ingredient | CTFA or common name (supplier) | % of ingredient |
|---|---|---|
| Water, deionized | | qs |
| Carbopol ™ Ultrez 10 | Carbomer (Noveon, Inc, Cleveland, OH, USA) | 0.35 |
| Angus AMP 95 | Aminomethyl propanol (CAS No. 124-68-5, Angus Chemical Co, Buffalo Grove, IL, USA) | 0.2 |
| SD 40 alcohol | (CAS No. 64-17-5) | 72.0 |
| Crodalan ™ AWS | polysorbate 80 (and) cetyl acetate (and) acetylated lanolin alcohol (Croda) | 2.0 |
| Glycerox HE | PEG-7 glyceryl cocoate (Croda) | 1.0 |
| Osmocide | glycerin (and) water (and) sodium polyacrylate (and) ethoxydiglycol (and) caprylyl glycol (Croda) | 3.0 |

The chemical component is added to the looped web of Example 7 at an add-on rate of 550% and cloths are packaged in a flexible wipes package. The article is useful for cleansing and sanitizing the skin.

Example 68

An applicator wipe which is a self tanning skin care composition is prepared comprising a chemical component prepared from the following ingredients:

| Ingredient - Phase | CTFA or common name (supplier) | % of ingredient |
|---|---|---|
| Water, deionized - A | | Qs |
| Butylene glycol - A | 1,4 butanediol (BASF, Mt. Olive, NJ, USA) | 2.5 |
| Preservatives, aq. - A | | 0.5 |
| Cremaphor ™ A 6 - B | ceteareth-6, stearyl alcohol (BASF) | 3.2 |
| Cremaphor ™ A 25 - B | ceteareth-25 (BASF) | 1.5 |
| Cremaphor ™ GS 11 - B | glyceryl stearate (BASF) | 3.5 |
| Cetyl alcohol - B | | 3.0 |
| Luvitol ™ EHO - B | cetearyl octanoate (BASF) | 5.0 |
| Luvitol ™ BL - B | benzyl laurate (BASF) | 5.0 |
| 50 cSt dimethicone fluid - B | Dimethicone (GE, Waterford, NY, USA) | 0.5 |
| a-Bisabolol - B | Bisabolol | 0.2 |
| Preservatives, non-aq. - B | | 0.1 |
| Fragrance - C | | 0.4 |

Phase A is heated to 75° C., Phase B is heated separately and added to Phase A while mixing until uniform. Fragrance is added during cooling. The chemical component is added to the looped web of Example 7 at an add-on rate of 600% and cloths are packaged in a flexible wipes package.

Example 69

A wet wipe is prepared which is useful for incontinent patient bathing, requiring no rinsing. A chemical component is prepared, comprising the following ingredients:

| Ingredient | CTFA or common name (supplier) | % of ingredient |
|---|---|---|
| Water, deionized | | Qs |
| Propylene glycol | (Aldrich) | 5.5 |
| Glycerin | (Aldrich) | 3.5 |
| Plantaren ™2000, 50% active | Decyl polyglucoside (Cognis, 50% active) | 2.0 |
| Polysorbate20 (Croda) | CAS No. 9005-64-5 (Croda) | 0.2 |
| Citric acid | | 1.2 |
| Preservative | | 0.5 |
| Fragrance | | 0.3 |
| Aloe Vera UP 10:1 concentrate | Aloe Barbadensis gel (Florida Food Products, Eustis, FL, USA) | 0.1 |
| Vitamin E | Tocopheryl acetate | 0.1 |
| Dimethicone, 50 cSt | Dimethicone (GE) | 0.1 |

A two-layered fibrous, non-woven web is prepared having loops of mostly fibers from the first material on the side of the second material. A first layer of 100% rayon web (70 gsm, for example BR070-P15 wipes from Web-pro Corporation, Yunanm Kaohiung, Tawwan) is layered with a second web, an 80 gsm PE/PP bicomponent layer (BBA FibrousNonwovens starting material of Example 14). The material is tufted using the toothed and grooved rolls at the settings of Example 1, with the bicomponent fiber web on the toothed side so that the loops comprising largely bicomponent fibers are created through the rayon web. The chemical component is added to the two-layered, looped web at a rate of 22 ml per 400 $cm^2$ web surface. The web is cut to 400 $cm^2$ size cloths, folded and packaged.

Example 70

A body cleansing kit is prepared. The tufted web of Example 14 is prepared and cut into 300 $cm^2$ square cloths with rounded corners. The cloths are stacked and shrink wrapped in groups of 30 cloths. A commercial body wash is obtained, for example Oil of Olay Moisturizing Body Wash 700 ml size, manufactured and distributed by The Procter & Gamble Co, Cincinnati, Ohio, USA. Three stacks of cloths are shrink wrapped a second time with a single bottle of body wash, constituting a kit comprising about 3 months supply of body wash with disposable washcloths.

Example 71

A face cleansing kit is prepared. The tufted web of Example 7 is prepared and cut into 270 $cm^2$ square cloths. A kit is prepared comprising a 200 ml jar of a cold cream banded to a group of 30 cloths. No water is required when using the kit to cleanse makeup from the face.

Example 72

A body cleansing kit is prepared. The tufted web of Example 7 is prepared and cut into 275 $cm^2$ cloths. A kit is prepared comprising a bar of soap and a group of 30 cloths, which are shrink wrapped together as a unit. The kit constitutes about a 1 month supply of individual, disposable washcloths and soap.

Example 73

A pet care kit is prepared. The tufted web which is disclosed in Example 60 is prepared and cut to 270 $cm^2$ size. Fifteen cloths are banded together and shrink wrapped to a 350 ml bottle of pet shampoo comprising the following ingredients: water, sodium laureth sulfate, cocamidopropyl betaine, decyl glucoside, polyuquaternium-7, fragrance, DMDM hydantoin, tetrasodium EDTA, sodium chloride, citric acid, benzophenone-4, D&C Green No. 5 and FD&C Yellow No. 5. The kit is useful for lathering and cleaning pets, and is used with an external water supply.

Example 74

A face treatment kit is prepared. The tufted web of Example 7 is prepared and cut into 290 cm² cloths. A kit is prepared comprising a 50 ml jar of face cream banded to a group of 30 cloths. No water is required when using the kit to treat the face.

Example 75

A dual textured lathering article is prepared using the webs of Example 39 and the surfactant component of Example 36. Five grams of the surfactant component is melted and applied in 4 stripes to the center of the layers prior to sealing the FQN web layers to the Avgol polypropylene layer. A rectangular article measuring 270 cm² is cut. The article has a Steady Flash Lather Value of about 1,330 ml and a Steady Total Lather Value of about 4,020 ml. The article is useful for producing a steady stream of lather when used in an environment where the supply of water is steady, i.e., a shower.

Example 76

A dual textured lathering article is prepared using the webs of Example 39, which are bonded together in the absence of a chemical component and cut to the same size as the previous example. A chemical component is prepared comprising the following ingredients:

| Ingredient | Supplier or common CTFA name | % of ingredient added |
|---|---|---|
| STEPANOL ™ WA-EXTRA, 30% active | Sodium Lauryl Sulfate (Stepan) | 18.03 |
| STEOL ™ CS-330, 28% active | Sodium Laureth Sulfate (Stepan) | 57.96 |
| AMPHOSOL ™ CG, 30% active | Cocamidopropyl Betaine (Stepan) | 18.03 |
| Water | | q.s. |
| Citric acid, anhydrous | Citric Acid | 0.15 |
| Preservative | | 0.00015 |
| Disodium EDTA | Disodium EDTA | 0.03 |
| Preservative | | 0.08 |
| Perfume | | 1.00 |
| Polyox WSR-30 | (Amerchol) PEG 90M | 0.06 |
| N-Hance 3196[1] | | 0.15 |

[1](Aqualon-Hercules, Irvine, CA, USA) cationic guar or guar hydroxypropyltrimonium chloride.

The ingredients are stirred, the cationic polymer added last and stirred until homogeneous with no lumps present. The chemical component is added to the bonded web at a rate of 12.4 grams per article. The article is dried overnight in still air at 125° F. until it has lost 6.3 grams of water per article. The article has a Steady Flash Lather Value of about 1,530 ml and a Steady Total Lather Value of about 3,570 ml.

Example 77

A dual textured lathering article is prepared using the webs of Example 39 and the surfactant component of Example 36. Five grams of the surfactant component is melted and applied in 4 stripes to the center of the layers prior to sealing the FQN web layers to the Avgol polypropylene layer. A rectangular article measuring 270 cm² is cut. The article has a Steady Flash Lather Value of about 1,330 ml and a Steady Total Lather Value of about 4,020 ml. The article is useful for producing a steady stream of lather when used in an environment where the supply of water is steady, i.e., a shower.

Example 78

A dual textured lathering article is prepared using the webs of Example 39, which are bonded together in the absence of a chemical component and cut to the same size as the previous example. A chemical component is prepared comprising the following ingredients:

| Ingredient | Supplier or common CTFA name | % of ingredient added |
|---|---|---|
| STEPANOL ™ WA-EXTRA, 30% active | Sodium Lauryl Sulfate (Stepan) | 18.03 |
| STEOL ™ CS-330, 28% active | Sodium Laureth Sulfate (Stepan) | 57.96 |
| AMPHOSOL ™ CG, 30% active | Cocamidopropyl Betaine (Stepan) | 18.03 |
| Water | | q.s. |
| Citric acid, anhydrous | Citric Acid | 0.15 |
| Preservative | | 0.00015 |
| Disodium EDTA | Disodium EDTA | 0.03 |
| Preservative | | 0.08 |
| Perfume | | 1.00 |
| Polyox WSR-30 | (Amerchol) PEG 90M | 0.06 |
| N-Hance 3196 | (Aqualon-Hercules) cationic guar or guar hydroxypropyltrimonium chloride | 0.15 |

The ingredients are stirred, the cationic polymer added last and stirred until homogeneous with no lumps present. The chemical component is added to the bonded web at a rate of 12.4 grams per article. The article is dried overnight in still air at 125° F. until it has lost 6.3 grams of water per article. The article has a Steady Flash Lather Value of 1,530 ml and a Steady Total Lather Value of 3,570 ml.

Examples 79-84

Facial cleansing cloths are prepared. First, a surfactant component is prepared from the following ingredients, which is 25% active in surfactant:

| Ingredient | CTFA, INCI or Common Name | % active ingredient added |
|---|---|---|
| Cocamidopropyl Hydroxysultaine (Stepan) | Cocamidopropyl Hydroxysultaine | 6.563 |
| Hamposyl ™L-30 (Hampshire) | Sodium Lauroyl Sarcosinate | 6.563 |
| Plantaren ™ 2000 N UP (Cognis) | Decyl Glucoside | 6.563 |
| Butylene Glycol | Butylene Glycol | 2.050 |
| Polyox ™ WSR N3000 (Amerchol) | PEG 14M | 1.024 |
| Ucare Polymer JR30M (Amerchol) | Polyquaternium-10 | 0.473 |
| D-Panthenol | Panthenol | 0.394 |
| Salicylic Acid | Salicylic Acid | 0.079 |
| Misc. preservatives, vitamins | | 1.103 |
| Water | | 75.188 |

Webs are prepared as indicated below using the webs from previous examples and the surfactant component sprayed onto the web at the indicated amounts.

|  | Example 79 | Example 80 | Example 81 | Example 82 | Example 83 | Example 84 |
|---|---|---|---|---|---|---|
| Web used | Ex. 27 | Ex. 27 | Ex. 22 | Ex. 28 | Ex. 7 | Ex. 60 |
| Wet add-on rate of surfactant component | 37 gsm | 29 gsm | 29 gsm | 29 gsm | 29 gsm | 37 gsm |

The webs are dried using forced air until dry to the touch, about 5% moisture content based on the total weight. Petrolatum is striped onto the web in two one-inch wide stripes at the rate of 0.167 grams per linear inch (gli) per stripe. A perfume phase comprising a mixture of polyethylene glycol 4600, beta cyclodextrin, fragrance, menthol and water & sodium MA/Diisobutylene Copolymer is added to the web at a rate of 6.6 gsm. The web is cut into 7.5 inch×6.25 inch cloths and packaged. The cloths have the following Mechanical Lather Volume.

| Example 79 | Example 80 | Example 81 | Example 82 | Example 83 | Example 84 |
|---|---|---|---|---|---|
| 450 ml | 390 ml | 420 ml | 520 ml | 490 ml | 470 ml |

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

We claim:
1. A disposable, personal care article comprising:
(A) a spunbond, fibrous nonwoven web having a first surface and a second surface and comprising:
(i) a first region;
(ii) a plurality of discrete integral second regions, the second regions having a discontinuity exhibiting a linear orientation and a deformation comprising a plurality of tufted, looped fibers integral with, but extending from, the first region, wherein the deformation defines a void area disposed between a base and a distal end of the deformation, the void area being wider at the distal end than the base of the deformation; and
(B) a personal care composition.
2. The article of claim 1, wherein said fibrous nonwoven web is comprised of randomly oriented fibers.
3. The article of claim 2, wherein said fibers are selected from the group consisting of natural and synthetic fibers wherein said fibers are selected from the group consisting of monocomponent fibers, multicomponent fibers, multiconstituent fibers, capillary channel fibers, hollow fibers, shaped or lobed fibers and combinations thereof.
4. The article of claim 2, wherein said fibers have a range from about 0.1 denier to about 100 denier.
5. The article of claim 2, wherein said fibers comprise polymers selected from the group consisting of cellulose, polyolefins, polyesters, rayon and mixtures thereof.
6. The article of claim 2, wherein said fibers comprises mixtures of individual fibers made from a polymer selected from the group consisting of cellulose, polyolefins, polyesters, rayon and mixtures thereof.
7. The article of claim 1, wherein said web comprises at least 4 deformations per square centimeter.
8. The article of claim 1, wherein said personal care composition is associated with said web wherein said personal care composition is selected from the group consisting of a treatment composition, a cleansing composition and mixtures thereof.
9. The article of claim 8, wherein said treatment composition comprising agents selected from the group consisting of skin treatment agents, skin conditioning agents and mixtures thereof.
10. The article of claim 9, wherein said skin treatment agents are selected from the group consisting of, vitamins, zeolites, peptides, sunscreen actives, terpene alcohols, desquamation actives, anti-acne actives, anti-wrinkle actives, anti-atrophy actives, anti-oxidants, flavanoids, anti-inflammatory agents, anti-cellulite agents, topical anesthetics, tanning actives, chelators, skin lightening agents, antimicrobial actives, anti-fungal actives, skin soothing actives, skin healing actives, skin moisturizing actives, cosmetic actives and mixtures thereof.
11. The article of claim 9, said skin treatment composition comprising from about 0.05% to about 1600% by weight of said web.
12. The article of claim 9, wherein said skin conditioning agents are selected from the group consisting of petrolatum, fatty acids, esters of fatty acids, fatty alcohols, ethoxylated alcohols, polyol polyesters, glycerine, glycerin mono-esters, glycerin polyesters, epidermal and sebaceous hydrocarbons, lanolin, straight and branched hydrocarbons, silicone oil, silicone gum, vegetable oil, vegetable oil adduct, hydrogenated vegetable oils, nonionic polymers, natural waxes, synthetic waxes, polyolefinic glycols, polyolefinic monoester, polyolefinic polyesters, cholesterols, cholesterol esters and mixtures thereof.
13. The article of claim 9, said skin conditioning agents comprising from about 0.05% to about 1600% by weight of said web.
14. The article of claim 8, wherein said cleansing compositions are selected from the group consisting of anionic surfactant selected from the group consisting of sarcosinates, sulfates, isethionates, phosphates, taurates, lactylates, glutamates, soaps and mixtures thereof; nonionic surfactant is selected from the group consisting of amine oxides, alkyl glucosides, alkyl polyglucosides, polyhydroxy fatty acid amides, alkoxylated fatty acid esters, sucrose esters, and mixtures thereof; amphoteric surfactants selected from the group consisting of betaines, sultaines, hydroxysultaines, alkylimino-acetates, iminodialkanoates, aminoalkanoates, and mixtures thereof; non-lathering surfactant selected from the group consisting of polyethylene glycol 20 sorbitan monolaurate, polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, polyoxyethylene 20 sorbitan trioleate, sorbitan monolaurate, polyoxyethylene 4 lauryl ether sodium stearate, polyglyceryl-4 isostearate, hexyl laurate, PPG-2 methyl glucose ether distearate, ceteth-10, diethanolamine cetyl phosphate, glyceryl stearate, PEG-100 stearate and mixtures thereof.

15. The article of claim 8, wherein the article comprises less than about 20% by weight of a fluid.

16. The article of claim 8, wherein the article comprise from about 20% to about 40% by weight of a fluid.

17. The article of claim 8, wherein the article comprises from about 40% to about 95% by weight of a fluid.

18. The article of claim 8, wherein said cleansing composition generates a Steady Total Lather Volume of at least about 1400 ml.

19. The article of claim 8, wherein said cleansing composition generates a Mechanical Lather Volume of at least 85 ml.

20. The article of claim 8, wherein said cleansing composition generates a Steady Flash Lather Volume of less than about 700 ml.

21. A kit for a personal care article comprising:
(A) A personal care composition; and
(B) a plurality of spunbond, fibrous nonwoven webs having a first surface and a second surface and comprising substantially randomly-oriented fibers, said fibrous web comprising:
  (i) a first region;
  (ii) a plurality of discrete integral second regions, the second regions having a discontinuity exhibiting a linear orientation and a deformation comprising a plurality of tufted, looped fibers integral with but extending from the first region, wherein the deformation defines a void area disposed between a base and a distal end of the deformation, the void area being wider at the distal end than the base of the deformation.

* * * * *